US007790432B2

(12) United States Patent
Chatterjee et al.

(10) Patent No.: US 7,790,432 B2
(45) Date of Patent: Sep. 7, 2010

(54) ALANINE 2,3-AMINOMUTASES AND RELATED POLYNUCLEOTIDES

(75) Inventors: Ranjini Chatterjee, Belmont, CA (US); Kenneth W. Mitchell, San Jose, CA (US); Susan Y. Louie, San Francisco, CA (US); Richard J. Fox, Kirkwood, MO (US); Michelle Chen, Moorpark, CA (US)

(73) Assignee: Codexis, Inc., Redwood City, CA (US)

( * ) Notice: Subject to any disclaimer, the term of this patent is extended or adjusted under 35 U.S.C. 154(b) by 135 days.

(21) Appl. No.: 11/919,271

(22) PCT Filed: Oct. 25, 2005

(86) PCT No.: PCT/US2005/038552

§ 371 (c)(1), (2), (4) Date: Mar. 20, 2009

(87) PCT Pub. No.: WO2006/047589

PCT Pub. Date: May 4, 2006

(65) Prior Publication Data

US 2010/0099143 A1 Apr. 22, 2010

Related U.S. Application Data

(60) Provisional application No. 60/622,206, filed on Oct. 25, 2004.

(51) Int. Cl.

| | |
|---|---|
| ***C12N 9/88*** | (2006.01) |
| ***C12N 1/20*** | (2006.01) |
| ***C12N 1/00*** | (2006.01) |
| ***C12N 15/00*** | (2006.01) |
| ***C07H 21/02*** | (2006.01) |

(52) U.S. Cl. ............... 435/232; 435/252.33; 435/254.1; 435/320.1; 536/23.1; 536/23.2

(58) Field of Classification Search ....................... None
See application file for complete search history.

(56) References Cited

U.S. PATENT DOCUMENTS 6,248,874 B1 6/2001 Frey et al.

(Continued)

FOREIGN PATENT DOCUMENTS

WO WO 01/16346 A1 3/2001

(Continued)

OTHER PUBLICATIONS

Abe, T. et al., 1998, "High-performance liquid chromatographic determination of β-alanine, β-aminoisobutyric acid and γ-aminobutyric acid in tissue extracts and urine of normal and (aminooxy)acetate-treated rats," *J Chromatogr B.* 712(1-2):43-9.

(Continued)

*Primary Examiner*—Nashaat T Nashed

(57) ABSTRACT

The present invention is directed to polypeptides that have enhanced alanine 2,3-aminomutase (AAM) activity and/or thermostability relative to the wild-type enzymes that have incidental AAM activity as a result of cross reactivity with alanine. In addition, the present invention is directed to a polynucleotides that encodes for the AAM polypeptides of the present invention, to nucleic acid sequences comprising the polynucleotides, to expression vectors comprising the polynucleotides operatively linked to a promoter, to host cells transformed to express the AAM polypeptides, and to a method for producing the AAM polypeptides of the present invention.

19 Claims, 8 Drawing Sheets

α–alanine β-alanine

U.S. PATENT DOCUMENTS

| | | | |
|---|---|---|---|
| 7,309,597 | B2 | 12/2007 | Liao et al. |
| 7,655,451 | B2 | 2/2010 | Liao et al. |
| 2002/0173637 | A1 | 11/2002 | Frey et al. |
| 2003/0113882 | A1 | 6/2003 | Frey et al. |
| 2005/0221466 | A1 | 10/2005 | Liao et al. |
| 2009/0031453 | A1 | 1/2009 | Jessen et al. |

FOREIGN PATENT DOCUMENTS

| | | | |
|---|---|---|---|
| WO | WO 02/42418 | A2 | 5/2002 |
| WO | WO 03/062173 | A2 | 7/2003 |
| WO | WO 2005/118719 | A2 | 12/2005 |
| WO | WO 2006/047589 | A2 | 5/2006 |
| WO | WO 2007/047680 | A2 | 4/2007 |
| WO | WO 2007/047773 | A2 | 4/2007 |

OTHER PUBLICATIONS

Chen, D. et al., 2000, "A novel 2,3-aminomutase encoded by the yodO gene of *Bacillus subtilis*: characterization and the observation of organic radical intermediates," *Biochem J.* 348:539-549.

Chen, D. et al., 2001, "Identification of Lysine 346 as a Functionally Important Residue for Pyridoxal 5'-Phosphate Binding and Catalysis in Lysine 2,3-Aminomutase from *Bacillus subtilis," Biochemistry* 40(2):596-602.

Chirpich, T. P. et al., 1970, "Lysine 2,3.Aminomutase purification and properties of a pyridoxal phosphate and s-adenosylmethionine-activated enzyme," *J Biol. Chem* 245(7):1778-1789.

Dalluge, J. et al., 2005, "Discovery of enzymatic activity using stable isotope metabolite labeling and liquid chromatography—Mass spectrometry," *Anal Chem.* 77:6737-6740.

Genbank Accession No. AAB81159.

Genbank Accession No. CAB 13860.

Genbank Accession No. AE017175.

International Preliminary Examination Report & Written Opinion of PCT/US2005/038552 issued May 1, 2007.

International Search Report of PCT/US2005/038552 dated Feb. 26, 2006.

Kunst, F. et al., 1997, "The complete genome sequence of the Gram positive bacterium *Bacil lus subtilis* ," *Nature* 390:249-256.

Lieder, K. et al., 1998, "S-Adenosylmethionine-dependent reduction of lysine 2,3-aminomutase and observation of the catalytically functional iron sulfur centers by electron paramagnetic resonance ," *Biochemistry* 37:2578-2585.

Macbeath, G. et al., 1998, "UGA Read-Through Artifacts—When popular gene expression systems need a patch ," *Biotechniques* 24:789-794.

Parker, J, "Errors and alternatives in Reading the Universal Code ," *Microbiol. Rev.* 53(3):273-298.

Petrovich, R. M. et al., *J Biol. Chem.* 266(12):7656-7660.

U.S. Appl. No. 11/581,946, filed on Oct. 16, 2006.

α-alanine β-alanine

*SEQ ID NO:*

1

50

P_GI2529467_G8_AAB81159.1_ *60* (1)
MKNKWYKPKRHWKEIELWKDVPEEKWNDWLWQLTHTVRTLDDLKKVINLT
P_GI2634361_EMB_CAB13860.1_ *61* (1)
MKNKWYKPKRHWKEIELWKDVPEEKWNDWLWQLTHTVRTLDDLKKVINLT
P_S00701550 *59* (1)
MKNKWYKPKRHWKEIELWKDVPEEKWNDWLWQLTHTVRTLDDLKKVINLT
P_S00701551 *53* (1) ----------
MSLKDKFETHVSQEDWNDWKWQVRNRIKTVEELKKYIPLT
P_S00701552 *55* (1) --------
MAESRRKYYEPDVTDEQWYDWHWQVLNRIKTLDQLKKYVTIET
P_S01032894 *57* (1) -------
MNTVNTRKKFEPNVTDEEWNDWTWQVKNRLKSVEDLEKYVDLS
Consensus *62* (1)
MKNKWYKPKRHWKEIELWKDVPEEKWNDWLWQLTHTVRTLDDLKKVINLT

P_GI2529467_G8_AAB81159.1_ (51)
EDEEEGVRISTKTIPLNITPYYASLMDPDNPRCPVRMQSVPLSEEMHKTK
P_GI2634361_EMB_CAB13860.1_ (51)
EDEEEGVRISTKTIPLNITPYYASLMDPDNPRCPVRMQSVPLSEEMHKTK
P_S00701550 (51)
EDEEEGVRISTKTIPLNITPYYASLMDPDNPRCPVRMQSVPLSEEMHKTK
P_S00701551 (41)
PEEEEGVKRCLDTLRMAITPYYLSLIDVENPNDPVRKQAVPLSLEEHRAA
P_S00701552 (43)
AEEEEGVKESPKVLRMAITPYYLSLIDPENPNCPIRKQAIPTQQELVRAP
P_S01032894 (44)
EEETEGVVRTLETLRMAITPFYFSLIDLNSDRCPIRKQAIPTIREIHQSD
Consensus (51)
EDEEEGVRISTKTIPLNITPYYASLMDPDNPRCPVRMQSVPLSEEMHKTK

FIG. 4B

```
                                     101                                              150
P_GI2529467_G8_AAB81159.1_    (101)  YDLEDPLHEDEDSRVPGLTHRYPDRVLFLVTNQCSMYCRYCTRRRFSGQI
P_GI2634361_EMB_CAB13860.1_   (101)  YDLEDPLHEDEDSPVPGLTHRYPDRVLFLVTNQCSMYCRYCTRRRFSGQI
               P_S00701550    (101)  YDMEDPLHEDEDSPVPGLTHRYPDRVLFLVTNQCSVYCRHCTRRRFSGQI
               P_S00701551     (91)  SDMEDPLHEDGDSPVPGLTHRYPDRVLLLMTDQCSVYCRHCTRRRFAGRT
               P_S00701552     (93)  EDQVDPLSEDEDSPVPGLTHRYPDRVLFLITDKCSMYCRHCTRRRFAGQK
               P_S01032894     (94)  ADMLDPLHEDEDSPVPGLTHRYPDRVLLLITDMCSVYCRHCTRRRFAGSS
                 Consensus    (101)  YDMEDPLHEDEDSPVPGLTHRYPDRVLFLVTNQCSVYCRHCTRRRFSGQI
```

FIG. 4C

```
                                     151                                              200
P_GI2529467_G8_AAB81159.1_    (151)  GMGVPKKQLDAAIAYIRETPEIRDCLISGGDGLLINDQILEYILKELRSI
P_GI2634361_EMB_CAB13860.1_   (151)  GMGVPKKQLDAAIAYIRETPEIRDCLISGGDGLLINDQILEYILKELRSI
               P_S00701550    (151)  GMGVPKKQLDAAIAYIRETPEIRDCLISGGDGLLINDQILEYILKELRSI
               P_S00701551    (141)  DSAVDTKQIDAAIEYIKNEPQVRDVLLSGGDALLISDEKLEYTIRRLREI
               P_S00701552    (143)  DASSPSERIDRCLDYIANTPTVRDVLLSGGDALLVSDERLEYILKRLREV
               P_S01032894    (144)  DGAMPMDRIDKATEYIAKTPQVREVLLSGGDALLVSNKKEESITQKLRAI
                 Consensus    (151)  GMGVPKKQLDAAIAYIRETPEIRDCLISGGDGLLINDQILEYILKELRSI
```

FIG. 4D

```
                                   201                                              250
P_GI2529467_G8_AAB81159.1_   (201) PHLEVIRIGTRAPVVFPQRITDHLCEILKKYHPVWLNTHFNTSIEMTEES
P_GI2634361_EMB_CAB13860.1_  (201) PHLEVIRIGTRAPVVFPQRITDHLCEILKKYHPVWLNTHFNTSIEMTEES
                P_S00701550  (201) PHLEVIRIGTRAPVVFPQRITDHLCEILKKYHPVWLNTHFNTSIEMTEES
                P_S00701551  (191) PHVEVIRIGSRVPVVMPQRITPELVSMLKKYHPVWLNTHFNHPNEITEES
                P_S00701552  (193) PHVEIVRIGSRTPVVLPQRITPQLVDMLKKYHPVWLNTHFNHPNEVTEEA
                P_S01032894  (194) PHVEIIRIGSRTPVVLPQRITPELCNMLKKYHPIWMNTHFNHPQEVTPEA
                  Consensus  (201) PHLEVIRIGTRAPVVFPQRITDHLCEILKKYHPVWLNTHFNTSIEMTEES
```

FIG. 4E

```
                                   251                                              300
P_GI2529467_G8_AAB81159.1_   (251) VEACEKLVNAGVPVGNQAVVLAGINDSVPIMKKLMHDLVKIRVRPYYIYQ
P_GI2634361_EMB_CAB13860.1_  (251) VEACEKLVNAGVPVGNQAVVLAGINDSVPIMKKLMHDLVKIRVRPYYIYQ
                P_S00701550  (251) VEACEKLVNAGVPVGNQAVVLAGINDSVPIMKKLMHDLVKIRVRPYYIYQ
                P_S00701551  (241) KRACELLADAGIPLGNQSVLLAGVNDCMHVMKKEVNDLVKIRVRPYYIYQ
                P_S00701552  (243) VEACERMANAGIPLGNQTVLLRGINDCTHVMKRLVHLLVKMRVRPYYIYV
                P_S01032894  (244) KKACEMLADAGVPLGNQTVLLRGINDSVPVMKRLVHDLVMMRVRPYYIYQ
                  Consensus  (251) VEACEKLVNAGVPVGNQAVVLAGINDSVPIMKKLMHDLVKIRVRPYYIYQ
```

FIG. 4F

```
                                   301                                               350
P_GI2529467_G8_AAB81159.1_   (301) CDLSEGIGHFRAPVSKGLEIIEGLRGHTSGYAVPTFVVDAPGGGGKIALQ
P_GI2634361_EMB_CAB13860.1_  (301) CDLSEGIGHFRAPVSKGLEIIEGLRGHTSGYAVPTFVVDAPGGGGKIALQ
                 P_S00701550 (301) CDLSEGIGHFRAPVSKGLEIIEGLRGHTSGYAVPTFVVHAPGGGGKIALQ
                 P_S00701551 (291) CDLSVQIEHFRTPVAKGIEEIEGLRGHTSGYCVPTFVVHAPGGGGKTPVM
                 P_S00701552 (293) CDLSLGIGHFRTPVSKGIETIENLRGHTSGYAVPTFVVGAPGGGGKIPVT
                 P_S01032894 (294) CDLSMGLEHFRTPVSKGIEIIEGLRGHTSGYAVPTFVVHAPGGGGKTPVM
                   Consensus (301) CDLSEGIRHFRAPVSKGLEIIEGLRGHTSGYAVPTFVVHAPGGGGKIALQ
```

FIG. 4G

```
                                   351                                               400
P_GI2529467_G8_AAB81159.1_   (351) PNYVLSQSPDKVILRNFEGVITSYPEPENYIPNQADAYFESVFPETADKK
P_GI2634361_EMB_CAB13860.1_  (351) PNYVLSQSPDKVILRNFEGVITSYPEPENYIPNQADAYFESVFPETADKK
                 P_S00701550 (351) PNYVLSQSPDKVILRNFEGVITSYPEPENYIPNQADAYFESVFPETADKK
                 P_S00701551 (341) PNYVISQNHNKYILRNFEGVITTYDEPDHYTFHCDCDVCTGKT-----NV
                 P_S00701552 (343) PNYVVSQSPRHVVLRNYEGVITTYTEPENYHEECDCEDCRAG-------K
                 P_S01032894 (344) PQYVISQSPHRVVIRNFEGVITTYTEPENYTHEPCYDEEKFEK-----MY
                   Consensus (351) PNYVLSQSPDKVILRNFEGVITSYPEPENYIPNQADAYFESVFPETADKK
```

FIG. 4H

```
                                        401                                               450
P_GI2529467_G8_AAB81159.1_      (401)  EPIELSAIFADKEVSFTPENVDRIKRREAYIANPEHETLKDRRERRDQLK
P_GI2634361_EMB_CAB13860.1_     (401)  EPIGLSAIFADKEVSFTPENVDRIKRREAYIANPEHETLKDRREKRDQLK
                P_S00701550     (401)  EPIGLSAIFADKEVSFTPENVDRIKRREAYIANPEHETLKDRREKRDQLK
                P_S00701551     (386)  HKVGVAGLLNGETATLEREGLERKQRGHH---------------------
                P_S00701552     (386)  HKEGVAAESGGQQLAIEPSDLARKKRKFDKN-------------------
                P_S01032894     (389)  EISGVYMLDEGLEMSLEESHLARHERNKKRAEAEGKK-------------
                  Consensus     (401)  EPIGLSAIFADKEVSSTPENVDRIKRREAYIANPEHETLKDRREKRGQLK
```

FIG. 4I

```
                                        451                  471
P_GI2529467_G8_AAB81159.1_      (451)  EKKFLAQQKKQKETECGGDSS-
P_GI2634361_EMB_CAB13860.1_     (451)  EKKFLAQQKKQKETECGGDSS-
                P_S00701550     (451)  EKKFLAQQKKQKETECGGDSS-
                P_S00701551     (415)  ----------------------
                P_S00701552     (417)  ----------------------
                P_S01032894     (426)  ----------------------
                  Consensus     (451)  EKKFLAQQKKQKETECGGDSS
```

FIG. 4J

ALANINE 2,3-AMINOMUTASES AND RELATED POLYNUCLEOTIDES

This application is a 371 application of PCT/US2005/038552, filed Oct. 25, 2005, which claims the benefit of U.S. Ser. No. 60/622,206, filed Oct. 25, 2004.

FIELD OF THE INVENTION

The present invention is related to the field of enzymology, and particularly to the field of alanine 2,3-aminomutase (AAM) enzymology. More specifically, the present invention is directed to alanine 2,3-aminomutase polypeptides having improved enzymatic activity (i.e., high substrate turnover) and stability, and to polynucleotides sequences encoding for the improved alanine 2,3-aminomutase polypeptides. The present invention is useful because the alanine 2,3-aminomutase polypeptides can be coupled to other enzymes to produce synthetic organic chemicals, such as pantothenic acid or 3-hydroxypropionic acid in high yields.

BACKGROUND OF THE INVENTION

Organic chemicals such as organic acids, esters, and polyols can be used to synthesize plastic materials and other products. To meet the increasing demand for organic chemicals, more efficient and cost-effective production methods are being developed which utilize raw materials based on carbohydrates rather than hydrocarbons. For example, certain bacteria have been used to produce large quantities of lactic acid used in the production of polylactic acid.

3-hydroxypropionic acid (3-HP) is an organic acid. Several chemical synthesis routes have been described to produce 3-HP, and biocatalytic routes have also been disclosed (WO 01/16346 to Suthers et al.). 3-HP has utility for specialty synthesis and can be converted to commercially important intermediates by known methods in the chemical industry, e.g., acrylic acid by dehydration, malonic acid by oxidation, esters by esterification reactions with alcohols, and 1,3-propanediol by reduction.

The compound 3-HP can be produced biocatalytically from PEP or pyruvate, through a key beta-alanine intermediate (FIG. 1). Beta-alanine can be synthesized in cells from carnosine, beta-alanyl arginine, beta-alanyl lysine, uracil via 5,6-dihydrouracil and N-carbamoyl-beta-alanine, N-acetyl-beta-alanine, anserine, or aspartate. However, these routes are commercially unviable because they require rare precursors or starting compounds that are more valuable than 3-HP. Therefore, production of 3-HP using biocatalytic routes would be more efficient if alpha-alanine could be converted to beta-alanine directly (FIG. 1). Unfortunately, a naturally occurring enzyme that inter-converts alpha-alanine to beta-alanine has not yet been identified. It would be advantageous if enzymatic activities that carry out the conversion of alpha-alanine to beta-alanine were identified, such as an alanine 2,3-aminomutase. Accordingly, it is one object of the present invention to identify enzymes with improved alanine 2-3-aminomutase activity.

Lysine 2,3-aminomutase (KAM), which catalyzes the anaerobic interconversion of lysine to beta-lysine, was first described by Barker in *Clostridium* SB4 (now *C. subterminale*) catalyzing the first step in the fermentation of lysine. KAM has been purified from *C. subterminale*, the gene cloned and expressed in *E. coli*. See e.g., U.S. Pat. No. 6,248,874, which issued on Jun. 19, 2001 to Frey et al., the whole of which is hereby incorporated herein by reference. The specific activity of purified KAM from *C. subterminale* SB4 cells has been reported as 3040 units/mg (Lieder et. al., Biochemistry 37:2578 (1998)), where a unit is defined as μmoles lysine/min. The corresponding purified recombinantly produced KAM had equivalent enzyme activity (34.5±1.6 μmoles lysine/min/mg protein). See U.S. Patent Application Publication No. 2003/0113882 A1, which published on Jun. 19, 2003 to Frey et al., the whole of which is incorporated herein by reference.

Based upon the sequence of the KAM from *C. subterminale*, KAM genes have been annotated in the genomes of other organisms. However, in most cases, the enzymatic activities of the polypeptides encoded by these genes have not been confirmed. Exceptions are the *B. subtilis* gene (Chen, D., Ruzicka, F. J., and Frey, P. A. (2000) Biochem. J. 348:539-549)), and the *Porphyromonas gingivalis* and *F. nucleatum* genes. The *B. subtilis* KAM, encoded by the yodO gene, is more resistant to $O_2$ than the *C. subterminale* KAM, but it is markedly less active. As reported by Frey, the *B. subtilis* KAM has a specific activity of only 0.62 U/mg.

*C. subterminale* SB4 KAM has been reported to have some cross-reactivity with L-alanine, converting it into beta-alanine. See U.S. Patent Application Publication No. 2003/0113882 A1. WO 03/062173 and WO 02/42418 disclose the first reports of AAM activity based upon modification of kam genes. In these applications, the synthetic aam genes had AAM activity as detected by the complementation of a ΔpanD *E. coli* strain. However, because alanine is not the natural substrate for this enzyme, the activity for this conversion is substantially less than the activity for conversion of lysine—its natural substrate. The AAM activity of a variant of *B. subtilis* KAM that also had AAM activity at approximately 0.001 U/mg. It is an object of the present invention to provide polynucleotides encoding a polypeptide having substantially enhanced AAM activity over that found in the wild-type enzymes.

SUMMARY OF THE INVENTION

The present invention has multiple aspects. In one aspect, the present invention is directed to polypeptides that catalyze the reaction of FIG. 1. In one embodiment of this first aspect, the present invention is directed to a polypeptide having alanine 2,3-aminomutase (AAM) activity, preferably as measured by the assay of Example 8, and, (a) having a polypeptide selected from the group consisting of SEQ ID NO: 2, 4, 6, 8, 10, 12, 14, 16, 18, 20, 22, 24, 26, 28, 30, 32, 34, 36, 38, 40, 42, 44, 46, 48 and 51;

(b) having an amino acid sequence which has at least 98% homology, with the amino acid sequence selected from the group consisting of SEQ ID NO: 2, 22, 28, 32, and 36;

(c) having an amino acid sequence which has at least 99% homology, with the amino acid sequence selected from the group consisting of SEQ ID NO: 4, 6, 8, 12, 16, 24, 26, 30, 34 and 40;

(d) being a polypeptide encoded by a nucleic acid sequence which hybridizes under high stringency conditions with either (i) the nucleotide sequence of SEQ ID NO: 1, 3, 5, 7, 9, 11, 13, 15, 17, 19, 21, 23, 25, 27, 29, 31, 33, 35, 37, 41, 43, 45, 47 or 49; (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.); or (e) being a variant of the polypeptide of (c) comprising a substitution, deletion, and/or insertion of one to six amino acids therefrom and having AAM activity from about 1 to about 30 μM β-alanine produced/hour 1 cell OD at pH 7.0-7.6, 25° C.

Collectively, the polypeptides of (b) and (c) above are referred to herein as "homologous polypeptides." For purposes of the present invention, the degree of homology between two amino acid sequences is expressed as "percent homology," "percent identity," "% identity," "percent identical," and "% identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

In one embodiment, the present invention is also directed to an AAM polypeptide as described herein in isolated and purified form.

In another embodiment, the present invention is directed to an AAM polypeptide as described herein in lyophilized form.

In yet another embodiment, the present invention is directed to a composition comprising an AAM polypeptide as described herein and a suitable carrier, typically a buffer solution, more typically an aqueous buffer solution having a pH between 6.0 and 8.0. The composition may also be in a lyophilized form.

The novel AAM polypeptides of the present invention have significantly enhanced AAM activity relative to the wild-type KAM polypeptides from which they are ultimately derived. By significantly enhanced AAM activity is meant that the AAM polypeptide of the present invention has an AAM activity within the range of about 1 to about 32 M β-alanine produced/hour 1 cell OD (units), preferably from about 10 to about 32 units, more preferably from about 20 to about 32 units; most preferably from about 25 to about 32 units.

Preferred AAM polypeptides of the present invention have an amino acid sequences of SEQ ID NOs: 2, 6, 12, 16, 20, 24, 28, 30, 32, 34, 38, 44, 46 or 48; more preferably they have an amino acid sequence of SEQ ID NOs: 6, 12, 28, 34, 46 or 48; most preferably, they have an amino acid sequence of SEQ ID NOs: 28 or 34.

One of the grandparent molecules is the KAM of *Bacillus subtilis*, which had no detectible AAM activity. The DNA encoding this grandparent molecule was modified as described in WO 03/062173, entitled "Alanine 2,3-aminomutase," to produce a polypeptide having a detectible alanine 2,3-aminomutase activity.

In the present application, the applicants utilized as one parent molecule a polynucleotide sequence of SEQ ID NO: 58, which encoded the 471 residue polypeptide of SEQ ID NO: 59 and which exhibited an AAM activity of approximately 0.001 U/mg (units/mg of cell mass). The molecule of SEQ ID NO: 59 differs from the wild-type *B. subtilis* KAM, which had no detectible AAM activity, by having the following four (4) amino acid substitutions: L103M, M136V, Y140H and D339H.

In yet another embodiment, the present invention is directed to a polypeptide having from about 1 to about 32 units of AAM activity and typically varying from the polypeptide of SEQ ID NO: 59 by 1-7 amino acid residues, more typically by 1-6 amino acid residues, even more typically by 1-5 amino acid residues, and most typically by 1-4 amino acid residues.

In its second aspect, the present invention is directed to a polynucleotide sequence that encodes for the correspondingly referenced AAM polypeptide. Given the degeneracy of the genetic code, the present invention is also directed to any polynucleotide that encodes for the above referenced AAM polypeptides of the present invention. In another preferred embodiment, the present invention is directed to certain specific polynucleotides of SEQ ID NOS: 1, 3, 5, 7, 9, 11, 13, 15, 17, 19, 21, 23, 25, 27, 29, 31, 33, 35, 37, 39, 41, 43, 45, 47 and 49 that encode for the novel AAM polypeptides of SEQ ID NOS: 2, 4, 6, 8, 10, 12, 14, 16, 18, 20, 22, 24, 26, 28, 30, 32, 34, 36, 38, 40, 42, 44, 46, 48 and 51, respectively. Preferred polynucleotides encode for a polypeptide of SEQ ID NO: 2, 6, 12, 16, 20, 24, 28, 30, 32, 34, 38, 44, 46 or 48; more preferably they encode a polypeptide of SEQ ID NO: 6, 12, 28, 34, 46 or 48; most preferably, they have a polypeptide of sequence of SEQ ID NO: 28 or 34.

In a third aspect, the present invention is directed to a nucleic acid construct, a vector, or a host cell comprising a polynucleotide sequence encoding an AAM polypeptide of the present invention operatively linked to a promoter.

In a fourth aspect, the present invention is directed to a method of making an AAM polypeptide of the present invention comprising (a) cultivating a host cell transformed with a nucleic acid sequence encoding an AAM polypeptide of the present invention under conditions suitable for production of the polypeptide; and (b) providing glucose to the cultivated host cells under conditions suitable for the production of β-alanine. The β-alanine may be optionally recovered from the cells.

In a fifth aspect, the present invention is directed to a method of producing b-alanine comprising (a) cultivating a host cell transformed with a nucleic acid sequence encoding an AAM polypeptide of the present invention under conditions suitable for production of the polypeptide; and (b) providing glucose to the cultivated host cells under conditions suitable for the production of b-alamine. The b-alanine may be optionally recovered from the cells.

BRIEF DESCRIPTION OF SEVERAL VIEWS OF THE DRAWINGS

FIGS. 4A-4J in combination provide an alignment chart of the amino acid sequences of four parental polypeptides that were used to produce the AAM of the present invention. The parental polypeptides were non-naturally occurring and derived in part from the KAM of *Clostrisium stricklandii* (SEQ ID NO: 53), *Porphyromonas gingivalis* (SEQ ID NO: 55), *Fusobacterium nucleatuim* (SEQ ID NO: 57), and *Bacillus subtilis* (SEQ ID NO: 59), respectively. The sequences of two wild-type KAM are disclosed in SEQ ID NOS: 60 (P GI2529467_G_AAB81159.1_) and 61

Figure 1:
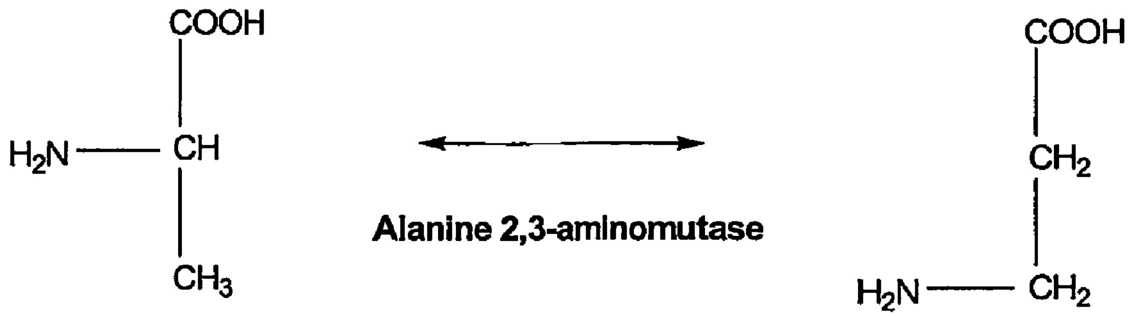
FIG. 1 shows the reversible reaction between alpha-alanine (i.e., L-alanine or 2-aminopropionic acid) and beta-alanine (3-aminopropionic acid) that is catalyzed by alanine 2,3-aminomutase.
Figure 2:
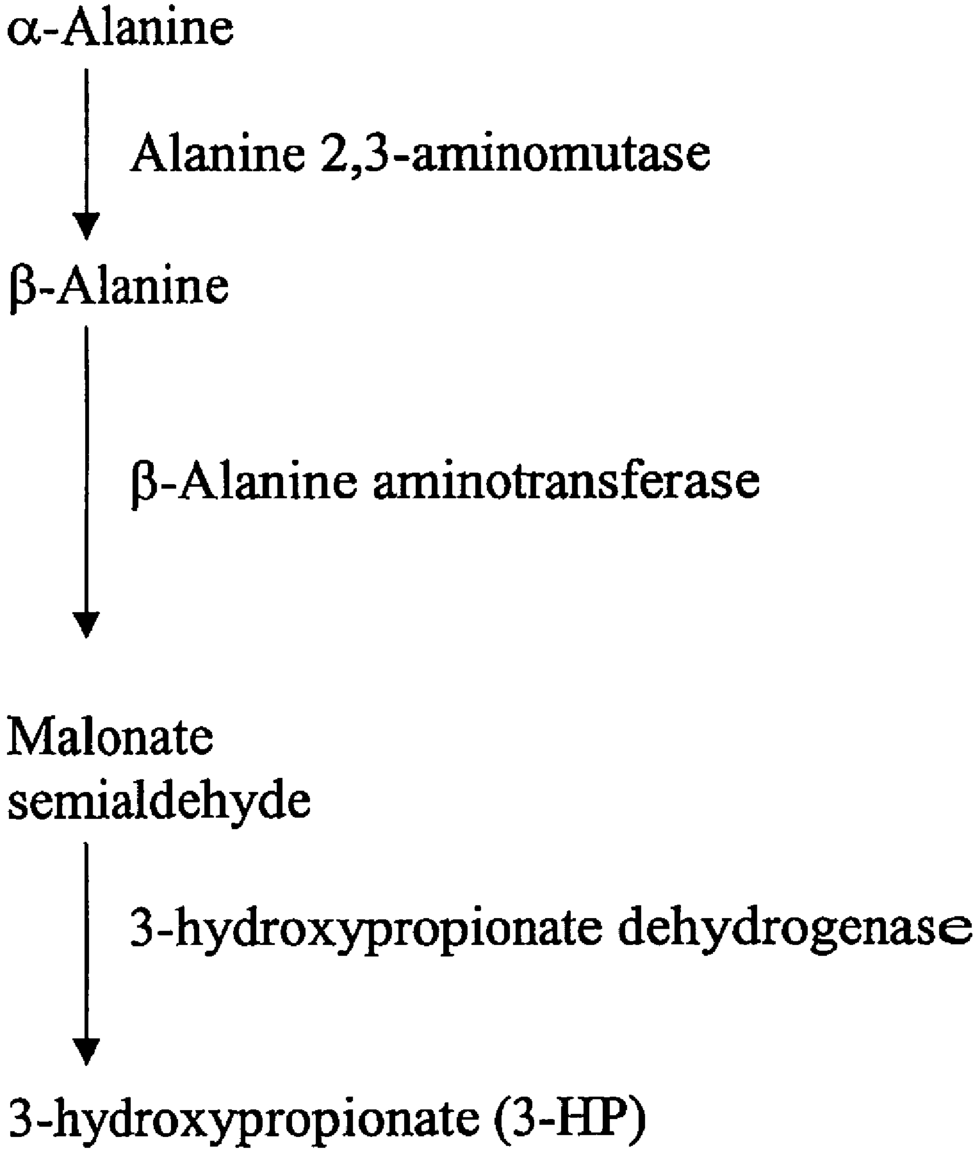
FIG. 2 is a pathway for 3-hydroxypropionate (3-HP) synthesis from alpha-alanine, via beta-alanine as an intermediate.

(P_GI2634361_EMB_CAB13860.1_). A consensus sequence is also provided as SEQ ID NO: 62).

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

The present invention has multiple aspects. In one aspect, the present invention is directed to a polypeptide having alanine 2,3-aminomutase (AAM) activity, preferably as measured by the assay of Example 8, and (a) having a polypeptide selected from the group consisting of SEQ ID NO: 2, 4, 6, 8, 10, 12, 14, 16, 18, 20, 22, 24, 26, 28, 30, 32, 34, 36, 38, 40, 42, 44, 46, 48 and 51:

(b) having an amino acid sequence which has at least 98% homology, with the amino acid sequence selected from the group consisting of SEQ ID NO: 2, 22, 28, 32, and 36;

(c) having an amino acid sequence which has at least 99% homology, with the amino acid sequence selected from the group consisting of SEQ ID NO: 4, 6, 8, 12, 16, 24, 26, 30, 34 and 40;

(d) being a polypeptide encoded by a nucleic acid sequence which hybridizes under high stringency conditions with either (i) the nucleotide sequence of SEQ ID NO: 1, 3, 5, 7, 9, 11, 13, 15, 17, 19, 21, 23, 25, 27, 29, 31, 33, 35, 37, 41, 43, 45, 47 or 49; (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.); or (e) being a variant of the polypeptide of (d) comprising a substitution, deletion, and/or insertion of one to six amino acids therefrom and having AAM activity from about 1 to about 30 μM β-alanine produced/hour 1 cell OD at pH 7.0-7.6, 25° C.

Collectively, the polypeptides of (b) and (c) above are referred to herein as "homologous polypeptides." For purposes of the present invention, the degree of homology between two amino acid sequences is expressed as "percent homology," "percent identity," "% identity," "percent identical," and "% identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

AAM polypeptides are sensitive to oxygen and are preferably maintained and used in an oxygen deficient environment. If the AAM polypeptide becomes inactivated due to exposure to oxygen, it can be activated by anaerobic incubation with a sulfhydryl compound for one hour at 37° C. in accordance with the method described in Chirpich, et al., Journal Biol. Chem., 245(7): 1778-1789 (1970), which is incorporated herein by reference in its entirety. AAM polypeptides of the present invention are preferably utilized in whole cell form (i.e., as a whole cell transformed with an AAM polynucleotide that is used under conditions such that the encoded AAM polypeptide is expressed in the cell) or alternatively, both isolated and utilized under anoxic conditions. AAM polypeptides of the present invention may be isolated, and optionally purified, under anaerobic conditions (e.g., under a nitrogen atmosphere) in accordance with the method described in Petrovich, et al., Journal Biol. Chem., 266(12):7656-7660 (1991), which describes the isolation and purification of lysine-2,3-aminomutase and which is incorporated herein by reference in its entirety. As used herein, the term "anoxic" refers to oxygen deficient. The AAM polypeptides in whole cell form or as isolated enzymes may be lyophilized. In yet another embodiment, the present invention is directed to a composition comprising an AAM polypeptide as described herein (e.g., in whole cell form or as an isolated polypeptide) and a suitable carrier, typically a buffer, more typically an aqueous buffer solution having a pH from about 6.0 to about 8.0. It is also within the scope of the present invention that the aqueous buffered composition be lyophilized to provide a composition in a lyophilized form, wherein the composition is reconstituted by the addition of an aqueous based composition.

In one embodiment, the present invention is also directed to an AAM polypeptide as described herein in isolated and purified form.

In another embodiment, the present invention is directed to an AAM polypeptide as described herein in lyophilized form. Lyophilization is performed using standard lyophilization equipment. Typically, a solution containing the polypeptide is dispensed in an appropriate sized vial, frozen and placed under reduced pressure to cause the water to evaporate, leaving the lyophilized (freeze-dried) polypeptide behind. Prior to use, the lyophilized polypeptide is reconstituted with distilled water or an appropriate buffer solution.

In yet another embodiment, the present invention is directed to a composition comprising an AAM polypeptide as described herein and a suitable carrier, typically a buffer solution, more typically an aqueous buffer solution having a pH between 6.0 and 8.0. The composition may also be in a lyophilized form.

The novel AAM polypeptides of the present invention have significantly enhanced AAM activity relative to the wild-type KAM polypeptides from which they are ultimately derived. By significantly enhanced AAM activity is meant that the AAM polypeptide of the present invention has an AAM activity within the range of about 1 to about 32 μM β-alanine produced/hour 1 cell OD (units), preferably from about 10 to about 32 units, more preferably from about 20 to about 32 units; most preferably from about 25 to about 32 units.

Table 1 provides a chart showing the AAM activities of the various AAM polypeptides of the present invention, identified by their clone number and SEQ ID NO. In Table 1, the $OD_{600nm}$ is reported at harvest after 5 hours (t=5) of incubation. Table 1 also reports the total μM of β-alanine produced after 5 hours per 1 cell OD. Finally, the last column of Table 1 reports the rate of β-alanine (μM) produced/hr/1 cell OD.

TABLE 1

| Seq. ID No. | Harvest $OD_{600nm}$ t = 5 | uM β-alanine produced at t = 5/1 cell OD | Rate of β-alanine (uM) produced/hr 1 Cell OD |
|---|---|---|---|
| 34 | 1.0 | 159.7 | 31.9 |
| 10 | 3.7 | 31.7 | 6.3 |

TABLE 1-continued

| Seq. ID No. | Harvest $OD_{600\,nm}$ t = 5 | uM β-alanine produced at t = 5/1 cell OD | Rate of β-alanine (uM) produced/hr 1 Cell OD |
|---|---|---|---|
| 38 | 4.0 | 54.9 | 11.0 |
| 20 | 3.0 | 73.4 | 14.7 |
| 14 | 3.7 | 33.5 | 7.7 |
| 22 | 2.2 | 4.8 | 1.0 |
| 42 | 5.0 | 17.5 | 3.5 |
| 26 | 3.7 | 23.9 | 4.8 |
| 18 | 4.7 | 19.3 | 3.9 |
| 44 | 2.9 | 64.4 | 12.9 |
| 51 | 3.7 | 35.0 | 7.0 |
| 36 | 3.0 | 29.8 | 6.0 |
| 48 | 1.1 | 110.1 | 22.0 |
| 12 | 4.7 | 17.8 | 3.6 |
| 4 | 3.7 | 22.4 | 4.5 |
| 16 | 1.0 | 136.0 | 19.4 |
| 24 | 1.4 | 94.7 | 18.9 |
| 46 | 1.7 | 107.6 | 20.7 |
| 28 | 1.5 | 148.0 | 29.2 |
| 40 | 1.4 | 14.6 | 2.9 |
| 32 | 1.6 | 93.2 | 13.6 |
| 2 | 1.5 | 87.5 | 17.5 |
| 30 | 2.7 | 72.6 | 14.3 |
| 6 | 1.7 | 125.7 | 23.0 |

Preferred AAM polypeptides of the present invention have an amino acid sequences of SEQ ID NOs: 2, 6, 12, 16, 20, 24, 28, 30, 32, 34, 38, 44, 46 or 48; more preferably they have an amino acid sequence of SEQ ID NOs: 6, 12, 28, 34, 46 or 48; most preferably, they have an amino acid sequence of SEQ ID NOs: 28 or 34.

The ultimate grandparent molecule is the KAM of *Bacillus subtilis*, which had no detectible AAM activity. The DNA encoding this grandparent molecule was modified as described in WO 03/062173, entitled "Alanine 2,3-aminomutase," to produce a polypeptide having a detectible alanine 2,3-aminomutase activity.

In the present application, the applicants utilized as one parent molecule a polynucleotide of SEQ ID NO: 58, which encoded the 471 residue polypeptide of SEQ ID NO: 59 and which exhibited an AAM activity of approximately 0.001 U/mg (units/mg of cell mass). The molecule of SEQ ID NO: 59 differs from the wild-type *B. subtilis* KAM (SEQ ID NO: 60), which had no detectible AAM activity, by having the following four (4) amino acid substitutions: L103M, M136V, Y140H and D339H.

Other grandparent molecules utilized as starting materials in the present invention were the DNA sequences from other microorganisms (e.g., *Porphyromonas gingivalis, Fusobacterium nucleatum*, and *Clostridium sticklandii*) that encoded a KAM polypeptide. These DNA sequences were modified using standard techniques to introduce point substitutions that ultimately produced a KAM polypeptide that also had a detectible cross-reactivity with α-alanine. One such parent molecule that was derived from *Porphyromonas gingivalis* is the polynucleotide of SEQ ID NO: 54 which encodes the 416 residue polypeptide of SEQ ID NO: 55. The parental polypeptide of SEQ ID NO: 55 differs from the wild-type *Porphyromonas gingivalis* KAM by having the following seven (7) amino acid substitutions: N19Y, E30K, L53P, H85Q, I192V, D331G, and M342T. Another such parent molecule that was derived from *F. nucleatum* is the polynucleotide of SEQ ID NO: 56 which encodes the 425 residue polypeptide of SEQ ID NO: 57.

Yet another parent polynucleotide was derived by modification of the polynucleotide in *C. stricklandii* that encodes KAM. The resulting parental polynucleotide, which has a detectable cross-reactivity with α-alanine, is the polynucleotide of SEQ ID NO: 52 which encodes the 416 residue polypeptide of SEQ ID NO: 53.

The above described parental polypeptides of SEQ ID NOs: 53, 55, 57 and 58 are compared in the alignment chart of FIG. 4. From the alignment chart, it can be seen that the KAMs from *P. gingivalis, C. stricklandii*, and *F. nucleatum* are truncated at the N-terminus and at the C-terminus relative to the KAM from *B. subtilis*, while between the four species, about 40% of the residue positions in the central portion of the KAM polypeptide are conserved. Based upon the truncated species in the alignment chart of FIG. 4, it can be inferred that the first 8 amino acid residues at the N-terminus of SEQ ID NO: 58 and the last 40 residues at the C-terminus of SEQ ID NO: 58 are not necessary for KAM activity, or the AAM activity that is derived therefrom. In FIG. 4, there is also provided a consensus sequence.

The AAM polypeptide molecules of the present invention with their enhanced AAM activity were made by applying directed evolution techniques to the above-described parental molecules. These techniques are described in further detail herein.

In yet another aspect, the present invention is directed to AAM polypeptides that have enhanced activity in coupled reactions.

In another embodiment, the present invention is directed to an AAM a polypeptide encoded by a nucleic acid sequence which hybridizes under high stringency conditions with either (i) the nucleotide sequence of SEQ ID NO: 1, 3, 5, 7, 9, 11, 13, 15, 17, 19, 21, 23, 25, 27, 29, 31, 33, 35, 37, 41, 43, 45, 47 or 49; (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.). For polynucleotides of at least 100 nucleotides in length, low to very high stringency conditions are defined as prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures.

For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

In another embodiment, the present invention is directed to a variant of the polypeptide of (d) comprising a substitution, deletion, and/or insertion of one to six amino acids there-from and having AAM activity from about 1 to about 30 μM β-alanine produced/hour 1 cell OD at pH 7.0-7.6, 25° C., such as determined by the method of Example 8. Preferably, amino acid changes are of a minor nature, that is conservative amino acid substitutions that do not significantly affect the folding and/or activity of the protein; small deletions, typically of one to six amino acids; small amino- or carboxyl-terminal extensions; a small linker peptide; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions, which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In another embodiment, the present invention is directed to a fragment of (a), (b) or (c), as described above in the first paragraph of the Detailed Description, that has from about 1 to about 30 μM β-alanine produced/hour 1 cell OD at pH 7.0-7.6, 25° C., such as determined by the method of Example 8. By the term "fragment" is meant that the polypeptide has a deletion of 1 to 8 amino acid residues from the N-terminus or 1-40 residues from the C-terminus, or both. Preferably, the deletion is 1 to 20 residues from the C-terminus, more preferably, the deletion is 1 to 10 residues from the C-terminus.

Polynucleotides

In its second aspect, the present invention is directed to a polynucleotide sequence that encodes for an AAM polypeptide of the present invention. Given the degeneracy of the genetic code, the present invention is also directed to any polynucleotide that encodes for the above referenced AAM polypeptides of the present invention. In its second aspect, the present invention is directed to a polynucleotide sequence that encodes for the correspondingly referenced AAM polypeptide. Given the degeneracy of the genetic code, the present invention is also directed to any polynucleotide that encodes for the above referenced AAM polypeptides of the present invention. In a preferred embodiment, the present invention is directed to certain specific polynucleotides of SEQ ID NOS: 1, 3, 5, 7, 9, 11, 13, 15, 17, 19, 21, 23, 25, 27, 29, 31, 33, 35, 37, 39, 41, 43, 45, 47 and 49 that encode for the novel AAM polypeptides of SEQ ID NOS: 2, 4, 6, 8, 10, 12, 14, 16, 18, 20, 22, 24, 26, 28, 30, 32, 34, 36, 38, 40, 42, 44, 46, 48 and 51, respectively. Preferred polynucleotides encode for a polypeptide of SEQ ID NO: 2, 6, 12, 16, 20, 24, 28, 30, 32, 34, 38, 44, 46 or 48; more preferably they encode a polypeptide of SEQ ID NO: 6, 12, 28, 34, 46 or 48; most preferably, they have a polypeptide of sequence of SEQ ID NO: 28 or 34.

To make the improved AAM polypeptides of the present invention, one starts with one or more wild-type polynucleotides that encode a KAM polypeptide. The term "wild-type" polynucleotide means that the nucleic acid fragment does not comprise any mutations from the form isolated from nature. The term "wild-type" protein means that the protein will be active at a level of activity found in nature and typically will comprise the amino acid sequence as found in nature. Thus, the term "wild type" or "grand-parent sequence" indicates a starting or reference sequence prior to a manipulation of the invention.

Suitable sources of wild-type KAM as a starting material to be improved is readily identified by screening genomic libraries for the KAM activity. A particularly suitable source of KAM is the yodO gene of *Bacillus* sp. bacteria as found in nature. Using the published KAM gene sequences for *B. subtilis* (e.g. WO 03 0623173 A2), primers for amplification of the genes from their respective gene libraries were created using conventional techniques. One such technique for isolating the KAM of *B. subtilis* is disclosed in Chen et al., "A novel lysine 2,3-aminomutase encoded by the yodO gene of *Bacillus subtilis*: characterization on observation of organic radical intermediates," Biochem J. 348:539-549 (2000), which is incorporated herein by reference.

The starting polynucleotides of SEQ ID NOs: 52, 54, 56 and 58 were obtained using the techniques discloses in WO 03 0623173 A2 which is incorporated herein by reference for the disclosure of those techniques as recited in the examples therein. Specifically, WO 03 0623173 A2 discloses a *B. subtilis* wild-type lysine 2,3-aminomutase (KAM), and a mutated form thereof, which encodes an alanine 2,3-aminomutase (AAM). In addition, WO 03 0623173 A2 also discloses a *P. gingivalis* wild-type lysine 2,3-aminomutase (KAM) and a mutated form thereof, which encodes an alanine 2,3-aminomutase (AAM).

Beginning with the polynucleotide of SEQ ID NO: 58, a non-naturally occurring and mutated and/or evolved enzyme, having unknown AAM activity is generated using any one of the well-known mutagenesis or directed evolution methods. See, e.g., Ling, et al., "Approaches to DNA mutagenesis: an overview," *Anal. Biochem.,* 254(2):157-78 (1997); Dale, et al., "Oligonucleotide-directed random mutagenesis using the phosphorothioate method," *Methods Mol. Biol.,* 57:369-74 (1996); Smith, "In vitro mutagenesis," *Ann. Rev. Genet.,* 19:423-462 (1985); Botstein, et al., "Strategies and applications of in vitro mutagenesis," *Science,* 229:1193-1201 (1985); Carter, "Site-directed mutagenesis," *Biochem. J.,* 237:1-7 (1986); Kramer, et al., "Point Mismatch Repair," *Cell,* 38:879-887 (1984); Wells, et al., "Cassette mutagenesis: an efficient method for generation of multiple mutations at defined sites," *Gene,* 34:315-323 (1985); Minshull, et al., "Protein evolution by molecular breeding," *Current Opinion in Chemical Biology,* 3:284-290 (1999); Christians, et al., "Directed evolution of thymidine kinase for AZT phosphorylation using DNA family shuffling," *Nature Biotechnology,* 17:259-264 (1999); Crameri, et al., "DNA shuffling of a family of genes from diverse species accelerates directed evolution," *Nature,* 391:288-291; Crameri, et al., "Molecular evolution of an arsenate detoxification pathway by DNA shuffling," *Nature Biotechnology,* 15:436-438 (1997); Zhang, et al., "Directed evolution of an effective fucosidase from a galactosidase by DNA shuffling and screening," *Proceedings of the National Academy of Sciences, U.S.A.,* 94:454-4509; Crameri, et al., "Improved green fluorescent protein by molecular evolution using DNA shuffling," *Nature Biotechnology*<14:315-319 (1996); Stemmer, "Rapid evolution of a protein in vitro by DNA shuffling," *Nature,* 370:389-391 (1994); Stemmer, "DNA shuffling by random fragmentation and reassembly: In vitro recombination for molecular evolution," *Proceedings of the National Academy of Sciences, U.S.A.,* 91:10747-10751 (1994); WO 95/22625; WO 97/0078; WO 97/35966; WO 98/27230; WO 00/42651; WO 01/75767 and U.S. Pat. No. 6,537,746 which issued to Arnold, et al. on Mar. 25, 2003 and is entitled "Method for creating polynucleotide and polypeptide sequences."

Any of these methods can be applied to generate AAM polynucleotides. To maximize any diversity, several of the above-described techniques can be used sequentially. Typically, a library of shuffled polynucleotides is created by one mutagenic or evolutionary technique and their expression products are screened to find the polypeptides having the highest AAM activity. Then, a second mutagenic or evolutionary technique is applied to polynucleotides encoding the most active polypeptides to create a second library, which in turn is screened for AAM activity by the same technique. The process of mutating and screening can be repeated as many times as needed, including the insertion of point mutations, to arrive at a polynucleotide that encodes a polypeptide with the desired activity, thermostability, or cofactor preference.

Alternatively, polynucleotides and oligonucleotides of the invention can be prepared by standard solid-phase methods, according to known synthetic methods. Typically, fragments of up to about 100 bases are individually synthesized, then joined (e.g., by enzymatic or chemical litigation methods, or polymerase mediated methods) to form essentially any desired continuous sequence. For example, polynucleotides and oligonucleotides of the invention can be prepared by chemical synthesis using, e.g., the classical phosphoramidite method described by Beaucage et al. (1981) *Tetrahedron Letters* 22:1859-69, or the method described by Matthles et al. (1984) EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company, Midland, Tex., The Great American Gene Company, Ramona, Calif., ExpressGen Inc., Chicago, Ill., Operon Technologies Inc., Alameda, Calif., all of which have internet web sites, and many others. Similarly, peptides and antibodies can be custom ordered from any of a variety of sources, such as PeptidoGenic, HTI Bio-products, Inc., BMA Biomedicals Ltd. (U.K.), Bio. Synthesis, Inc., and many others.

Polynucleotides may also be synthesized by well-known techniques as described in the technical literature. See, e.g., Carruthers et al., *Cold Spring Harbor Symp. Quant. Biol.* 47:411-418 (1982), and Adams et al., *J. Am. Chem. Sec.* 105:661 (1983). Double stranded DNA fragments may then be obtained either by synthesizing the complementary strand and annealing the strands together under appropriate conditions, or by adding the complementary strand using DNA polymerase with an appropriate primer sequence.

General texts which describe molecular biological techniques useful herein, including mutagenesis, include Berger and Kimmel, *Guide to Molecular Cloning Techniques, Methods in Enzymology*, volume 152 Academic Press, Inc., San Diego, Calif. ("Berger"); Sambrook et al., *Molecular Cloning—A Laboratory Manual* (2nd Ed.), volumes 1-3, Cold Spring Harbor Laboratory, Cold Spring Harbor, N.Y., 1989 ("Sambrook"); and *Current Protocols in Molecular Biology*, F. M. Ausubel et al., eds., Current Protocols, a joint venture between Greene Publishing Associates, Inc. and John Wiley & Sons, Inc. (supplemented through 2000) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202*; PCR Protocols A Guided to Methods and Applications* (Innis et al., eds.) Academic Press Inc. San Diego, Calif. (1990); Arnheim & Levinson (Oct. 1, 1990) *Chemical and Engineering News* 36-47*; The Journal Of NIH Research* (1991) 3:81-94; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al., (1988) *Science* 241:1077-1080; Van Brunt (1990) *Biotechnology* 8:291-294; Wu and Wallace, (1989) *Gene* 4:560; Barringer et al. (1990) *Gene* 89:117, and Sooknanan and Malek (1995) *Biotechnology* 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369:684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

It will be appreciated by those skilled in the art due to the degeneracy of the genetic code, a multitude of nucleotide sequences encoding AAM polypeptides of the invention may be produced, some of which bear substantial identity to the nucleic acid sequences explicitly disclosed herein. It is also within the scope of the present invention that the polynucleotides encoding the AAM polypeptides of the present invention may be codon optimized for optimal production from the host organism selected for expression. Those having ordinary skill in the art will recognize that tables and other references providing codon preference information for a wide range of organisms are readily available. See e.g., Henaut and Danchin, "*Escherichia coli* and *Salmonella*," Neidhardt, et al. Eds., ASM Press, Washington D.C., p. 2047-2066 (1996).

It is to be noted that expression in *E. coli* is different than in other organisms. For example, in the present invention, the codon (tgg) encodes Trp (W) for residue position 31 in the parent polypeptide of SEQ ID NO: 59. However, the corresponding codon for residue position 31 is "tga" in each of the progeny polynucleotides of SEQ ID NOs: 1, 3, 5, 7, 9, 11, 13, 15, 17, 19, 21, 23, 25, 27, 29, 31, 33, 35, 37, 39, 41, 43, 45, and 47 encoding for the AAM polypeptides of SEQ ID NOs: 2, 4, 6, 8, 10, 12, 14, 16, 18, 20, 22, 24, 26, 28, 30, 32, 34, 36, 38, 40, 42, 44, 46, and 48, respectively. One skilled in the art recognizes that the codon "tga" is usually a stop (nonsense) codon. However, in the present expression system used in the ΔpanD *E. coli* strain, and under the selection conditions imposed, this codon is read through by the *E. coli* as a sense codon and is expressed, presumably as Trp (W). Others have reported that "tga" is the weakest stop codon for *E. coli* and that it is often read through as a sense codon for Trp (W) in high expression. See e.g., Parker, J., "Errors and Alternatives in Reading the universal Genetic Code," Microbiological Reviews, 53(3): 273-298 (1989); Roth, J., "UGA Nonsense Mutations in *Salmonella typhimurium*," J. of Bacteriology, 102(2):467-475 (1970); and McBeath, G. and Kast, P., "UGA Read-Through Artifacts—When Popular Gene Expression Systems Need a Patch," BioTechniques, 24:789-794 (May 1998), which are incorporated herein by reference. Hence for expression in non-*E. coli* systems, it would be advantageous to alter the codon (tga) at residue position 31 to "tgg" which is the universal sense codon for Trp (W).

In SEQ ID NO: 49, the codon encoding for residue 72 is "tag" which is read as a stop codon. However, two fragments are produced. The first fragment, having residues 1-71 of SEQ ID NO: 50, does not have any detectable AAM activity. The second fragment that is produced begins with residue 73 (Val) instead of the usual Met. This second fragment has 399 residues (SEQ ID NO: 51) and does have significant AAM activity (see Table 2) based upon the assay of Example 8. Thus, the first 72 residues at the N-terminus of the AAM polypeptide (based upon the consensus sequence or the parental KAM sequence from *B. subtilis*) are not absolutely necessary for AAM activity.

In the present case, several round No. 1 libraries were created by applying a variety of mutagenic techniques to the polynucleotides of SEQ ID NOs: 52, 54, 56 and 58.

In its third aspect, the present invention is directed to an expression vector and to a host cell comprising a polynucleotide of the present invention operatively linked to a control sequence. To obtain expression of the variant gene encoding an AAM polypeptide, the variant gene was first operatively linked to one or more heterologous regulatory sequences that control gene expression to create a nucleic acid construct, such as an expression vector or expression cassette. Thereafter, the resulting nucleic acid construct, such as an expression vector or expression cassette, was inserted into an appropriate host cell for ultimate expression of the AAM polypeptide encoded by the shuffled gene. A "nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. Thus, in one aspect, the present invention is directed to a nucleic acid construct comprising a polynucleotide encoding an AAM polypeptide of the present invention.

The term "nucleic acid construct" is synonymous with the term "expression cassette" when the nucleic acid construct contains all the control sequences required for expression of a coding sequence of the present invention. The term "coding sequence" is defined herein as a nucleic acid sequence, which directly specifies the amino acid sequence of its protein product. A coding sequence can include, but is not limited to, DNA, cDNA, and recombinant nucleic acid sequences.

An isolated polynucleotide encoding an AAM polypeptide of the present invention may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

The term "control sequence" is defined herein to include all components, which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence. The "promoter sequence" is a relatively short nucleic acid sequence that is recognized by a host cell for expression of the longer coding region that follows. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

For bacterial host cells, suitable promoters for directing the transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

For filamentous fungal host cells, suitable promoters for directing the transcription of the nucleic acid constructs of the present invention include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the host cell of choice, may be used in the present invention.

Preferred terminators for filamentous fungal host cells are obtained from the genes for *Aspergillus oryzae* TAKA amylase, *Aspergillus niger* glucoamylase; *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention. Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence that is functional in the host cell of choice may be used in the present invention. Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region that directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the AAM polypeptide of the present invention would be operably linked with the regulatory sequence.

Expression Vectors

In another aspect, the present invention is also directed to a recombinant expression vector comprising a polynucleotide of the present invention (which encodes an AAM polypeptide of the present invention), and one or more expression regulating regions. An expression regulating region includes a promoter, a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any sector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that, exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

The vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A, pSC101, pMB1 and ColE1. Origins of replication of plasmids pBR322 (which has a pMB1 origin of replication) pUC19 (which has a ColE1 origin of replication), pACYC177 and pACYC184 (which have a P15A origin of replication), permit replication in *E. coli*; origins of replication for plasmids pUB110, pE194, pTA1060, or pAM.beta.1 permit replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent The procedures used to ligate the elements described above to construct the recombinant nucleic acid construct and expression vectors of the present invention are well known to one skilled in the art (see, e.g., J. Sambrook, E. F. Fritsch, and T. Maniatis, 1989, Molecular Cloning, A Laboratory Manual, 2d edition, Cold Spring Harbor, N.Y.).

Many of the expression vectors for use in the present invention are commercially available. Suitable commercial expression vectors include p3xFLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids that are derived front pBR322 (Gibco BRL), pUC (Gibco BRL), pREP4, pCEP4 (Invitrogene) or pPoly (Lathe et al., 1987, Gene 57, 193-201).

Figure 3:
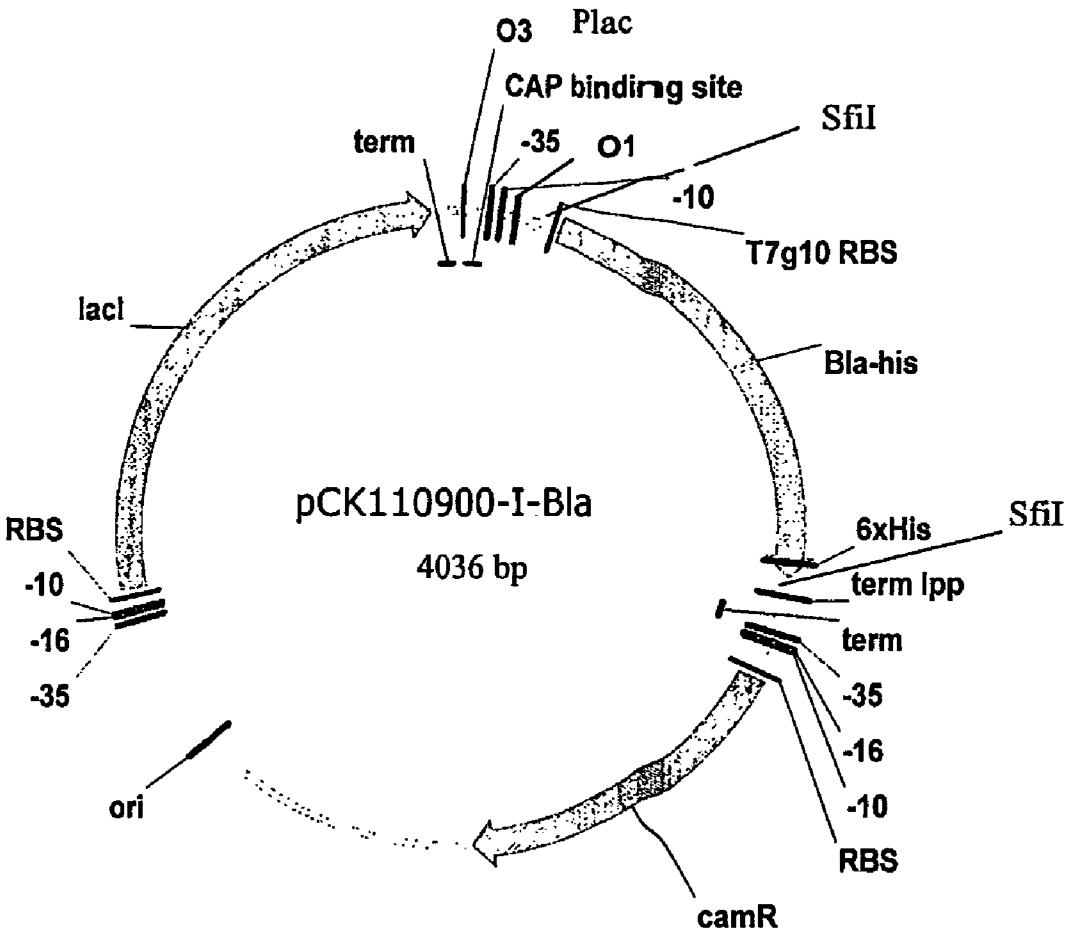
FIG. 3 is a 4036 bp expression vector (pCK110900-I Bla) of the present invention comprising a P15A origin of replication (P15A ori), a lacI repressor, a CAP binding site, a lac promoter (lac), a T7 ribosomal binding site (T7g10 RBS), and a chloramphenicol resistance gene (camR).

Example 6 herein discloses the use of the expression vector pCK110900-I Bla, as shown in the vector map of FIG. 3.

Host Cells

Host cells for use in expressing the expression vectors of the present invention include but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are well known in the art.

By way of example, *Escherichia coli* W3110 was transformed by an expression vector for expressing the shuffled genes of the present invention. The expression vector was created by operatively linking a variant gene of the present invention to the lac promoter under control of the lacI repressor gene. The expression vector also contained the P15A origin of replication and the chloroamphenicol resistance gene. The transformed *Escherichia coli* W3110 was cultured under appropriate culture medium containing chloramphenicol such that only transformed E coli cells that expressed the expression vector survived. See e.g., Example 1.

Purification

Once the AAM polypeptides were expressed by the variant genes in *E. coli*, the polypeptides were purified from the cells and or the culture medium using any one or more of the well known techniques for protein purification, including lysozyme treatment, sonication, filtration, salting, ultra-centrifugation, affinity chromatography, and the like under strict anoxic conditions. Suitable solutions for high efficiency extraction of proteins from bacteria, such as *E. coli*, are commercially available under the trade name CelLytic B™ from Sigma-Aldrich of St. Louis Mo. A suitable process for purifying AAM polypeptides sufficiently from cell lysate for applications in a chemical process is disclosed in the references: Chirpich, T. P. et al., J. Biol. Chem., 1970, 245, 1778-1789; and Petrovich, R. M. et al., J. Biol. Chem., 1991, 266, 7656-7660, both of which are incorporated herein by reference.

Screening

After several rounds of directed evolution were performed, the resulting libraries of exemplary AAM polypeptides were screened. Screening for transformed cells that express a polypeptide having AAM activity is, in general, a two-step process. First, one physically separates the cells and then determines which cells do and do not possess a desired property. Selection is a form of screening in which identification and physical separation are achieved simultaneously by expression of a selection marker, which, in some genetic circumstances, allows cells expressing the marker to survive while other cells die (or vice versa). Exemplary screening markers include luciferase, β-galactosidase, and green fluorescent protein. Selection markers include drug and toxin resistance genes, such as resistance to chloramphenicol, ampicillin and the like. Although spontaneous selection can and does occur in the course of natural evolution, in the present methods selection is performed by man.

The AAM polynucleotides generated by the mutagenesis or directed evolution method are screened in accordance with the protocol described in Example 8 to identify those having enhanced activity that are suitable for inclusion as an improved AAM polypeptide of the present invention. In the process of Example 8, the screening of clones from the expression libraries for enhanced AAM activity was performed by measuring the conversion of α-alanine to β-alanine using liquid chromatography and mass spectrometry. Based upon the screening results, the AAM polypeptides of the present invention axe listed in Table 2 below along with their residue changes and enhanced AAM activity relative to one parental AAM polypeptide, i.e., the polypeptide of SEQ ID NO: 59.

TABLE 2

| Seq. ID No. | Residue changes relative to parent SEQ ID NO: 59 | Rate of β-alanine (uM) produced/hr 1 Cell OD |
|---|---|---|
| 34 | I177L, I227M, G308R, I408L, F416S, D447G | 31.9 |
| 10 | I298V, G308R, F416S, D447G | 6.3 |
| 38 | D125N, I177L, T210S, | 11.0 |
| 20 | K2E, I3O7L, | 14.7 |
| 14 | K13E, L17R, L197P, I200T, M281V, F310S, F416S, D447G | 7.7 |
| 22 | Y72H, L118P, R145L, I220V, F240L, S250P, R311C, F416S, D447G | 1.0 |
| 42 | K19R, T99S, G308R, F416S, D447G | 3.5 |
| 26 | N80K, G308R, E319G, R325G, Q350R | 4.8 |
| 18 | Q32R, S74P, S113T, L118P, G308R, F416S, D447G | 3.9 |
| 44 | D79E, G308R, S329P, F393S, F414S, D445G, L453S, | 12.9 |
| 51 (fragment) | A73V, G308R, Y331N, F416S, D447G | 7.0 |
| 36 | D79E, S93P, N132D, M281I, G308R, Y331N, F416S, D447G | 6.0 |
| 48 | K2E, M76I, D79E, T131A, L203P, G308R, Y331C, F416S, D447G | 22.0 |
| 12 | R38G, C134G, C141R, L203P, I280T, G308R, F416S, D447G | 3.6 |
| 4 | 2KE, I220V, N237D, G308R, D360G, K361R, F416S, D447G | 4.5 |
| 16 | K13E, L17R, L197P, I200T, M281V, G308R, F310S, F416S, D447G | 19.4 |
| 24 | E23D, L43S, D124G, Y137H, K156E, G308R, D411G, F416S, D447G | 18.9 |
| 46 | W18R, M76I, D79E, V90A, M152T, I163T, S178P, V215G, G308R, V354A, F416S, D447G | 20.7 |

TABLE 2-continued

| Seq. ID No. | Residue changes relative to parent SEQ ID NO: 59 | Rate of β-alanine (uM) produced/hr 1 Cell OD |
|---|---|---|
| 28 | E22G, Y71C, S74P, H108R, D187G, I244V, G308R, E396G, F416S, D447G, F454S | 29.2 |
| 40 | Y137H, G308R, D411G, F416S, D422V, D447G | 2.9 |
| 32 | H35R, D79E, K98T, T99S, N132S, S135P, E204G, K230R, G308R, F416S, D447G | 13.6 |
| 2 | W235R, S250P, C254R, D276G, G308R, Y380C, I381T, F416S, K440E, D447G | 17.5 |
| 30 | Q32R, N67S, H140R, G308R, F416S, D447G | 14.3 |
| 6 | E24G, M96I, E109G, G308R, F416S, D447G | 23.0 |
| 8 | G308R, S329P, F416S, D447G, L455S | 14.7 |

In Table 2 above, it is seen that the AAM polypeptides of the present invention have from 2 to 11 residue differences than their parent polypeptide of SEQ ID NO: 59, and very significant AAM activity as evidenced by the production of β-alanine in the assay of Example 8. In comparison, β-alanine was not detected for SEQ ID NO: 59 under the assay conditions used to test the AAM variants. However, some β-alanine production for parental SEQ ID NO: 59 was detected in a qualitative growth based complementation assay.

Referring to Table 2 above, two preferred residue changes for the AMM polypeptides of the present invention relative to the parental sequence of SEQ ID NO: 59 are G308R and F416S. In those AAM polypeptides of the present invention that are at least 447 residues long, an additional preferred residue change is D447G relative to the parental sequence of SEQ ID NO: 59. Additional suitable residue changes are G308K, F416M and D447L, A, I or V. Thus, in one aspect, the present invention is directed to an AAM polypeptide having at least 5 amino acid residue changes, typically 5-11 residue changes, relative to SEQ ID NO: 59 or a truncated fragment thereof as taught herein, the residue changes including from 1 to 3 residue changes selected from the group consisting of G308R, G308K, F416S, F416M, D447G, D447L, D447A, D447I and D447V.

Based upon the AAM activity in Table 2, an especially preferred AAM polypeptide of the present invention is a polypeptide having 95% sequence homology with the polypeptide of SEQ ID NO: 34, more preferably 98% homology, most preferably 99% homology.

The parental polypeptides of SEQ ID NOs: 53, 55 and 57 demonstrate that the residues 1-8 at the N-terminus and residues 434-473 at the C-terminus are not necessary for KAM or AAM activity. Likewise, the polypeptide fragment of SEQ ID NO: 51, which is a 399 residue expression product, discloses that the first 72 amino acids at the N-terminus relative to the parental clone of SEQ ID NO: 59 are not necessary for AAM activity. (See Table 2) Thus, it is also within the scope of the present invention that the polypeptides described herein include fragments thereof that lack from 1 to 72 residues from their N-terminus relative to the parental sequence of SEQ ID NO: 59, typically from 1 to 40 residues, more typically from 1-20 residues, most typically from 1 to 11 residues. It is also within the scope of the present invention that the above described N-terminal truncation be utilized in combination with a C-terminal truncation as described elsewhere herein.

Only a very few (≦0.5%) of the mutations to the parental *B. subtilis* KAM (SEQ ID NO: 59) backbone were found to be beneficial. Specifically, for every 1000 clones screened, there occurred only 3-5 single point or double point mutations that were beneficial. In fact, some of the mutations were found to be detrimental.

The first of the following two sets of sequences provides the sequence of the wild type *B. subtilis* lysine 2,3-aminomutase (KAM) polypeptides of the prior art, as deposited (GI_ 2529467_GB_AAB81159.1_). This sequence (SEQ ID NO: 60) was not used as a parent sequence but is provided only for purposes of comparison.

M K N K W Y K P K R H W K E I E L W K D V P E E K W N D W L W Q L T H T (SEQ ID NO: 60)

V R T L D D L K K V I N L T E D E E E G V R I S T K T I P L N I T P Y Y A S L

M D P D N P R C P V R M Q S V P L S E E M H K T K Y D L E D P L H E D E D

S R V P G L T H R Y P D R V L F L V T N Q C S M Y C R Y C T R R R F S G Q I

G M G V P K K Q L D A A I A Y I R E T P E I R D C L I S G G D G L L I N D Q I

L E Y I L K E L R S I P H L E V I R I G T R A P V V F P Q R I T D H L C E I L K

K Y H P V W L N T H F N T S I E M T E E S V E A C E K L V N A G V P V G N

Q A V V L A G I N D S V P I M K K L M H D L V K I R V R P Y Y I Y Q C D L S

E G I G H F R A P V S K G L E I I E G L R G H T S G Y A V P T F V V D A P G G

G G K I A L Q P N Y V L S Q S P D K V I L R N F E G V I T S Y P E P E N Y I P

N Q A D A Y F E S V F P E T A D K K E P I G L S A I F A D K E V S F T P E N V

D R I K R R E A Y I A N P E H E T L K D R R E R R D Q L K E K K F L A Q Q K

K Q K E T E C G G D S S

The second sequence in the set indicates the diversity of the AAM polypeptides of the present invention relative to the known wild-type *B. subtilis* KAM sequence by designating with the letter "S" followed by the residue number those residues in the Applicants' AAM polypeptides that differ from those of wild-type *B. subtilis* KAM sequence:

The diversity of changes at various residue positions for the AAM polypeptides of the present invention are shown to the right of the arrow in Table 2 below and relative amino acid residues of wild-type KAM of *B. subtilis* (GI_ 2529467_GB_AAB81159.1_) (SEQ ID NO: 60) which are shown to the left of the arrow:

M $X_{2}$ N K W Y K P K R H W $X_{13}$ E I E $X_{17}$ W $X_{19}$ D V P $X_{23}$ $X_{24}$ K W N D W L W (SEQ ID NO: 65)

$X_{32}$ L T $X_{35}$ T V $X_{38}$ T L D D $X_{43}$ K K V I N L T E D E E E G V R I S T K T I P L $X_{67}$ I T P $X_{71}$ $X_{72}$ $X_{73}$ $X_{74}$ L M D P $X_{79}$ $X_{80}$ P R C P V R M Q S V P L $X_{93}$ E E $X_{96}$ H $X_{98}$ $X_{99}$ K Y D L E D P L $X_{108}$ $X_{109}$ D E D S $X_{114}$ V P G $X_{115}$ T H R Y P $X_{124}$ R V L F

L V T $X_{132}$ Q $X_{134}$ $X_{135}$ $X_{136}$ $X_{137}$ C R $X_{140}$ $X_{141}$ T R R $X_{145}$ F S G Q I G M G V P $X_{156}$ K Q L D A A I A Y I R E T P E I R D C L I S G G D G L L I N $X_{187}$ Q I L E Y I

L K E $X_{197}$ R S $X_{200}$ P H $X_{203}$ $X_{204}$ V I R I G T R A P V V F P Q R I T D H $X_{224}$ C E I

L K $X_{230}$ $X_{231}$ H P V $X_{235}$ L $X_{237}$ T H $X_{240}$ N T S I E M T E E $X_{250}$ V E A $X_{254}$ E K L

V N A G V P V G N Q A V V L A G I N $X_{276}$ S V P $X_{280}$ $X_{281}$ K K L M H D L V K I

R V R P Y Y I Y Q C D L S E G $X_{307}$ $X_{308}$ H $X_{310}$ $X_{311}$ A P V S K G L $X_{319}$ I I E G L

R G H T $X_{329}$ G $X_{331}$ A V P T F V V $X_{339}$ A P G G G G K I A L $X_{350}$ P N Y V L S Q

S P $X_{360}$ K V I L R N F E G V I T S Y P E P E N $X_{380}$ $X_{381}$ P N Q A D A Y F E S V $X_{393}$ P $X_{395}$ T A D K K E P I G L S A $X_{408}$ F A $X_{411}$ K E V S $X_{416}$ T P E N V $X_{422}$ R I

K R R E A Y I A N P E H E T L $X_{400}$ D R R E $X_{445}$ R $X_{447}$ Q L K E K K $X_{454}$ $X_{455}$ A

Q Q K K Q K E T E C G G D S S

TABLE 3

| | |
|---|---|
| $X_2$: | K→E |
| $X_{13}$: | K→E |
| $X_{17}$: | L→R |
| $X_{19}$: | K→R |
| $X_{23}$: | E→D, G |
| $X_{24}$: | E→G |
| $X_{32}$: | Q→R |
| $X_{35}$: | H→R |
| $X_{38}$: | R→G |
| $X_{43}$: | L→S |
| $X_{67}$: | N→S |
| $X_{71}$: | Y→C |
| $X_{72}$: | Y→H, W |
| $X_{73}$: | A→V |
| $X_{74}$: | S→P |
| $X_{79}$: | D→G |
| $X_{80}$: | N→K |
| $X_{93}$: | S→P |
| $X_{96}$: | M→I |
| $X_{98}$: | K→T |
| $X_{99}$: | T→S |
| $X_{108}$: | H→R |
| $X_{109}$: | E→G |
| $X_{114}$: | R→P |
| $X_{118}$: | L→P |
| $X_{124}$: | D→N |
| $X_{132}$: | N→D, S |
| $X_{134}$: | C→G |
| $X_{135}$: | S→P |
| $X_{136}$: | M→V |
| $X_{137}$: | Y→H |
| $X_{140}$: | Y→H |
| $X_{141}$: | C→R |
| $X_{145}$: | R→L |
| $X_{156}$: | K→E |
| $X_{187}$: | D→G |
| $X_{197}$: | L→P |
| $X_{200}$: | I→T |
| $X_{203}$: | L→P |
| $X_{204}$: | E→G |
| $X_{224}$: | L→P |
| $X_{230}$: | K→R |
| $X_{231}$: | Y→H |
| $X_{235}$: | W→R |
| $X_{237}$: | N→D |
| $X_{240}$: | F→L |
| $X_{250}$: | S→P |
| $X_{254}$: | C→Y, R |
| $X_{276}$: | D→G |
| $X_{280}$: | I→T |
| $X_{281}$: | M→I, V |
| $X_{307}$: | I→L |
| $X_{308}$: | G→R |
| $X_{310}$: | F→S |
| $X_{311}$: | R→C |
| $X_{319}$: | E→G |
| $X_{329}$: | S→P |
| $X_{331}$: | Y→N |
| $X_{339}$: | D→H |
| $X_{350}$: | Q→R |
| $X_{360}$: | D→G |
| $X_{361}$: | K→R |
| $X_{380}$: | Y→C |
| $X_{381}$: | I→T |
| $X_{393}$: | F→S |
| $X_{395}$: | E→G |
| $X_{408}$: | I→L |
| $X_{411}$: | D→G |
| $X_{416}$: | F→S |
| $X_{422}$: | D→V |
| $X_{440}$: | K→E |
| $X_{445}$: | R→K |
| $X_{447}$: | D→G |
| $X_{454}$: | F→S |
| $X_{455}$: | L→S |

In a fourth aspect, the present invention is directed to a method of making an AAM a nucleic polypeptide of the present invention comprising (a) cultivating a host cell transformed with a nucleic acid sequence encoding an AAM polypeptide of the present invention under conditions suitable for production of the polypeptide; and (b) providing glucose to the cultivated host cells under conditions suitable for the production of β-alanine. The β-alanine may be optionally recovered from the cells.

EXAMPLE 1

Transformation Protocol for aam Libraries/ΔpanD Strain

A mutant *E. coli* strain—ΔpanD, derived from BW25113 which is described in Datsenko, K. A. and Wanner, B. L., Proc. Natl. Acad. Sci. USA 97:6640-6645 (2000) was used as the host strain for screening of the aam gene libraries. The protocol used to make the deletion is detailed in Example 4 of Cargill patent application WO 03/062173.

Chemical competent *E. coli* ΔpanD was removed from −80° C. frozen storage and thawed. Thereafter, it was kept on ice until used. An aliquot (100 μl per transformation) was transferred into a sterile 1.5 ml centrifuge tube. A KCM (5×) salt solution was added until the concentration in the aliquot was 1×. KCM consists of 700 mM KCl; 10 mM morpholinopropanesulphonic acid (MOPS) adjusted to pH 5.8. 1-5 μl of the ligation mixture was added to the cells. The cells containing the ligation mixture were first incubated on ice for 30 minutes. The cells were heat shocked at 42° C. for 1 min, and subsequently incubated on ice for 2 minutes. 500 μl of SOC (Maniatis, T., Fritsch, E. F., and Sambrook J. (1982) Molecular Cloning: A Laboratory Manual, 1st Ed., pp. A.2 and A.3, Cold Spring Harbor Laboratory, Cold Spring Harbor, N.Y.) was added to the cells, and the cells were incubated at 37° C. for 1 hour with agitation. The cells were then centrifuged at 5000 rpm for 3 minutes, and the SOC was removed. The cell pellet was re-suspended in 500 μl of M9 selection medium ((Maniatis, T., Fritsch, E. F., and Sambrook, J. (1982) Molecular Cloning: A Laboratory Manual, 1st Ed., pp. A.2 and A.3, Cold Spring Harbor Laboratory, Cold Spring Harbor, N.Y.) and incubated at 30-C for 2-4 hours with agitation. The cells were then plated onto M9 minimal agar medium supplemented with 1% mannose, 20 μM iron citrate, 5.0 g/l α-alanine, 0.1 mM isopropyl-β-D-thiogalactoside (IPTG) (Sigma Chemical Corp., St. Louis, Mo.), 50 mM MOPS, 25 mM bicarbonate, and 30 μg/ml chloramphenicol. The plated cells were incubated at 30° C. for 3 days or until colonies were of sufficient size to be picked using the Q-BOT™ robot colony picker (Genetix USA, Inc, Boston Mass.).

In Round 2 of the transformation, the above procedure was followed except that the incubation temperature of the last two incubations in the procedure was increased to 37° C., and M9 minimal selection medium was not supplemented with α-alanine (0 g/L α-alanine).

A. Alternate Transformation Protocol for aam Libraries/ΔpanD KIfldA Strain

A mutant *E. coli* strain ΔpanD, derived from BW25113 which is described in Datsenko, K. A. and Wanner, B. L., Proc. Natl. Acad. Sci. USA 97:6640-6645 (2000) is used as the host strain for screening of the aam gene libraries. The protocol used to make the deletion is detailed in Example 4 of International patent publication WO 03/062173. Optimally, a strain additionally having an increased expression of the flavodoxin (fldA) gene was used as the host strain for screening of the aam gene libraries, since increased flavodoxin enhances aminomutase activity when produced in *E. coli*. See U.S. Ser. No. 60/726,925, by Cargill, Inc. (Liao, et al), filed Oct. 14, 2005, entitled "Increasing the Activity of Radical S-Adenosyl Methionine (SAM) Enzymes" describes the production of β-alanine from cells that express AAM and overexpress flavodoxin at Examples 1-4, and these example are incorporated herein by reference. This same application, U.S. Ser. No. 60/726,925, by Cargill, Inc. (Liao, et al.) filed Oct. 14, 2005, describes in Example 4 (incorporated herein) the construction of a strain of *E. coli* in which an artificial $P_{lac/ara}$ hybrid was placed immediately upstream of the fldA gene. Strains carrying the artificial promoter before the fldA gene are designated KifldA, where KI refers to "knock-in".

Competent cells of *E. coli* ΔpanD KIfldA are prepared either chemically or electrochemically using standard protocols. Competent *E. coli* ΔpanD KIfldA was removed from −80° C. frozen storage and thawed. Thereafter, it was kept on ice until used. An aliquot (100 μl per transformation) was transferred into a sterile 1.5 ml centrifuge tube. A KCM (5×) salt solution was added until the concentration in the aliquot was 1×. KCM consists of 700 mM KCl; 10 mM morpholinopropanesulphonic acid (MOPS) adjusted to pH 5.8. 1-5 μl of the ligation mixture was added to the cells. The cells containing the ligation mixture were first incubated on ice for 30 minutes. The cells were heat shocked at 42° C. for 1 min, and subsequently incubated on ice for 2 minutes. 50001 of SOC (Maniatis, T., Fritsch, E. F., and Sambrook, J. (1982) Molecular Cloning: A Laboratory Manual, 1st Ed., pp. A.2 and A.3, Cold Spring Harbor Laboratory, Cold Spring Harbor, N.Y.) was added to the cells, and the cells were incubated at 37° C. for 1 hour with agitation. The cells were then centrifuged at 5000 rpm for 3 minutes, and the SOC was removed. Pellets were subsequently resuspended in a medium appropriate for either the complementation assay (Example 3) or the biotransformation assay (Example 4).

EXAMPLE 2

Cloning of aam Genes into pCK110900 Series Vectors

The strategy employed for cloning the alanine aminomutase genes into an inducible expression system involved the isolation of the aam gene by PCR and cloning of the PCR fragment into the SfiI restriction sites downstream from a mutant lac promoter/operator system. Initially, PCR primers were designed to contain a nucleotide sequence that is specific to the 5' and 3' ends of the aam gene, as well as the Shine-Delgarno sequence of the ribosome-binding site, and the unique SfiI restriction sites. The gene was then amplified from a template, purified and digested with the restriction endonuclease SfiI. The restricted PCR fragment was purified using the QIAquick PCR purification kit (Qiagen), and cloned into the SfiI sites of the expression vector pCK110900-I Bla of FIG. 3 under the control of a lac promoter and lacI repressor gene. The expression vector also contained the P15a origin of replication and the chloramphenicol resistance gene. Shuffled aam gene libraries were cloned by the same method. Several clones were found that expressed an active alanine 2,3-aminomutase (as per the method of Example 8) and the synthetic genes were sequenced. A polynucleotide sequence designated BSAAM (SEQ ID NO: 58)—was used as a starting material for all further mutations and shuffling. BSAAM (SEQ ID NO: 58) has approximately 99.2% nucleotide identity with the wild-type *Bacillus subtilis* lysine aminomutase (GenBank Accession No. H10329).

EXAMPLE 3

Screening Via the Tier 2a Growth Assay

Tier 2a Growth Assay

The growth assay identifies variants capable of generating the essential metabolite AcetylCoA via β-alanine produced by AAM variants in the *E. coli* ΔpanD host strain. Growth is therefore a function of CoA production, and indirectly of AAM activity.

A. Procedure

AAM active clones from the tier 1 complementation assay were picked with a QBOT™ robot colony picker (Genetix USA, Inc., Boston Mass.) and inoculated into a 96-well master plate. The inoculums were grown in the 96 well master plate on a buffered minimal selection media. ($Na_2HPO$. $7H_2O$ 12.8 g/L; $KH_2PO_4$ 3 g/L; NaCl 0.5 g/L; $NH_4Cl$ 1 g/L; $MgSO_4$ 2 mM; $CaCl_2$ 0.04 mM; mannose 2%; IPTG 1 mM; ferric citrate 20 uM; chloramphenicol 30 μg/ml; MOPS pH 7, 50 mM; and sodium bicarbonate pH 9, 25 mM) (hereinafter "MSM") to which was added 0.1 uM β-alanine and 0.5 g/L α-alanine. Plates were covered using AirPore™ microporous tape (Qiagen, Inc.) and incubated at 25° C., 250 rpm, 85% humidity until cultures reached saturation, at which time glycerol was added to the cultures to a final concentration of 20-30%, and the plates stored at −80° C.

Samples from a frozen master plate were arrayed into an "inoculum" plate containing buffered minimal selection media (MSM), as described above, further containing 0.5 g/L α-alanine. The inoculum plates were covered with AirPore™ microporous tape (Qiagen, Inc.) and incubated at 25° C., 250 rpm, 85% humidity until cultures reached saturation.

15 μl from the inoculum plate was inoculated into a 96-well "assay" plate containing 185 μl of fresh MSM with 0.5 g/L α-alanine. The assay plates were covered with AirPore™ microporous tape (Qiagen, Inc.) and a lid, and incubated at 25° C., 85% humidity, 250 rpm. Measurements of OD at 600 nm were made at discrete times for a period of approximately (~) 40 hours.

B. Data Analysis

Since library variants exhibit unique growth profiles, it was preferable to calculate and compare growth rates (slopes) at three (3) different growth phases (early, mid and late) to identify all potentially improved variants. Clones that exhibit three (3) standard deviations above the plate average in any of the three (3) phases were designated as potentially improved variants and were retested in tier 2b for comparative ranking.

EXAMPLE 4

Screening Via the Tier 2b Growth Assay

The stringency of the growth screen is increased in Tier 2b by excluding α-alanine (the substrate for AAM) from the medium. Under these conditions, the cell relies on internal/cellular pools of α-alanine to serve as a substrate for AAM, and subsequently, for cell growth. AAM variants capable of utilizing low, intracellular pools of α-alanine might represent low $K_M$ variants.

A. Procedure

Samples from a frozen master plate were arrayed into an "inoculum" plate containing buffered minimal selection media (MSM), as described above, further containing 0.5 g/L α-alanine. The inoculum plates were covered using Air-Pore™ microporous tape and incubated at 25° C., 250 rpm, 85% humidity until cultures reached growth saturation.

A TECAN™ Robotic Sample Processor (Columbus, Ohio) was used to remove 10 μl of inoculum from each Tier 2a variant from the inoculum plates and seed it in replicates of 8 into each of the following:

96-well Assay plate containing 190 μl of fresh MSM, 0.5 g/L α-alanine.

96-well Assay plate containing 190 μl of fresh MSM, containing no α-alanine.

The Assay plates were covered with AirPore™ microporous tape and a lid and grown at 25° C., 85% humidity, 250-rpm. Samples were collected at time points for approximately 3-4 days and the $OD_{600nm}$ was measured for each sample.

B. Tier 2b Data Analysis

Variants were ranked by the following 3 criteria:

i) Growth ratio equal to a final culture $OD_{600}$ on medium without α-alanine/final culture $OD_{600nm}$ on medium containing α-alanine;

ii) Final culture $OD_{600}$; and iii) Initial growth rates (in phase 1, from approximately 0-20 hour)

Clones with final culture $OD_{600nm}$>0.7 were retained.

Clones were then ranked based on the growth ratio of criteria (i). Any clones with a $OD_{600nm}$>0.7 were retained. However, clones that did not meet the above two criteria, but had a very good initial growth rate (iii) were also selected for further evaluation.

EXAMPLE 5

Screening Via Tier 2c-PCR Analysis

The PCR screen identifies variants that contain the correct size gene in the expression vector prior to further screening for function. It excludes unstable gene variants that may have undergone deletions/truncations during the screening process.

A. Procedure

Potentially improved variants from frozen master plates were inoculated into a 96-microwell plate containing LB media with 1% glucose and 30 μg/mL chloramphenicol. Cultures were grown at 25° C., 250 rpm, 85% humidity in plates covered with AirPore™ microporous tape (Qiagen, Inc.) until cultures reached saturation, approximately 2 days. 10 μL of the culture was transferred to a PCR plate and boiled at 99° C. for 10 minutes to disrupt the cells. Thereafter, 90 μL of the following PCR Master Mix was added to the disrupted cells:

PCR Master Mix:

| | |
|---|---|
| 10 μL | 10X Taq Polymerase Buffer (QIAGEN, Valencia CA) |
| 4 μL | 25 mM $MgCl_2$ |
| 2 μL | 10 mM dNTPs |
| 1.25 μL | 20 μM primer - $B_{forward}$ (specific for BsAAM gene) |
| 1.25 μL | 20 μM primer - $B_{reverse}$ (specific for BsAAM gene) |
| 1 μL | 5 U/μL Taq polymerase (QIAGEN) |
| 70.5 μL | Sterile water |
| 90 μL | Total volume |

The *Bacillus* specific primers used in the PCR reaction are as follows:

```
B-forward:
                                            SEQ ID NO: 63
5'ccagcctggccataaggagatatacatatgaaaaacaaatggtataaa
c 3'

B-reverse:
                                            SEQ ID NO: 64
5'atggtgatggtgatggtggccagtttggccttatgaagaatcccctcc
gc 3'
```

The amplification reaction was run for 30 cycles. The first cycle was run at 94° C. for 1 minute. Thereafter, the extension procedure was performed for 29 cycles: 94.0° C. for 1 minute; 55.0° C. for 30 seconds; and 72.0° C. for 1 minute. The final extension was performed at 72.0° C. for 5 minutes. The products of the PCR reactions were analyzed by gel-electrophoresis on a 0.8% agarose gel.

EXAMPLE 6

Growth of AAM Variants for β-Alanine Production (50 ml Scale)

Cell Selection Method for Identifying AAM Activity.

To identify genes encoding polypeptides that can perform the alanine 2,3-aminomutase reaction, an efficient screen or selection for the desired activity is needed. Therefore, a selection method was developed by recognizing that *E. coli* uses beta-alanine for the synthesis of pantothenic acid, which in turn is a component of coenzyme A (CoA) and of acyl carrier protein (ACP). CoA and ACP are the predominant acyl group carriers in living organisms, and are essential for growth.

In *E. coli*, the primary route to beta-alanine is from aspartate in a reaction catalyzed by aspartate decarboxylase (E.C. 4.1.1.11), which is encoded by the panD gene. A functional deletion mutation of panD (shown as ΔpanD) results in beta-alanine auxotrophy and growth inhibition, which can be alleviated by the exogenous addition of pantothenate or beta-alanine, or by the production of beta-alanine from another source.

Strain description: *E. coli* ΔpanD host (derived from BW25113, described in Datsenko, K. A. and Wanner, B. L., Proc. Natl. Acad. Sci. USA 97:6640-6645 (2000)), transformed with pCK110900-I Bla vector (low promoter strength resulting from mutated lac promoter sequence). The inoculum culture was grown in buffered minimal selection medium (MSM): M9 salts, pH 7.0-7.4, 50 mM MOPs, pH 7.0, 25 mM sodium bicarbonate, pH 9.0, 1 mM isopropyl-β-D-thiogalactoside (IPTG), 30 μg/ml chloramphenicol, 0.1 g/L alanine, 5 uM pyridoxine HCl, and 20 uM ferric citrate. A 1:20 dilution of inoculum was used to inoculate 50 ml of MSM medium described above. Cultures were incubated at 25° C., 250 rpm for approximately 3 days or until the culture reaches $OD_{600nm}$~1. Then, α-alanine was added to the medium to a final concentration of 300 mM, and pantothenate was added to about 300 uM. Incubation of the supplemented medium continued at 25° C., 250 rpm. Samples were removed from the medium for analysis at time points from t=0 through t=5 hours following the addition of α-alanine.

EXAMPLE 7

Method for Extracting Cells for β-Alanine Detection

Cells from the cultures of Example 6 were harvested by centrifugation of the cultures. The supernatant (spent media)

was decanted and saved for further analysis (below). The cell pellets were washed with water. Pellets may be stored at −80° C. for future extraction. The 50 ml cell pellets (OD ~4.0) were re-suspended completely in a test tube in 0.9 ml water. The extraction volume for each sample was adjusted to this proportion according to the harvest $OD_{600}$. An equal volume of methanol (−20° C.) and 200 µL of micro-glass beads was added and the mixture vortexed vigorously. Tubes containing the mixtures were placed on dry ice/EtOH, or in a −80° C. freezer, for about 30 min. The frozen contents in the tube were thawed at room temperature and vortexed vigorously again, and centrifuged at maximum speed for about 10 minutes. The supernatants were filtered using 0.2-0.45 micron filter plates, or syringe filters.

The spent medium was filtered using a 0.2-0.45 micron filter plate or syringe filter. The filtered spent medium was diluted 1:10 in −20° C. methanol/water (final methanol concentration 50%).

The β-alanine content of cell extract and spent media was analyzed by LC/MS/MS (Example 8).

For spent medium sample, the first minute was diverted to waste. The β-alanine peak arrived at approximately 2.0 minutes.

The assay can be scaled to 2 ml, if only the spent media is analyzed.

EXAMPLE 8

Assay for β-alanine (LC/MS/MS)

β-alanine was determined using a combination of liquid chromatography and mass spectrometry. Suitable analytes were the cell extracts and spent media as prepared in Example 7.

The liquid chromatography (LC) phase was performed using an ASTEC CHIROBIOTIC™ 4.6 cm×50 mm chiral LC column (Advanced Separation Technologies, Inc., Whippany, N.J. USA). The mobile phase consisted of two solutions: A: 0.25% aqueous acetic acid; and B: 0.25% (v/v) acetic acid in methanol. The elution was isocratic @ 0.6 ml/minute.

The mass spectrometer (MS) analysis was performed on a Micromass Ultima Triple Quad mass spectrometer, using the following tune parameters: Capillary: 3.5 kV; cone: 20 V; hex 1: 15 V; aperture: 1.0V; source temp: 100° C.; desolvation temp: 350° C.; cone gas: 40 L/hr; desolvation gas: 500 L/h; low mass resolution (Q1): 12; high mass resolution (Q1): 12; ion energy (Q1): 0.1; collision cell entrance: −5; collision energy: 14; exit: 1; low mass resolution (Q2): 15 high mass resolution (Q2): 15; ion energy (Q2): 3.0; multiplier: 650 V.

MS Method

| Analyte | Alanine transitions | | |
|---|---|---|---|
| | Parent Ion (m/z) | Daughter Ion (m/z) | Dwell Time (sec) |
| α-alanine | 90 | 44.7 | 0.1 |
| β-alanine | 90 | 30.7 | 0.1 |
| α-lysine | 147 | 84.5 | 0.1 |
| β-lysine | 147 | 70.5 | 0.1 |

The inter-channel delay was 0.1 seconds.

What is claimed is:

1. A polypeptide having alanine 2,3-aminomutase (AAM) activity and having an amino acid sequence selected from the group consisting of:

(a) an amino acid sequence selected from the group consisting of SEQ ID NO: 2, 4, 6, 8, 10, 12, 14, 16, 18, 22, 24, 26, 28, 30, 32, 34, 36, 38, 40, 42, 44, 46, 48, and 51;

(b) an amino acid sequence which has at least 95% homology with the amino acid sequence of SEQ ID NO: 34, wherein the amino acid sequence of the AAM polypeptide comprises an amino acid residue selected from the group consisting of L at position 177, M at position 227, R at position 308, L at position 408, S at position 416, and G at position 447; and (c) an amino acid sequence encoded by a nucleic sequence which hybridizes under high stringency conditions with the complement of the nucleotide sequence of SEQ ID NO: 33, wherein the encoded amino acid sequence comprises an amino acid residue selected from the group consisting of L at position 177, M at position 227, R at position 308, L at position 408, S at position 416, and G at position 447, wherein the amino acid positions refer to the corresponding positions in SEQ ID NO:34, and wherein the high stringency conditions are hybridization at 42° C. in 5×SSPE, 0.3% SDS, 200 μg/ml sheared and denatured salmon sperm DNA and 50% formamide, and washing three times each for 15 minutes using 2× SSC, 0.2% SDS at a temperature of at least 65° C.

2. The polypeptide of claim 1, wherein the polypeptide has an amino acid sequence encoded by a nucleic acid sequence which hybridizes under high stringency conditions with the complement of the nucleotide sequence of SEQ ID NO: 33, wherein the encoded amino acid sequence comprises an amino acid residue selected from the group consisting of L at position 177, M at position 227, R at position 308, L at position 408, S at position 416, and G at position 447, wherein the amino acid positions refer to the corresponding positions in SEQ ID NO: 34, and wherein the high stringency conditions are hybridization at 42° C. in 5× SSPE, 0.3% SDS, 200 μg/ml sheared and denatured salmon sperm DNA and 50% formamide, and washing three times each for 15 minutes using 2× SSC, 0.2% SDS at a temperature of at least 65° C.

3. The polypeptide of claim 1 having the amino acid sequence of SEQ ID NO: 34.

4. An AAM polypeptide of claim 1 in lyophilized form.

5. A composition comprising a polypeptide of claim 1 in a buffered medium

6. A method of making an AAM polypeptide comprising (a) cultivating a host cell comprising a nucleic acid construct comprising a nucleic acid sequence encoding the AAM polypeptide of claim 1 under conditions suitable for production of the polypeptide; and (b) recovering the AAM polypeptide.

7. The polypeptide of claim 1 having an amino acid sequence which has at least 95% homology with the amino acid sequence of SEQ ID NO: 34, wherein the amino acid sequence of the AAM polypeptide comprises an amino acid residue selected from the group consisting of L at position 177, M at position 227, R at position 308, L at position 408, S at position 416, and G at position 447.

8. The polypeptide of claim 7 wherein the amino acid sequence comprises an amino acid residue selected from the group consisting of R at position 308 and S at position 416.

9. The polypeptide of claim 8 wherein the amino acid sequence comprises R at position 308 and S at position 416.

10. The polypeptide of claim 7 having an amino acid sequence which has at least 98% homology with the amino acid sequence of SEQ ID NO: 34.

11. The polypeptide of claim 10 having an amino acid sequence which has at least 99% homology with the amino acid sequence of SEQ ID NO: 34.

12. A polynucleotide encoding an AAM polypeptide of claim 1.

13. A host cell transformed to express a polynucleotide of claim 12.

14. A polynucleotide encoding a polypeptide having AAM activity, said polynucleotide having the sequence of SEQ ID NO: 33.

15. An expression vector comprising a polynucleotide of claim 12 or 14 operatively linked to a promoter.

16. A polynucleotide encoding the AAM polypeptide of claim 7.

17. An expression vector comprising the polynucleotide of claim 16.

18. A host cell transformed to express the polynucleotide of claim 16.

19. A method of making an AAM polypeptide comprising (a) cultivating a host cell comprising a nucleic acid construct comprising a nucleic acid sequence encoding the AAM polypeptide of claim 7 under conditions suitable for production of the polypeptide; and (b) recovering the AAM polypeptide.

* * * * *

SEQUENCE LISTING

```
<160> NUMBER OF SEQ ID NOS: 65

<210> SEQ ID NO 1
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 1

atgaaaaaca aatggtataa accgaaacgg cattggaagg agatcgagct atggaaggac      60

gttccggaag agaaatggaa cgattggctt tgacagctga cgcacactgt aagaacgtta     120

gatgatttaa agaaagtcat taatctgacc gaggatgaag aggaaggcgt ccgtatttct     180

accaaaacga tccccttaaa tattacacct tactatgctt ctttaatgga ccccgacaat     240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaattttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa taccatccgg tccggctgaa cacccatttt     720
```

-continued aacacaagca tcgaaatgac agaagaaccc gttgaggcac gtgaaaagct ggtgaacgcg 780
ggagtgccgg tcggaaatca ggctgtcgta ttagcaggta ttaatggctc ggttccaatt 840
atgaaaaagc tcatgcatga cttggtaaaa atcagagtcc gtccttatta tatttaccaa 900
tgtgatctgt cagaaggaat aaggcatttc cgtgctcctg tttccaaagg tttggagatc 960
attgaagggc tgagaggtca tacctcaggc tatgcggttc ctacctttgt cgttcacgca 1020
ccaggcggag gggtaaaat cgccctgcag ccgaactatg tcctgtctca aagtcccgac 1080
aaagtgatct taagaaattt tgaaggtgtg attacgtcat atccggaacc agagaattgt 1140
acccccaatc aggcagacgc ctattttgag tccgttttcc ctgaaaccgc tgacaaaaag 1200
gagccgatcg ggctgagtgc cattttgct gacaaagaag tttcgtctac acccgaaaat 1260
gtagacagaa tcaaacggcg tgaggcatac atcgcaaatc cggagcatga aacattagaa 1320
gatcggcgtg agaaaagagg tcagctcaaa gaaaagaaat tttggcgca gcagaaaaaa 1380 cagaaagaga ctgaatgcgg aggggattct tcataa 1416

<210> SEQ ID NO 2
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 2

Met Lys Asn Lys Trp Tyr Lys Pro Lys Arg His Trp Lys Glu Ile Glu
1 5 10 15

Leu Trp Lys Asp Val Pro Glu Glu Lys Trp Asn Asp Trp Leu Trp Gln
20 25 30

Leu Thr His Thr Val Arg Thr Leu Asp Asp Leu Lys Lys Val Ile Asn
35 40 45

Leu Thr Glu Asp Glu Glu Glu Gly Val Arg Ile Ser Thr Lys Thr Ile
50 55 60

Pro Leu Asn Ile Thr Pro Tyr Tyr Ala Ser Leu Met Asp Pro Asp Asn
65 70 75 80

Pro Arg Cys Pro Val Arg Met Gln Ser Val Pro Leu Ser Glu Glu Met
85 90 95

His Lys Thr Lys Tyr Asp Met Glu Asp Pro Leu His Glu Asp Glu Asp
100 105 110

Ser Pro Val Pro Gly Leu Thr His Arg Tyr Pro Asp Arg Val Leu Phe
115 120 125

Leu Val Thr Asn Gln Cys Ser Val Tyr Cys Arg His Cys Thr Arg Arg
130 135 140

Arg Phe Ser Gly Gln Ile Gly Met Gly Val Pro Lys Lys Gln Leu Asp
145 150 155 160

Ala Ala Ile Ala Tyr Ile Arg Glu Thr Pro Glu Ile Arg Asp Cys Leu
165 170 175

Ile Ser Gly Gly Asp Gly Leu Leu Ile Asn Asp Gln Ile Leu Glu Tyr
180 185 190

Ile Leu Lys Glu Leu Arg Ser Ile Pro His Leu Glu Val Ile Arg Ile
195 200 205

Gly Thr Arg Ala Pro Val Val Phe Pro Gln Arg Ile Thr Asp His Leu
210 215 220

Cys Glu Ile Leu Lys Lys Tyr His Pro Val Arg Leu Asn Thr His Phe
225 230 235 240

-continued

```
Asn Thr Ser Ile Glu Met Thr Glu Glu Pro Val Glu Ala Arg Glu Lys
                245                 250                 255

Leu Val Asn Ala Gly Val Pro Val Gly Asn Gln Ala Val Val Leu Ala
            260                 265                 270

Gly Ile Asn Gly Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Cys Thr Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Glu Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 3
<211> LENGTH: 1416
<212> TYPE: DNA
<213> ORGANISM: Artificial Sequence
<220> FEATURE:
<223> OTHER INFORMATION: Synthetic Construct

<400> SEQUENCE: 3

atggaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacct tactatgctt ctttaatgga ccccgacaat     240

ccgagatgcc cggtacgcat gcagtctgtg ccgctttctg aagaaatgca caaaacaaaa     300

tacgatatgg aagacccgct tcatgaggat gaagattcac cggtgcccgg tctgacacac     360

cgctatcccg accgtgtgct gtttcttgtc acgaatcagt gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcgtt     660

accgatcatc tgtgcgagat attgaaaaaa tatcatccgg tctggctgga cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctggc   1080

agagtgatct taagaaattt tgaaggtgtg attacgtcat acccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa    1380

cagaaagaga ctgaatgcgg aggggattct tcataa                              1416


<210> SEQ ID NO 4
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 4

Met Glu Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Val Thr Asp His Leu
    210                 215                 220

Cys Glu Ile Leu Lys Lys Tyr His Pro Val Trp Leu Asp Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Gly Arg Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 5
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 5

atgaaaaaca aatggtataa accgaaacgg cattggaagg agatcgagtt atggaaggac     60

gttccggaag ggaaatggaa cgattggctt tgacagctga cacacactgt aagaacgtta    120

gatgatttaa agaaagtcat taatctgacc gaggatgaag aggaaggcgt ccgtatttct    180

accaaaaacga tcccccttaaa tattacacct tactatgctt ctttaatgga ccccgacaat    240

ccgagatgcc cggtacgcat gcagtctgtg ccgctttctg aagaaataca caaaacaaaa    300

tacgatatgg aagacccgct tcatggggat gaagactcac cggtacccgg tctgacacac    360

cgctatcccg accgtgtgct gtttcttgtc acgaatcaat gttctgtgta ctgccgccac    420

tgcacacgcc ggcgcttttc cggacaaatc ggaatgggcg tccccaaaaa acagcttgat    480

gctgcaattg cttatatccg ggaaacaccc gaaatccgcg attgtttaat ttcaggcggt    540

gatgggctgc tcatcaacga ccaaatttta gaatatattt taaaagagct gcgcagcatt    600

ccgcatctgg aagtcatccg catcggaaca cgtgcccccg tcgtctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc cattttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                              1416
```

<210> SEQ ID NO 6
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 6

```
Met Lys Asn Lys Trp Tyr Lys Pro Lys Arg His Trp Lys Glu Ile Glu
1               5                   10                  15

Leu Trp Lys Asp Val Pro Glu Gly Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Ile
                85                  90                  95

His Lys Thr Lys Tyr Asp Met Glu Asp Pro Leu His Gly Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 7
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 7

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacca tactatgcga gcttaatgga tccagaaaac     240

ccacgttgtc cggtacgcat gcagtctgtg ccgctttccg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc cgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tctccaaagg tttggagatc    960

attgaagggc tgagaggtca taccccaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgtttccc ctgaaaccgc tgacaaaaag   1200

gagccgatcg ggctgagtgc catttttgct gacaaagaag tttcgtctac acctgaaaat   1260

gtagacagaa tcaaacggcg tgaggcctac atcgcaaatc cggagcatga aacattaaaa   1320

gatcggcgtg agaaaagagg tcagctcaaa gaaaagaaat tttcggcgca gcagaaaaaa   1380

cagaaagaga ctgaatgcgg aggggattct tcataa                             1416
```

```
<210> SEQ ID NO 8
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 8

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Glu Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Pro
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Pro Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Ser Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Ser Ala Gln Gln Lys Lys Gln Lys Glu Thr
    450                 455                 460

Glu Cys Gly Gly Asp Ser Ser
465                 470


<210> SEQ ID NO 9
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 9

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacct tactatgctt ctttaatgga ccccgacaat     240

ccgagatgcc cggtgcgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tgtttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                             1416
```

```
<210> SEQ ID NO 10
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 10

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Val Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 11
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 11

atgaaaaaca aatggtataa accgaaacgg cattggaagg agatcgagtt atggaaggac      60

gtcccggaag agaaatggaa cgattggctt tgacagctga cacacactgt aggaacgtta     120

gatgatttaa agaaagtcat caatctgacc gaggatgaag aggaaggcgt ccgtatttct     180

accaaaaacga tcccccttaaa tattacacct tactatgctt ctttaatgga ccccgacaat     240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaag gttccgtgta ctgccgccac     420

cgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatccgg aagtcatccg catcggaaca cgtgctcccg tcgtcttccc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaact    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggcca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgcca gcagaaaaaa   1380

cagaaagaga ctgaatgcgg aggggattct tcataa                             1416
```

<210> SEQ ID NO 12
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 12

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Gly Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Gly Ser Val Tyr Cys Arg His Arg Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Pro Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Thr Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 13
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 13

```
atgaaaaaca aatggtataa accgaaacgg cattgggagg agatcgagcg atggaaggac     60

gttccggaag agaaatggaa cgattggctt tgacagctga cacacactgt aagaacgtta    120

gatgatttaa agaaagtcat taatctgacc gaggatgaag aggaaggcgt ccgtatttct    180

accaaaacga tccccttaaa tattacacct tactatgctt ccttaatgga ccccgacaat    240

ccgagatgcc cggtacgcat gcagtctgtg ccgctttctg aagaaatgca caaaacaaaa    300

tacgatatgg aagacccgct tcatgaggat gaagattcac cggtacccgg tctgacacac    360

cgctatcccg accgtgtgct gtttcttgtc acgaatcaat gttccgtgta ctgccgccac    420

tgcacacgcc ggcgcttttc cggacaaatc gggatgggcg tccccaaaaa acagcttgat    480

gctgcaattg cttatatccg ggaaacaccc gaaatccgcg attgtttaat ttcaggcggt    540

gatgggctgc tcatcaacga ccaaatttta gaatatattt taaaagagcc gcgcagcact    600

ccgcatctgg aagtcatccg catcggaaca cgtgctcccg tcgtctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

gtgaaaaagc tcatgcatga cttggtaaaa atcagagtcc gtccttatta tatttaccaa    900

tgtgatctgt cagaaggaat aaggcattcc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                             1416
```

```
<210> SEQ ID NO 14
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 14

Met Lys Asn Lys Trp Tyr Lys Pro Lys Arg His Trp Glu Glu Ile Glu
1               5                   10                  15

Arg Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Pro Arg Ser Thr Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Val Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Ser Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 15
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 15

```
atgaaaaaca aatggtataa accgaaacgg cattgggagg agatcgagcg atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacct tactatgctt ccttaatgga ccccgacaat     240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc gggatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagcc gcgcagcact     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

gtgaaaaagc tcatgcatga cttggtaaaa atcagagtcc gtccttatta tatttaccaa    900

tgtgatctgt cagaaggaat aaggcattcc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa    1380

cagaaagaga ctgaatgcgg aggggattct tcataa                             1416
```

<210> SEQ ID NO 16
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 16

```
Met Lys Asn Lys Trp Tyr Lys Pro Lys Arg His Trp Glu Glu Ile Glu
1               5                   10                  15

Arg Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Pro Arg Ser Thr Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Val Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Ser Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 17
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 17

atgaaaaaca aatggtataa accgaaacgg cattggaagg agatcgagtt atggaaggac      60

gttccggaag agaaatggaa cgattggctt tgacggctga cacacactgt aagaacgtta     120

gatgatttaa agaaagtcat taatctgacc gaggatgaag aggaaggcgt ccgtatttct     180

accaaaaacga tcccccttaaa tattacacct tactatgctc ctttaatgga ccccgacaat     240

ccgagatgcc cggtacgcat gcagtctgtg ccgctttccg aagaaatgca caaaacaaaa     300

tacgatatgg aagacccgct tcatgaggat gaagatacac cggtacccgg tccgacacac     360

cgctatcccg accgtgtgct gtttcttgtc acgaatcaat gctccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa   1380

cagaaagaga ctgaatgcgg aggggattct tcataa                             1416
```

<210> SEQ ID NO 18
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 18

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Arg
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Pro Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Thr Pro Val Pro Gly Pro Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 19
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 19

atggaaaaca aatggtataa accgaaacgg cattggaagg agatcgagtt atggaaggac     60

gttccggaag agaaatggaa cgattggctt tgacagctga cacacactgt aagaacgtta    120

gatgatttaa agaaagtcat taatctgacc gaggatgaag aggaaggcgt ccgtatttct    180

accaaaaacga tcccccttaaa tattacacct tactatgctt ctttaatgga ccccgacaat    240

ccgagatgcc cggtacgcat gcagtctgtg ccgctttctg aagaaatgca caaaacaaaa    300

tacgatatgg aagacccgct tcatgaggat gaagattcac cggtacccgg tctgacacac    360

cgctatcccg accgtgtgct gtttcttgtc acgaatcaat gttccgtgta ctgccgccac    420

tgcacacgcc ggcgcttttc cggacaaatc ggaatgggcg tccccaaaaa acagcttgat    480

gctgcaattg cttatatccg ggaaacaccc gaaatccgcg attgtttaat ttcaggcggt    540

gatgggctgc tcatcaacga ccaaatttta gaatatattt taaaagagct gcgcagcatt    600

ccgcatctgg aagtcatccg catcggaaca cgtgctcccg tcgtctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt ctgagggctt ggggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtcaca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtttac acctgaaaat   1260

gtagacagaa tcaaacggcg tgaggcatac atcgcaaatc cggagcatga aacattaaaa   1320

gatcggcgtg agaaaagaga tcagctcaaa gaaaagaaat ttttggcgca gcagaaaaaa   1380

cagaaagaga ctgaatgcgg aggggattct tcataa                             1416
```

```
<210> SEQ ID NO 20
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 20

Met Glu Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Leu Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 21
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 21

atgaaaaaca aatggtataa accgaaacgg cattggaagg agatcgagtt atggaaggac      60

gtcccggaag agaaatggaa cgattggctt tgacagctga cacacactgt aagaacgtta     120

gatgatttaa agaaagtcat taatctgacc gaggatgagg aggaaggcgt ccgtatttct     180

accaaaaacga tcccccttaaa tattacacct taccatgctt ctttaatgga ccccgacaat     240

ccgagatgcc cggtacgcat gcagtctgtg ccgctttctg aagaaatgca caaaacaaaa     300

tacgacatgg aagacccgct tcatgaggat gaagattcac cggtacccgg tccgacacac     360

cgctatcccg accgtgtgct gtttcttgtc acgaatcaat gttccgtgta ctgccgccac     420

tgcacacgcc ggctcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcgtt     660

accgatcatc tgtgcgagat attgaaaaaa tatcatccgg tctggctgaa cacccatctt     720
```

-continued

```
aacacaagca tcgaaatgac agaagaaccc gttgaggcat gtgaaaagct ggtgaacgcg    780

ggagtgccgg tcggaaatca ggctgtcgta ttagcgggta ttaatgattc ggttccaatt    840

atgaaaaagc tcatgcatga cttggtaaaa atcagagtcc gtccttatta tatttaccaa    900

tgtgatctgt cagaaggaat aaggcatttc tgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggagcc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                              1416
```

<210> SEQ ID NO 22
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 22

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr His Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Pro Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Leu Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Val Thr Asp His Leu
    210                 215                 220

Cys Glu Ile Leu Lys Lys Tyr His Pro Val Trp Leu Asn Thr His Leu
225                 230                 235                 240
```

-continued

```
Asn Thr Ser Ile Glu Met Thr Glu Glu Pro Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Cys Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 23
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 23

atgaaaaaca aatggtataa accgaaacgg cattggaagg agatcgagtt atggaaagac      60

gttccggacg aaaagtggaa cgattggctt tgacagctga cacacactgt aagaacgtta     120

gatgattcaa agaaagtcat taatctgacc gaggatgaag aggaaggcgt ccgtatttct     180

accaaaaacga tcccccttaaa tattacacct tactatgctt ctttaatgga ccccgacaat    240

ccgagatgcc cggtacgcat gcagtctgtg ccactttctg aagaaatgca caaaacaaaa     300

tacgatatgg aagacccgct tcatgaggat gaagattcac cggtacccgg tctgacacac     360

cgctatcccg gccgtgtgct gtttcttgtc acgaatcaat gttccgtgca ctgccgccac     420

tgcacacgcc ggcgcttttc cggacaaatc ggaatgggcg tccccgaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg     780

ggagtgccgg tcggaaatca ggctgtcgta ttagcaggta ttaatgattc ggttccaatt     840

atgaaaaagc tcatgcatga cttggtaaaa atcagagtcc gtccttatta tatttaccaa     900

tgtgatctgt cagaaggaat aaggcatttc cgtgctcctg tttccaaagg tttggagatc     960

attgaagggc tgagaggtca tacctcaggc tatgcggttc ctacctttgt cgttcacgca    1020

ccaggcggag gaggtaaaat cgccctgcag ccgaactatg tcctgtctca aagtcctgac    1080

aaagtgatct taagaaattt tgaaggtgtg attacgtcat atccggaacc agagaattat    1140

atccccaatc aggcagacgc ctattttgag tccgttttcc ctgaaaccgc tgacaaaaag    1200

gagccgatcg ggctgagtgc catttttgct ggcaaagaag tttcgtctac acctgaaaat    1260

gtagacagaa tcaaacggcg tgaggcatac atcgcaaatc cggagcatga aacattaaaa    1320

gatcggcgtg agaaaagagg tcagctcaaa gaaaagaaat ttttggcgca gcagaaaaaa    1380

cagaaagaga ctgaatgcgg aggggattct tcataa                              1416
```

<210> SEQ ID NO 24
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 24

```
Met Lys Asn Lys Trp Tyr Lys Pro Lys Arg His Trp Lys Glu Ile Glu
1               5                   10                  15

Leu Trp Lys Asp Val Pro Asp Glu Lys Trp Asn Asp Trp Leu Trp Gln
            20                  25                  30

Leu Thr His Thr Val Arg Thr Leu Asp Asp Ser Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Gly Arg Val Leu Phe
        115                 120                 125

Leu Val Thr Asn Gln Cys Ser Val His Cys Arg His Cys Thr Arg Arg
    130                 135                 140

Arg Phe Ser Gly Gln Ile Gly Met Gly Val Pro Glu Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Gly Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 25
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 25

atgaaaaaca aatggtataa accgaaacgg cattggaagg agatcgagtt atggaaggac      60

gttccggaag agaaatggaa cgattggctt tgacagctga cacacactgt aagaacgttg     120

gatgatttaa agaaagtcat taacctgacc gaggatgaag aggaaggcgt ccgtatttct     180

accaaaaacga tcccccttaaa tattacacct tactatgctt ctttaatgga ccccgacaaa    240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgacctgt cagaaggaat aaggcatttc cgtgctcctg tttccaaagg tttggggatc    960

attgaagggc tgggaggtca tacctcaggc tatgcggttc ctacctttgt cgttcacgca   1020

ccaggcggag gaggtaaaat cgccctgcgg ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaagaag   1200

gagccgatcg ggctgagtgc cattttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa   1380

cagaaagaga ctgaatgcgg aggggattct tcataa                            1416
```

```
<210> SEQ ID NO 26
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 26

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Lys
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Gly Ile
305                 310                 315                 320

Ile Glu Gly Leu Gly Gly His Thr Ser Gly Tyr Ala Val Pro Thr Phe
                325                 330                 335

Val Val His Ala Pro Gly Gly Gly Gly Lys Ile Ala Leu Arg Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 27
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 27

```
atgaaaaaca aatggtataa accgaaacgg cattggaagg agatcgagtt atggaaggac     60

gttccgggag agaaatggaa cgattggctt tgacagctga cacacactgt aagaacgtta    120

gatgatttaa agaaagtcat taatctgacc gaggatgaag aggaaggcgt ccgtatttct    180

accaaaacga tccccttaaa tattacacct tgctatgctc ctttaatgga ccccgacaac    240

ccgagatgcc cggtacgcat gcagtctgtg ccgctttctg aagaaatgca caaaacaaaa    300

tacgatatgg aagacccgct tcgtgaggat gaagattcac cggtacccgg tctgacacac    360

cgctatcccg accgtgtgct gtttcttgtc acgaatcaat gttccgtgta ctgccgccac    420

tgcacacgcc ggcgcttttc cggacaaatc ggaatgggcg tccccaaaaa acagcttgat    480

gctgcaattg cttatatccg ggaaacaccc gaaatccgcg attgtttaat ttcaggcggt    540

gatgggctgc tcatcaacgg ccaaatttta gaatatattt taaaagagct gcgcagcatt    600

ccgcatctgg aagtcatccg catcggaaca cgtgctcccg tcgtctttcc gcagcgcatt    660

accgatcatc tgtgcgagat attgaaaaaa tatcatccgg tctggctgaa cacccatttt    720
```

-continued

```
aacacaagcg tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gggtaaaat cgccctgcag ccgaactatg tcctgtctca aagtcctgac   1080

aaagtaatct taagaaattt tgaaggtgtg attacgtcat atccggaacc agagaattat   1140

atccccaatc aggcagacgc ctattttgag tccgttttcc ctggaaccgc tgacaaaaag   1200

gagccgatcg ggctgagtgc cattttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ctttggcgca gcagaaaaaa   1380

cagaaagaga ctgaatgcgg aggggattct tcataa                             1416
```

<210> SEQ ID NO 28
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 28

```
Met Lys Asn Lys Trp Tyr Lys Pro Lys Arg His Trp Lys Glu Ile Glu
1               5                   10                  15

Leu Trp Lys Asp Val Pro Gly Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Cys Tyr Ala Pro Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu Arg Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Gly Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Val Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Gly Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Ser Leu Ala Gln Gln Lys Lys Gln Lys Glu Thr
    450                 455                 460

Glu Cys Gly Gly Asp Ser Ser
465                 470


<210> SEQ ID NO 29
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 29

atgaaaaaca aatggtataa accgaaacgg cattggaagg agatcgagtt atggaaggac      60

gttccggaag agaaatggaa cgattggctt tgacggctga cacacactgt aagaacgtta     120

gatgatttaa agaaagtcat taatctgacc gaggatgaag aggaaggcgt ccgtatttct     180

accaaaacga tccccttaag tattacacct tactatgctt ctttaatgga ccccgacaat     240

ccgagatgcc cggtacgcat gcagtctgtg ccgctttctg aggaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccgc     420

tgcacacgcc ggcgcttttc cggacagatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cctggtaaaa atcagagtcc gtccttatta tatttaccaa    900

tgtgatctgt cagaaggaat acggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                              1416
```

```
<210> SEQ ID NO 30
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 30

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Arg
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Ser Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg Arg Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 31
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 31

atgaaaaaca aatggtataa accgaaacgg cattggaagg agatcgagtt atggaaggac      60

gttccggaag agaaatggaa cgattggctt tgacagctga cacgcactgt aagaacgtta     120

gatgatttaa agaaagtcat taatctgacc gaggatgaag aggaaggcgt ccgtatttct     180

accaaaaacga tcccccttaaa tattacacct tactatgcga gcttaatgga tccagaaaac     240

ccacgttgtc cggtacgcat gcagtctgtg ccgctttctg aagaaatgca cacaagcaaa     300

tatgacatgg aagatccgct tcatgaggat gaagattcac cggtacccgg tctgacacac     360

cgctatcccg accgtgtgct gtttcttgtc acgagtcaat gtcccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg gagtcatccg catcggaaca cgtgctcccg tcgtctttcc gcagcgcatt     660

accgatcatc tgtgcgagat attgaaaaga tatcatccgg tctggctgaa cacccatttt     720
```

-continued aacacaagca tcgaaatgac agaagaatcc gttgaggcat gtgaaaagct ggtgaacgcg 780
ggagtgccgg tcggaaatca ggctgtcgta ttagcaggta ttaatgattc ggttccaatt 840
atgaaaaagc tcatgcatga cttggtaaaa atcagagtcc gtccttatta tatttaccaa 900
tgtgatctgt cagaaggaat aaggcatttc cgtgctcctg tttccaaagg tttggagatc 960
attgaagggc tgagaggtca tacctcaggc tatgcggttc ctacctttgt cgttcacgca 1020
ccaggcggag gaggtaaaat cgccctgcag ccgaactatg tcctgtctca aagtcctgac 1080
aaagtgatct taagaaattt tgaaggtgtg attacgtcat atccggaacc agagaattat 1140
atccccaatc aggcagacgc ctattttgag tccgttttcc ctgaaaccgc tgacaaaaag 1200
gagccgatcg ggctgagtgc catttttgct gacaaagaag tttcgtctac acctgaaaat 1260
gtagacagaa tcaaacggcg tgaggcatac atcgcaaatc cggagcatga aacattaaaa 1320
gatcggcgtg agaaaagagg tcagctcaaa gaaaagaaat tttggcgcca gcagaaaaaa 1380
cagaaagaga ctgaatgcgg aggggattct tcataa 1416

<210> SEQ ID NO 32
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 32

Met Lys Asn Lys Trp Tyr Lys Pro Lys Arg His Trp Lys Glu Ile Glu
1 5 10 15

Leu Trp Lys Asp Val Pro Glu Glu Lys Trp Asn Asp Trp Leu Trp Gln
20 25 30

Leu Thr Arg Thr Val Arg Thr Leu Asp Asp Leu Lys Lys Val Ile Asn
35 40 45

Leu Thr Glu Asp Glu Glu Glu Gly Val Arg Ile Ser Thr Lys Thr Ile
50 55 60

Pro Leu Asn Ile Thr Pro Tyr Tyr Ala Ser Leu Met Asp Pro Glu Asn
65 70 75 80

Pro Arg Cys Pro Val Arg Met Gln Ser Val Pro Leu Ser Glu Glu Met
85 90 95

His Thr Ser Lys Tyr Asp Met Glu Asp Pro Leu His Glu Asp Glu Asp
100 105 110

Ser Pro Val Pro Gly Leu Thr His Arg Tyr Pro Asp Arg Val Leu Phe
115 120 125

Leu Val Thr Ser Gln Cys Pro Val Tyr Cys Arg His Cys Thr Arg Arg
130 135 140

Arg Phe Ser Gly Gln Ile Gly Met Gly Val Pro Lys Lys Gln Leu Asp
145 150 155 160

Ala Ala Ile Ala Tyr Ile Arg Glu Thr Pro Glu Ile Arg Asp Cys Leu
165 170 175

Ile Ser Gly Gly Asp Gly Leu Leu Ile Asn Asp Gln Ile Leu Glu Tyr
180 185 190

Ile Leu Lys Glu Leu Arg Ser Ile Pro His Leu Gly Val Ile Arg Ile
195 200 205

Gly Thr Arg Ala Pro Val Val Phe Pro Gln Arg Ile Thr Asp His Leu
210 215 220

Cys Glu Ile Leu Lys Arg Tyr His Pro Val Trp Leu Asn Thr His Phe
225 230 235 240

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 33
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 33

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaacga tccccttaaa tattacacct tactatgctt ctttaatgga ccccgacaat     240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg actgtctgtt gtctggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcacc tgtgcgagat gttaaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc gctgtttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat ttttggcgca gcagaaaaaa   1380

cagaaagaga ctgaatgcgg aggggattct tcataa                              1416
```

```
<210> SEQ ID NO 34
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 34

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Leu Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Met Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Leu Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 35
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 35

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tatcacacct tactatgcga gcttaatgga tccagaaaac    240

ccacgttgtc cggtacgcat gcagtctgtg ccgcttcctg aagaaatgca caaaacaaaa     300

tacgatatgg aagacccgct tcatgaggat gaagattcac cggtacccgg tctgacacac     360

cgctatcccg accgtgtgct gtttcttgtc acggatcaat gttccgtgta ctgccgccac     420

cgcacacgcc ggcgcttctc cggacaaatc ggaatgggcg tccccgaaaa acagcttgat     480

gctgcaattg cttacatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa catcatccgg tctggctgaa cacccatttt     720
```

-continued

```
aacacaagca tcgaaatgac agaagaatcc gttgaggcat atgaaaagct ggtgaacgcg    780

ggagtgccgg tcggaaatca ggctgttgta ttagcaggta ttaatgattc ggttccaatt    840

ataaaaaagc tcatgcatga cttggtaaaa atcagagtcc gtccttatta tatttaccaa    900

tgtgacctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa    1380

cagaaagaga ctgaatgcgg aggggattct tcataa                             1416
```

```
<210> SEQ ID NO 36
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 36

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Glu Asn
65                  70                  75                  80

Pro Arg Cys Pro Val Arg Met Gln Ser Val Pro Leu Pro Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asp Gln Cys Ser Val Tyr Cys Arg His Arg Thr Arg Arg
    130                 135                 140

Arg Phe Ser Gly Gln Ile Gly Met Gly Val Pro Glu Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys His His Pro Val Trp Leu Asn Thr His Phe
225                 230                 235                 240
```

-continued

```
Asn Thr Ser Ile Glu Met Thr Glu Glu Ser Val Glu Ala Tyr Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Ile Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 37
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 37

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacct tactatgctt ctttaatgga ccccgacaat    240

ccgagatgcc cggtacgcat gcagtctgtg ccgctttctg aagaaatgca caaaacaaaa     300

tacgatatgg aagacccgct tcatgaggat gaagattcac cggtacccgg tctgacacac     360

cgctatccca accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg actgtctgtt gtctggcggt     540

gatgggctgc tcatcaacga ccaaatttta gaatatattt taaaagagct gcgcagcatt     600

ccgcatctgg aagtcattcg tatcggttct cgtgcgccag tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat agggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg tcctgtcaca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtttac acctgaaaat   1260

gtagacagaa tcaaacggcg tgaggcatac atcgcaaatc cggagcatga aacattaaaa   1320

gatcggcgtg agaaaagaga tcagctcaaa gaaaagaaat ttttggcgca gcagaaaaaa   1380

cagaaagaga ctgaatgcgg aggggattct tcataa                              1416
```

```
<210> SEQ ID NO 38
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 38

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asn Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Leu Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Ser Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 39
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 39

atgaaaaaca aatggtataa accgaaacgg cattggaagg agatcgagtt atggaaggac     60

gttccggaag agaaatggaa cgattggctt tgacagctga cacacactgt aagaacgtta    120

gatgatttaa agaaagtcat taatctgacc gaggatgaag aggaaggcgt ccgtatttct    180

accaaaaacga tcccccttaaa tattacacct tactatgctt ctttaatgga ccccgacaat    240

ccgagatgcc cggtacgcat gcagtctgtg ccgctttctg aagaaatgca caaaacaaaa    300

tacgatatgg aagacccgct tcatgaggat gaagattcac cggtacccgg tctgacacac    360

cgctatcccg accgtgtgct gtttcttgtc acgaatcaat gttccgtgca ctgccgccac    420

tgcacacgcc ggcgcttttc cggacaaatc ggaatgggcg tccccaaaaa acagcttgat    480

gctgcaattg cttatatccg ggaaacaccc gaaatccgcg attgtttaat ttcaggcggt    540

gatgggctgc tcatcaacga ccaaatttta gaatatattt taaaagagct gcgcagcatt    600

ccgcacctgg aagtcatccg catcggaaca cgtgctcccg tcgtctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gtggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct ggcaaagaag tttcgtctac acctgaaaat   1260

gtagtcagaa tcaaacggcg tgaggcatac atcgcaaatc cggagcatga aacattaaaa   1320

gatcggcgtg agaaaagagg tcagctcaaa gaaaagaaat tttggcgca gcagaaaaaa   1380

cagaaagaga ctgaatgcgg aggggattct tcataa                             1416
```

<210> SEQ ID NO 40
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 40

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val His Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Gly Lys Glu Val Ser Ser
                405                 410                 415

Thr Pro Glu Asn Val Val Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 41
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 41

```
atgaaaaaca aatggtataa accgaaacgg cattggaagg agatcgagtt atggagggac     60

gtcccggaag agaaatggaa cgattggctt tgacagctga cacacactgt aagaacgtta    120

gatgatttaa agaaagtcat taatctgacc gaggatgaag aggaaggcgt ccgtatttct    180

accaaaaacga tcccccttaaa tattacacct tactatgctt ctttaatgga ccccgacaat    240

ccgaggtgcc cggtacgcat gcagtctgtg ccactgtctg aggaaatgca caaaagcaaa    300

tatgacatgg aagatccgct tcatgaggat gaagattcac cggtacccgg tctgacacac    360

cgctatcccg accgtgtgct gtttcttgtc acgaatcaat gttccgtgta ctgccgccac    420

tgcacacgcc ggcgcttttc cggacaaatc ggaatgggcg tccccaaaaa acagcttgat    480

gctgcaattg cttatatccg ggaaacaccc gaaatccgcg attgtttaat ttcaggcggt    540

gatgggctgc tcatcaacga ccaaatttta gaatatattt taaaagagct gcgcagcatt    600

ccgcatctgg aagtcatccg catcggaaca cgtgctcccg tcgtctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccgggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcgtac atcgcaaatc cggagcatga aacattaaaa   1320

gatcggcgtg agaaaagagg tcagctcaaa gaaaagaaat tttggcgca gcagaaaaaa   1380

cagaaagaga ctgaatgcgg aggggattct tcataa                             1416
```

```
<210> SEQ ID NO 42
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 42

Met Lys Asn Lys Trp Tyr Lys Pro Lys Arg His Trp Lys Glu Ile Glu
1               5                   10                  15

Leu Trp Arg Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Ser Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 43
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 43

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacca tactatgcga gcttaatgga tccagaaaac     240

ccacgttgtc cggtacgcat gcagtctgtg ccgctttccg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc cgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg     780

ggagtgccgg tcggaaatca ggctgtcgta ttagcaggta ttaatgattc ggttccaatt     840

atgaaaaagc tcatgcatga cttggtaaaa atcagagtcc gtccttatta tatttaccaa     900

tgtgatctgt cagaaggaat aaggcatttc cgtgctcctg tctccaaagg tttggagatc     960

attgaagggc tgagaggtca taccccaggc tatgcggttc ctacctttgt cgttcacgca    1020

ccaggcggag gaggtaaaat cgccctgcag ccgaactatg tcctgtctca aagtcctgac    1080

aaagtgatct taagaaattt tgaaggtgtg attacgtcat atccggaacc agagaattat    1140

atccccaatc aggcagacgc ctattttgag tccgtttccc ctgaaaccgc tgacaaaaag    1200

gagccgatcg ggctgagtgc catttttgct gacaaagaag tttcgtctac acctgaaaat    1260

gtagacagaa tcaaacggcg tgaggcctac atcgcaaatc cggagcatga aacattaaaa    1320

gatcggcgtg agaaaagagg tcagctcaaa gaaaagaaat tttcggcgca gcagaaaaaa    1380

cagaaagaga ctgaatgcgg aggggattct tcataa                              1416
```

<210> SEQ ID NO 44
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 44

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Glu Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Pro
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Pro Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Ser Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Ser Ala Gln Gln Lys Lys Gln Lys Glu Thr
    450                 455                 460

Glu Cys Gly Gly Asp Ser Ser
465                 470


<210> SEQ ID NO 45
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 45

atgaaaaaca aatggtataa accgaaacgg cattggaagg agatcgagtt acggaaggac     60

gttccggaag agaaatggaa cgattggctt tgacagctga cgcacactgt aagaacgtta    120

gatgatttaa agaaagtcat taatctgacc gaggatgaag aggaaggcgt ccgtatttct    180

accaaaacga tccccttaaa tattacacct tactatgcga gcttaattga tccagaaaac    240

ccacgttgtc cggtacgcat gcagtctgcg ccgctgtctg aagaaatgca caaaacaaaa    300

tacgatatgg aagacccgct tcatgaggat gaagattcac cggtacccgg tctgacacac    360

cgctatcccg accgtgtgct gtttcttgtc acgaatcaat gttccgtgta ctgccgccac    420

tgcacacgcc ggcgcttttc cggacaaatc ggaacgggcg tccccaaaaa acagcttgat    480

gctgcaactg cttatatccg ggaaacaccc gaaatccgcg attgtttaat tccaggcggt    540

gatgggctgc tcatcaacga ccaaatttta ggatatattt taaaagagct gcgcagcatt    600

ccgcatctgg aagtcatccg catcggaaca cgtgcccccg tcggctttcc gcagcgcatt    660

accgatcatc tgtgcgagat attgaaaaaa tatcatccgg tctggctgaa cacccatttt    720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca tacctcaggc tatgcggttc ctacctttgt cgttcacgca   1020

ccaggcggag gaggtaaaat cgccctgcag ccgaactatg ccctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa     1380

cagaaagaga ctgaatgcgg aggggattct tcataa                             1416


<210> SEQ ID NO 46
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 46

Met Lys Asn Lys Trp Tyr Lys Pro Lys Arg His Trp Lys Glu Ile Glu
1               5                   10                  15

Leu Arg Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Ile Asp Pro Glu Asn
65                  70                  75                  80

Pro Arg Cys Pro Val Arg Met Gln Ser Ala Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Thr Gly Val Pro Lys Lys Gln Leu Asp
145                 150                 155                 160

Ala Ala Thr Ala Tyr Ile Arg Glu Thr Pro Glu Ile Arg Asp Cys Leu
                165                 170                 175

Ile Pro Gly Gly Asp Gly Leu Leu Ile Asn Asp Gln Ile Leu Gly Tyr
            180                 185                 190

Ile Leu Lys Glu Leu Arg Ser Ile Pro His Leu Glu Val Ile Arg Ile
        195                 200                 205

Gly Thr Arg Ala Pro Val Gly Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

Asn Thr Ser Ile Glu Met Thr Glu Glu Ser Val Glu Ala Cys Glu Lys
245 250 255

Leu Val Asn Ala Gly Val Pro Val Gly Asn Gln Ala Val Val Leu Ala
260 265 270

Gly Ile Asn Asp Ser Val Pro Ile Met Lys Lys Leu Met His Asp Leu
275 280 285

Val Lys Ile Arg Val Arg Pro Tyr Tyr Ile Tyr Gln Cys Asp Leu Ser
290 295 300

Glu Gly Ile Arg His Phe Arg Ala Pro Val Ser Lys Gly Leu Glu Ile
305 310 315 320

Ile Glu Gly Leu Arg Gly His Thr Ser Gly Tyr Ala Val Pro Thr Phe
325 330 335

Val Val His Ala Pro Gly Gly Gly Gly Lys Ile Ala Leu Gln Pro Asn
340 345 350

Tyr Ala Leu Ser Gln Ser Pro Asp Lys Val Ile Leu Arg Asn Phe Glu
355 360 365

Gly Val Ile Thr Ser Tyr Pro Glu Pro Glu Asn Tyr Ile Pro Asn Gln
370 375 380

Ala Asp Ala Tyr Phe Glu Ser Val Phe Pro Glu Thr Ala Asp Lys Lys
385 390 395 400

Glu Pro Ile Gly Leu Ser Ala Ile Phe Ala Asp Lys Glu Val Ser Ser
405 410 415

Thr Pro Glu Asn Val Asp Arg Ile Lys Arg Arg Glu Ala Tyr Ile Ala
420 425 430

Asn Pro Glu His Glu Thr Leu Lys Asp Arg Arg Glu Lys Arg Gly Gln
435 440 445

Leu Lys Glu Lys Lys Phe Leu Ala Gln Gln Lys Lys Gln Lys Glu Thr
450 455 460

Glu Cys Gly Gly Asp Ser Ser
465 470

<210> SEQ ID NO 47
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 47
atggaaaaca aatggtataa accgaaacgg cattggaagg agatcgagtt atggaaggac 60
gttccggaag agaaatggaa cgattggctt tgacagctga cacacactgt aagaacgtta 120
gatgatttaa agaaagtcat taatctgacc gaggatgaag aggaaggcgt ccgtatttct 180 accaaaaacga tcccccttaaa tattacacct tactatgcga gcttaattga tccagaaaac 240
ccacgttgtc cggtacgcat gcagtctgtg ccgctttccg aagaaatgca caaaacaaaa 300
tacgatatgg aagatccgct tcatgaggat gaagattcac cggtacccgg cctgacacac 360
cgctatcccg accgtgtgct gtttcttgtc gcgaatcaat gttccgtgta ctgccgccac 420
tgcacacgcc ggcgcttttc cggacaaatc ggaatgggcg tccccaaaaa acagcttgat 480
gctgcaattg cttatatccg ggaaacaccc gaaatccgcg attgtttaat ttcaggcggt 540
gatgggctgc tcatcaacga ccaaatttta gaatatattt taaaagagct gcgcagcatt 600
ccgcatccgg aagtcatccg catcggaaca cgtgcccccg tcgtctttcc gcagcgcatt 660
accgatcatc tgtgcgagat attgaaaaaa tatcatccgg tctggctgaa cacccatttt 720

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgcccctg tttccaaagg tttggagatc    960

attgaagggc tgagaggtca tacctcaggc tgtgcggttc ctacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaacc aggcagacgc ctattttgag tccgttttcc ctgaaaccgc tgacaaaaag   1200

gagccgatcg ggctgagtgc cattttgct gacaaagaag tttcgtctac acctgaaaat   1260

gtagacagaa tcaaacggcg tgaggcatac atcgcaaatc cggagcatga aacattaaaa   1320

gatcggcgtg agaaaagggg tcagctcaaa gaaaagaaat ttttggcgca gcagaaaaaa   1380

cagaaagaga ctgaatgcgg aggggattct tcataa                             1416
```

<210> SEQ ID NO 48
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 48

```
Met Glu Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Ile Asp Pro Glu Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Ala Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Pro Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240
```

-continued

```
Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Cys Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 49
<211> LENGTH: 1416
<212> TYPE: DNA
<213> ORGANISM: Artificial Sequence
<220> FEATURE:
<223> OTHER INFORMATION: Synthetic construct - variant 2,3-aminomutase

<400> SEQUENCE: 49

atgaaaaaca aatggtataa accgaaacgg cattggaagg agatcgagtt atggaaggac      60

gttccggaag agaaatggaa cgattggctt tgacagctga cacacactgt aagaacgtta     120

gatgatttaa agaaagtcat taatctgacc gaggatgaag aggaaggcgt ccgtatttct     180

accaaaaacga tcccccttaaa tattacacct tactaggttt ctttaatgga ccccgacaat    240

ccgagatgcc cggtacgcat gcagtctgtg ccactgtctg aagaaatgca caaaacaaaa     300

tacgatatgg aagacccgct tcatgaggat gaagattcac cggtacccgg tctgacacac     360

cgctatcccg accgtgtgct gtttcttgtc acgaatcaat gttccgtgta ctgccgccac     420

tgcacacgcc ggcgcttttc cggacaaatc ggaatgggcg tccccaaaaa acagcttgat     480

gctgcaattg cttatatccg ggaaacaccc gaaatccgcg attgtttaat ttcaggcggt     540

gatgggctgc tcatcaacga ccaaatttta gaatatattt taaaagagct gcgcagcatt     600

ccgcatctgg aagtcatccg catcggaaca cgtgctcccg tcgtctttcc gcagcgcatt     660

accgatcatc tgtgcgagat attgaaaaaa tatcatccgg tctggctgaa cacccatttt     720
```

-continued

```
aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat aaggcatttc cgtgctcctg tttccaaagg tttggagatc    960

attgaagggc tgagaggtca cacctcaggc aatgcggttc ccacctttgt cgttcacgca   1020

ccaggcggag gaggtaaaat cgccctgcag ccgaactatg tcctgtctca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtctac acctgaaaat   1260

gtagacagaa tcaaacggcg tgaggcatac atcgcaaatc cggagcatga aacattaaaa   1320

gatcggcgtg agaaaagagg tcagctcaaa gaaaagaaat tttggcgca gcagaaaaaa   1380

cagaaagaga ctgaatgcgg aggggattct tcataa                              1416
```

<210> SEQ ID NO 50
<211> LENGTH: 71
<212> TYPE: PRT
<213> ORGANISM: Artificial Sequence
<220> FEATURE:
<223> OTHER INFORMATION: Synthetic construct - variant 2,3-aminomutase

<400> SEQUENCE: 50

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr
65                  70
```

<210> SEQ ID NO 51
<211> LENGTH: 399
<212> TYPE: PRT
<213> ORGANISM: Artificial Sequence
<220> FEATURE:
<223> OTHER INFORMATION: Synthetic construct - variant 2,3-aminomutase

<400> SEQUENCE: 51

```
Val Ser Leu Met Asp Pro Asp Asn Pro Arg Cys Pro Val Arg Met Gln
1               5                   10                  15

Ser Val Pro Leu Ser Glu Glu Met His Lys Thr Lys Tyr Asp Met Glu
            20                  25                  30

Asp Pro Leu His Glu Asp Glu Asp Ser Pro Val Pro Gly Leu Thr His
        35                  40                  45

Arg Tyr Pro Asp Arg Val Leu Phe Leu Val Thr Asn Gln Cys Ser Val
    50                  55                  60

Tyr Cys Arg His Cys Thr Arg Arg Arg Phe Ser Gly Gln Ile Gly Met
65                  70                  75                  80

Gly Val Pro Lys Lys Gln Leu Asp Ala Ala Ile Ala Tyr Ile Arg Glu
                85                  90                  95

Thr Pro Glu Ile Arg Asp Cys Leu Ile Ser Gly Gly Asp Gly Leu Leu
```

-continued

```
            100                 105                 110

Ile Asn Asp Gln Ile Leu Glu Tyr Ile Leu Lys Glu Leu Arg Ser Ile
        115                 120                 125

Pro His Leu Glu Val Ile Arg Ile Gly Thr Arg Ala Pro Val Val Phe
    130                 135                 140

Pro Gln Arg Ile Thr Asp His Leu Cys Glu Ile Leu Lys Lys Tyr His
145                 150                 155                 160

Pro Val Trp Leu Asn Thr His Phe Asn Thr Ser Ile Glu Met Thr Glu
                165                 170                 175

Glu Ser Val Glu Ala Cys Glu Lys Leu Val Asn Ala Gly Val Pro Val
            180                 185                 190

Gly Asn Gln Ala Val Val Leu Ala Gly Ile Asn Asp Ser Val Pro Ile
        195                 200                 205

Met Lys Lys Leu Met His Asp Leu Val Lys Ile Arg Val Arg Pro Tyr
    210                 215                 220

Tyr Ile Tyr Gln Cys Asp Leu Ser Glu Gly Ile Arg His Phe Arg Ala
225                 230                 235                 240

Pro Val Ser Lys Gly Leu Glu Ile Ile Glu Gly Leu Arg Gly His Thr
                245                 250                 255

Ser Gly Asn Ala Val Pro Thr Phe Val Val His Ala Pro Gly Gly Gly
            260                 265                 270

Gly Lys Ile Ala Leu Gln Pro Asn Tyr Val Leu Ser Gln Ser Pro Asp
        275                 280                 285

Lys Val Ile Leu Arg Asn Phe Glu Gly Val Ile Thr Ser Tyr Pro Glu
    290                 295                 300

Pro Glu Asn Tyr Ile Pro Asn Gln Ala Asp Ala Tyr Phe Glu Ser Val
305                 310                 315                 320

Phe Pro Glu Thr Ala Asp Lys Lys Glu Pro Ile Gly Leu Ser Ala Ile
                325                 330                 335

Phe Ala Asp Lys Glu Val Ser Ser Thr Pro Glu Asn Val Asp Arg Ile
            340                 345                 350

Lys Arg Arg Glu Ala Tyr Ile Ala Asn Pro Glu His Glu Thr Leu Lys
        355                 360                 365

Asp Arg Arg Glu Lys Arg Gly Gln Leu Lys Glu Lys Lys Phe Leu Ala
    370                 375                 380

Gln Gln Lys Lys Gln Lys Glu Thr Glu Cys Gly Gly Asp Ser Ser
385                 390                 395


<210> SEQ ID NO 52
<211> LENGTH: 1245
<212> TYPE: DNA
<213> ORGANISM: Artificial Sequence
<220> FEATURE:
<223> OTHER INFORMATION: Synthetic construct - variant 2,3-aminomutase
<220> FEATURE:
<221> NAME/KEY: misc_feature
<223> OTHER INFORMATION: This parental sequence is a modification of
      the wild-type KAM of Clostridium stricklandii
<220> FEATURE:
<221> NAME/KEY: CDS
<222> LOCATION: (1)..(1245)

<400> SEQUENCE: 52

atg agt tta aag gat aag ttt ttt aca cat gta agc caa gaa gat tgg       48
Met Ser Leu Lys Asp Lys Phe Phe Thr His Val Ser Gln Glu Asp Trp
1               5                   10                  15

aat gat tgg aaa tgg caa gta aga aat cgt ata aag act gtt gaa gaa       96
Asn Asp Trp Lys Trp Gln Val Arg Asn Arg Ile Lys Thr Val Glu Glu
```

-continued

```
            20                  25                  30

ctt aaa aaa tat att cca ctt act cca gaa gaa gaa gaa ggg gta aaa      144
Leu Lys Lys Tyr Ile Pro Leu Thr Pro Glu Glu Glu Glu Gly Val Lys
        35                  40                  45

cgc tgt ctt gat aca tta cgt atg gct att act cca tac tat cta tcg      192
Arg Cys Leu Asp Thr Leu Arg Met Ala Ile Thr Pro Tyr Tyr Leu Ser
    50                  55                  60

cta att gat gta gaa aat cca aat gac cct gta aga aag caa gct gta      240
Leu Ile Asp Val Glu Asn Pro Asn Asp Pro Val Arg Lys Gln Ala Val
65                  70                  75                  80

cct ctt tct tta gag ctg cat cgc gca gcg tct gat atg gaa gac cca      288
Pro Leu Ser Leu Glu Leu His Arg Ala Ala Ser Asp Met Glu Asp Pro
                85                  90                  95

ctt cat gaa gat gga gat tct cca gtt cca gga ctt aca cat cgc tat      336
Leu His Glu Asp Gly Asp Ser Pro Val Pro Gly Leu Thr His Arg Tyr
            100                 105                 110

cct gat cgc gtt ctt ctt tta atg act gat caa tgt tca gta tac tgc      384
Pro Asp Arg Val Leu Leu Leu Met Thr Asp Gln Cys Ser Val Tyr Cys
        115                 120                 125

cgc cac tgt act cgt aga cgc ttc gct ggt cga aca gat tct gct gtt      432
Arg His Cys Thr Arg Arg Arg Phe Ala Gly Arg Thr Asp Ser Ala Val
    130                 135                 140

gat acg aag caa ata gat gct gcg att gaa tat atc aaa aat act cca      480
Asp Thr Lys Gln Ile Asp Ala Ala Ile Glu Tyr Ile Lys Asn Thr Pro
145                 150                 155                 160

caa gta aga gac gtt cta ctt tca gga gga gat gct cta tta atc tca      528
Gln Val Arg Asp Val Leu Leu Ser Gly Gly Asp Ala Leu Leu Ile Ser
                165                 170                 175

gat gaa aag ctt gag tac aca atc aga aga ctt cgt gaa ata cca cac      576
Asp Glu Lys Leu Glu Tyr Thr Ile Arg Arg Leu Arg Glu Ile Pro His
            180                 185                 190

gtt gag gtt att cgt att gga tca cgt gta cca gtt gta atg cca caa      624
Val Glu Val Ile Arg Ile Gly Ser Arg Val Pro Val Val Met Pro Gln
        195                 200                 205

cgt att aca cca gaa cta gtt tct atg ctt aaa aag tat cat cca gta      672
Arg Ile Thr Pro Glu Leu Val Ser Met Leu Lys Lys Tyr His Pro Val
    210                 215                 220

tgg tta aat aca cac ttc aac cat cct aat gaa att act gaa gag tct      720
Trp Leu Asn Thr His Phe Asn His Pro Asn Glu Ile Thr Glu Glu Ser
225                 230                 235                 240

aaa cgt gca tgt gag tta ctt gct gat gca ggt att cct ctt gga aat      768
Lys Arg Ala Cys Glu Leu Leu Ala Asp Ala Gly Ile Pro Leu Gly Asn
                245                 250                 255

caa agt gtg ctt ctt gca ggt gta aat gat tgc atg cac gtt atg aaa      816
Gln Ser Val Leu Leu Ala Gly Val Asn Asp Cys Met His Val Met Lys
            260                 265                 270

aaa cta gta aat gac tta gtt aaa ata cgc gta cgt cct tac tat att      864
Lys Leu Val Asn Asp Leu Val Lys Ile Arg Val Arg Pro Tyr Tyr Ile
        275                 280                 285

tat caa tgt gac ctt tca gtt gga att gag cac ttt cgc act cca gtt      912
Tyr Gln Cys Asp Leu Ser Val Gly Ile Glu His Phe Arg Thr Pro Val
    290                 295                 300

gca aag gga ata gaa ata att gaa ggc tta aga gga cat act tca gga      960
Ala Lys Gly Ile Glu Ile Ile Glu Gly Leu Arg Gly His Thr Ser Gly
305                 310                 315                 320

tac tgc gtt cct aca ttt gtt gtg cat gca cct ggt ggt gga gga aaa     1008
Tyr Cys Val Pro Thr Phe Val Val His Ala Pro Gly Gly Gly Gly Lys
                325                 330                 335

act cca gtt atg cca aac tat gtt att tca caa aat cac aat aaa gtt     1056
```

-continued

```
Thr Pro Val Met Pro Asn Tyr Val Ile Ser Gln Asn His Asn Lys Val
            340                 345                 350

att tta cgt aac ttt gaa ggt gta att aca act tac gat gag cct gat      1104
Ile Leu Arg Asn Phe Glu Gly Val Ile Thr Thr Tyr Asp Glu Pro Asp
        355                 360                 365

cat tat act ttc cac tgt gac tgt gat gta tgc act gga aaa aca aat      1152
His Tyr Thr Phe His Cys Asp Cys Asp Val Cys Thr Gly Lys Thr Asn
    370                 375                 380

gtt cat aag gtt gga gta gct gga ctt cta aat gga gag aca gcg aca      1200
Val His Lys Val Gly Val Ala Gly Leu Leu Asn Gly Glu Thr Ala Thr
385                 390                 395                 400

ctt gaa cct gag ggt ttg gaa aga aaa caa aga gga cat cac taa          1245
Leu Glu Pro Glu Gly Leu Glu Arg Lys Gln Arg Gly His His
                405                 410


<210> SEQ ID NO 53
<211> LENGTH: 414
<212> TYPE: PRT
<213> ORGANISM: Artificial Sequence
<220> FEATURE:
<223> OTHER INFORMATION: Synthetic construct - variant 2,3-aminomutase

<400> SEQUENCE: 53

Met Ser Leu Lys Asp Lys Phe Phe Thr His Val Ser Gln Glu Asp Trp
1               5                   10                  15

Asn Asp Trp Lys Trp Gln Val Arg Asn Arg Ile Lys Thr Val Glu Glu
            20                  25                  30

Leu Lys Lys Tyr Ile Pro Leu Thr Pro Glu Glu Glu Glu Gly Val Lys
        35                  40                  45

Arg Cys Leu Asp Thr Leu Arg Met Ala Ile Thr Pro Tyr Tyr Leu Ser
    50                  55                  60

Leu Ile Asp Val Glu Asn Pro Asn Asp Pro Val Arg Lys Gln Ala Val
65                  70                  75                  80

Pro Leu Ser Leu Glu Leu His Arg Ala Ala Ser Asp Met Glu Asp Pro
                85                  90                  95

Leu His Glu Asp Gly Asp Ser Pro Val Pro Gly Leu Thr His Arg Tyr
            100                 105                 110

Pro Asp Arg Val Leu Leu Leu Met Thr Asp Gln Cys Ser Val Tyr Cys
        115                 120                 125

Arg His Cys Thr Arg Arg Arg Phe Ala Gly Arg Thr Asp Ser Ala Val
    130                 135                 140

Asp Thr Lys Gln Ile Asp Ala Ala Ile Glu Tyr Ile Lys Asn Thr Pro
145                 150                 155                 160

Gln Val Arg Asp Val Leu Leu Ser Gly Gly Asp Ala Leu Leu Ile Ser
                165                 170                 175

Asp Glu Lys Leu Glu Tyr Thr Ile Arg Arg Leu Arg Glu Ile Pro His
            180                 185                 190

Val Glu Val Ile Arg Ile Gly Ser Arg Val Pro Val Val Met Pro Gln
        195                 200                 205

Arg Ile Thr Pro Glu Leu Val Ser Met Leu Lys Lys Tyr His Pro Val
    210                 215                 220

Trp Leu Asn Thr His Phe Asn His Pro Asn Glu Ile Thr Glu Glu Ser
225                 230                 235                 240

Lys Arg Ala Cys Glu Leu Leu Ala Asp Ala Gly Ile Pro Leu Gly Asn
                245                 250                 255

Gln Ser Val Leu Leu Ala Gly Val Asn Asp Cys Met His Val Met Lys
            260                 265                 270
```

-continued

```
Lys Leu Val Asn Asp Leu Val Lys Ile Arg Val Arg Pro Tyr Tyr Ile
        275                 280                 285

Tyr Gln Cys Asp Leu Ser Val Gly Ile Glu His Phe Arg Thr Pro Val
    290                 295                 300

Ala Lys Gly Ile Glu Ile Ile Glu Gly Leu Arg Gly His Thr Ser Gly
305                 310                 315                 320

Tyr Cys Val Pro Thr Phe Val Val His Ala Pro Gly Gly Gly Gly Lys
                325                 330                 335

Thr Pro Val Met Pro Asn Tyr Val Ile Ser Gln Asn His Asn Lys Val
            340                 345                 350

Ile Leu Arg Asn Phe Glu Gly Val Ile Thr Thr Tyr Asp Glu Pro Asp
        355                 360                 365

His Tyr Thr Phe His Cys Asp Cys Asp Val Cys Thr Gly Lys Thr Asn
    370                 375                 380

Val His Lys Val Gly Val Ala Gly Leu Leu Asn Gly Glu Thr Ala Thr
385                 390                 395                 400

Leu Glu Pro Glu Gly Leu Glu Arg Lys Gln Arg Gly His His
                405                 410


<210> SEQ ID NO 54
<211> LENGTH: 1251
<212> TYPE: DNA
<213> ORGANISM: Artificial Sequence
<220> FEATURE:
<223> OTHER INFORMATION: Synthetic construct - variant 2,3-aminomutase
<220> FEATURE:
<221> NAME/KEY: CDS
<222> LOCATION: (1)..(1251)

<400> SEQUENCE: 54

atg gca gaa agt cgt aga aag tat tat ttc cct gat gtc acc gat gag       48
Met Ala Glu Ser Arg Arg Lys Tyr Tyr Phe Pro Asp Val Thr Asp Glu
1               5                   10                  15

caa tgg tac gac tgg cat tgg cag gtc ctc aat cga att aag acg ctc       96
Gln Trp Tyr Asp Trp His Trp Gln Val Leu Asn Arg Ile Lys Thr Leu
            20                  25                  30

gac cag ctg aaa aag tac gtt aca ctc acc gct gaa gaa gaa gag gga      144
Asp Gln Leu Lys Lys Tyr Val Thr Leu Thr Ala Glu Glu Glu Glu Gly
        35                  40                  45

gta aaa gaa tcg ccc aaa gta ctc cga atg gct atc aca cct tat tat      192
Val Lys Glu Ser Pro Lys Val Leu Arg Met Ala Ile Thr Pro Tyr Tyr
    50                  55                  60

ttg agt ttg ata gac ccc gag aat cct aat tgt ccg att cgt aaa caa      240
Leu Ser Leu Ile Asp Pro Glu Asn Pro Asn Cys Pro Ile Arg Lys Gln
65                  70                  75                  80

gcc att cct act caa cag gaa ctg gta cgt gct cct gaa gat cag gta      288
Ala Ile Pro Thr Gln Gln Glu Leu Val Arg Ala Pro Glu Asp Gln Val
                85                  90                  95

gac cca ctt agt gaa gat gaa gat tcg ccc gta ccc gga ctg act cat      336
Asp Pro Leu Ser Glu Asp Glu Asp Ser Pro Val Pro Gly Leu Thr His
            100                 105                 110

cgt tat ccg gat cgt gta ttg ttc ctt atc acg gac aaa tgt tcg atg      384
Arg Tyr Pro Asp Arg Val Leu Phe Leu Ile Thr Asp Lys Cys Ser Met
        115                 120                 125

tac tgt cgt cat tgt act cgc cgt cgc ttc gca gga cag aaa gat gct      432
Tyr Cys Arg His Cys Thr Arg Arg Arg Phe Ala Gly Gln Lys Asp Ala
    130                 135                 140

tct tct cct tct gag cgc atc gat cga tgc att gac tat ata gcc aat      480
Ser Ser Pro Ser Glu Arg Ile Asp Arg Cys Ile Asp Tyr Ile Ala Asn
```

-continued

```
145                 150                 155                 160

aca ccg aca gtc cgc gat gtt ttg cta tcg gga ggc gat gcc ctc ctt      528
Thr Pro Thr Val Arg Asp Val Leu Leu Ser Gly Gly Asp Ala Leu Leu
                165                 170                 175

gtc agc gac gaa cgc ttg gaa tac ata ttg aag cgt ctg cgc gaa gta      576
Val Ser Asp Glu Arg Leu Glu Tyr Ile Leu Lys Arg Leu Arg Glu Val
            180                 185                 190

cct cat gtg gag att gtt cgt ata gga agc cgt acg ccg gta gtc ctc      624
Pro His Val Glu Ile Val Arg Ile Gly Ser Arg Thr Pro Val Val Leu
        195                 200                 205

cct cag cgt ata acg cct caa ttg gtg gat atg ctc aaa aaa tat cat      672
Pro Gln Arg Ile Thr Pro Gln Leu Val Asp Met Leu Lys Lys Tyr His
    210                 215                 220

ccg gtg tgg ctg aac act cac ttc aac cac ccg aat gaa gtt acc gaa      720
Pro Val Trp Leu Asn Thr His Phe Asn His Pro Asn Glu Val Thr Glu
225                 230                 235                 240

gaa gca gtg gag gct tgt gaa aga atg gcc aat gcc ggt att ccg ttg      768
Glu Ala Val Glu Ala Cys Glu Arg Met Ala Asn Ala Gly Ile Pro Leu
                245                 250                 255

ggt aac caa acg gtt tta ttg cgt gga atc aat gat tgt aca cat gtg      816
Gly Asn Gln Thr Val Leu Leu Arg Gly Ile Asn Asp Cys Thr His Val
            260                 265                 270

atg aag aga ttg gta cat ttg ctg gta aag atg cgt gtg cgt cct tac      864
Met Lys Arg Leu Val His Leu Leu Val Lys Met Arg Val Arg Pro Tyr
        275                 280                 285

tat ata tat gta tgc gat ctt tcg ctt gga ata ggt cat ttc cgc acg      912
Tyr Ile Tyr Val Cys Asp Leu Ser Leu Gly Ile Gly His Phe Arg Thr
    290                 295                 300

ccg gta tct aaa gga atc gaa att atc gaa aat ttg cgc gga cac acc      960
Pro Val Ser Lys Gly Ile Glu Ile Ile Glu Asn Leu Arg Gly His Thr
305                 310                 315                 320

tcg ggc tat gca gtt cct acc ttt gtg gta ggt gct ccg ggg ggt ggt     1008
Ser Gly Tyr Ala Val Pro Thr Phe Val Val Gly Ala Pro Gly Gly Gly
                325                 330                 335

ggt aag ata cct gta acg ccg aac tat gtt gta tct cag tcc cca cga     1056
Gly Lys Ile Pro Val Thr Pro Asn Tyr Val Val Ser Gln Ser Pro Arg
            340                 345                 350

cat gtg gtt ctt cgc aat tat gaa ggt gtt atc aca acc tat acg gag     1104
His Val Val Leu Arg Asn Tyr Glu Gly Val Ile Thr Thr Tyr Thr Glu
        355                 360                 365

ccg gag aat tat cat gag gag tgc gat tgt gag gac tgt cga gcc ggt     1152
Pro Glu Asn Tyr His Glu Glu Cys Asp Cys Glu Asp Cys Arg Ala Gly
    370                 375                 380

aag cat aaa gag ggt gta gct gca ctt tcc gga ggt cag cag ttg gct     1200
Lys His Lys Glu Gly Val Ala Ala Leu Ser Gly Gly Gln Gln Leu Ala
385                 390                 395                 400

atc gag cct tcc gac tta gct cgc aaa aaa cgc aag ttt gat aag aac     1248
Ile Glu Pro Ser Asp Leu Ala Arg Lys Lys Arg Lys Phe Asp Lys Asn
                405                 410                 415

taa                                                                 1251

<210> SEQ ID NO 55
<211> LENGTH: 416
<212> TYPE: PRT
<213> ORGANISM: Artificial Sequence
<220> FEATURE:
<223> OTHER INFORMATION: Synthetic construct - variant 2,3-aminomutase

<400> SEQUENCE: 55

Met Ala Glu Ser Arg Arg Lys Tyr Tyr Phe Pro Asp Val Thr Asp Glu
```

-continued

```
1               5                   10                  15

Gln Trp Tyr Asp Trp His Trp Gln Val Leu Asn Arg Ile Lys Thr Leu
            20                  25                  30

Asp Gln Leu Lys Lys Tyr Val Thr Leu Thr Ala Glu Glu Glu Glu Gly
        35                  40                  45

Val Lys Glu Ser Pro Lys Val Leu Arg Met Ala Ile Thr Pro Tyr Tyr
    50                  55                  60

Leu Ser Leu Ile Asp Pro Glu Asn Pro Asn Cys Pro Ile Arg Lys Gln
65                  70                  75                  80

Ala Ile Pro Thr Gln Gln Glu Leu Val Arg Ala Pro Glu Asp Gln Val
                85                  90                  95

Asp Pro Leu Ser Glu Asp Glu Asp Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Arg Phe Ala Gly Gln Lys Asp Ala
    130                 135                 140

Ser Ser Pro Ser Glu Arg Ile Asp Arg Cys Ile Asp Tyr Ile Ala Asn
145                 150                 155                 160

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Val
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
225                 230                 235                 240

Glu Ala Val Glu Ala Cys Glu Arg Met Ala Asn Ala Gly Ile Pro Leu
                245                 250                 255

Gly Asn Gln Thr Val Leu Leu Arg Gly Ile Asn Asp Cys Thr His Val
            260                 265                 270

Met Lys Arg Leu Val His Leu Leu Val Lys Met Arg Val Arg Pro Tyr
        275                 280                 285

Tyr Ile Tyr Val Cys Asp Leu Ser Leu Gly Ile Gly His Phe Arg Thr
    290                 295                 300

Pro Val Ser Lys Gly Ile Glu Ile Ile Glu Asn Leu Arg Gly His Thr
305                 310                 315                 320

Ser Gly Tyr Ala Val Pro Thr Phe Val Val Gly Ala Pro Gly Gly Gly
                325                 330                 335

Gly Lys Ile Pro Val Thr Pro Asn Tyr Val Val Ser Gln Ser Pro Arg
            340                 345                 350

His Val Val Leu Arg Asn Tyr Glu Gly Val Ile Thr Thr Tyr Thr Glu
        355                 360                 365

Pro Glu Asn Tyr His Glu Glu Cys Asp Cys Glu Asp Cys Arg Ala Gly
    370                 375                 380

Lys His Lys Glu Gly Val Ala Ala Leu Ser Gly Gly Gln Gln Leu Ala
385                 390                 395                 400

Ile Glu Pro Ser Asp Leu Ala Arg Lys Lys Arg Lys Phe Asp Lys Asn
                405                 410                 415
```

<210> SEQ ID NO 56

-continued

<211> LENGTH: 1278
<212> TYPE: DNA
<213> ORGANISM: Artificial Sequence
<220> FEATURE:
<223> OTHER INFORMATION: Synthetic construct - variant 2,3-aminomutase
<220> FEATURE:
<221> NAME/KEY: CDS
<222> LOCATION: (1)..(1278)

<400> SEQUENCE: 56

```
atg aat aca gtt aat act cgt aaa aaa ttt ttc cca aat gta act gat       48
Met Asn Thr Val Asn Thr Arg Lys Lys Phe Phe Pro Asn Val Thr Asp
1               5                   10                  15

gaa gaa tgg aat gat tgg aca tgg caa gta aaa aac cgc ctt aaa agt       96
Glu Glu Trp Asn Asp Trp Thr Trp Gln Val Lys Asn Arg Leu Lys Ser
            20                  25                  30

gtt gaa gat tta gaa aaa tat gtt gat tta agt gaa gaa gaa aca gaa      144
Val Glu Asp Leu Glu Lys Tyr Val Asp Leu Ser Glu Glu Glu Thr Glu
        35                  40                  45

ggg gtt gta cgc act ctt gaa act tta cgt atg gca atc act cca ttt      192
Gly Val Val Arg Thr Leu Glu Thr Leu Arg Met Ala Ile Thr Pro Phe
    50                  55                  60

tac ttc tca ttg ata gat ttg aat agt gat cgc tgc cca ata cgt aag      240
Tyr Phe Ser Leu Ile Asp Leu Asn Ser Asp Arg Cys Pro Ile Arg Lys
65                  70                  75                  80

caa gct ata cct act ata cga gaa ata cat caa tct gat gct gat atg      288
Gln Ala Ile Pro Thr Ile Arg Glu Ile His Gln Ser Asp Ala Asp Met
                85                  90                  95

ttg gat cct cta cat gaa gat gaa gac tct cca gta cca gga tta act      336
Leu Asp Pro Leu His Glu Asp Glu Asp Ser Pro Val Pro Gly Leu Thr
            100                 105                 110

cat cgc tat cca gat cgt gtt tta ctt cta ata aca gac atg tgt tct      384
His Arg Tyr Pro Asp Arg Val Leu Leu Leu Ile Thr Asp Met Cys Ser
        115                 120                 125

gta tac tgt cgc cac tgc act cgt cgc aga ttt gct ggg tca agt gat      432
Val Tyr Cys Arg His Cys Thr Arg Arg Arg Phe Ala Gly Ser Ser Asp
    130                 135                 140

ggt gct atg cct atg gat aga att gac aaa gca ata gaa tat att gca      480
Gly Ala Met Pro Met Asp Arg Ile Asp Lys Ala Ile Glu Tyr Ile Ala
145                 150                 155                 160

aaa act cca caa gta agg gat gta ttg tta tca gga gga gat gca ctt      528
Lys Thr Pro Gln Val Arg Asp Val Leu Leu Ser Gly Gly Asp Ala Leu
                165                 170                 175

cta gtt tct aat aaa aaa tta gaa agc ata atc caa aaa cta cgc gca      576
Leu Val Ser Asn Lys Lys Leu Glu Ser Ile Ile Gln Lys Leu Arg Ala
            180                 185                 190

ata cct cat gtt gaa ata atc aga ata gga agt cgt aca cca gtt gtt      624
Ile Pro His Val Glu Ile Ile Arg Ile Gly Ser Arg Thr Pro Val Val
        195                 200                 205

tta cct caa aga att act cct gaa tta tgt aat atg tta aag aaa tat      672
Leu Pro Gln Arg Ile Thr Pro Glu Leu Cys Asn Met Leu Lys Lys Tyr
    210                 215                 220

cat cca att tgg atg aat act cat ttt aac cac cct caa gaa gta acg      720
His Pro Ile Trp Met Asn Thr His Phe Asn His Pro Gln Glu Val Thr
225                 230                 235                 240

cca gaa gct aaa aaa gct tgt gaa atg ttg gca gat gca gga gtt cca      768
Pro Glu Ala Lys Lys Ala Cys Glu Met Leu Ala Asp Ala Gly Val Pro
                245                 250                 255

tta gga aat caa act gta cta tta aga gga ata aat gac agt gta cct      816
Leu Gly Asn Gln Thr Val Leu Leu Arg Gly Ile Asn Asp Ser Val Pro
            260                 265                 270
```

-continued

```
gta atg aaa agg tta gta cat gat tta gta atg atg cgt gta cgc cct      864
Val Met Lys Arg Leu Val His Asp Leu Val Met Met Arg Val Arg Pro
        275                 280                 285

tat tat att tac caa tgt gac tta tct atg gga ctc gaa cac ttc cgc      912
Tyr Tyr Ile Tyr Gln Cys Asp Leu Ser Met Gly Leu Glu His Phe Arg
    290                 295                 300

aca cca gtt tct aaa ggt ata gaa att att gaa gga tta cgt gga cat      960
Thr Pro Val Ser Lys Gly Ile Glu Ile Ile Glu Gly Leu Arg Gly His
305                 310                 315                 320

aca tct gga tat gca gta cca aca ttt gtt gtg cat gca cct ggt ggt     1008
Thr Ser Gly Tyr Ala Val Pro Thr Phe Val Val His Ala Pro Gly Gly
                325                 330                 335

gga gga aaa act cca gta atg cct caa tat gta att tct caa tct cct     1056
Gly Gly Lys Thr Pro Val Met Pro Gln Tyr Val Ile Ser Gln Ser Pro
            340                 345                 350

cat cgt gta gtt tta cgc aac ttt gaa gga gtt ata aca act tat aca     1104
His Arg Val Val Leu Arg Asn Phe Glu Gly Val Ile Thr Thr Tyr Thr
        355                 360                 365

gaa cca gaa aat tat aca cat gaa cct tgt tat gat gaa gaa aaa ttt     1152
Glu Pro Glu Asn Tyr Thr His Glu Pro Cys Tyr Asp Glu Glu Lys Phe
    370                 375                 380

gaa aaa atg tat gaa ata agt gga gtt tat atg cta gat gaa gga tta     1200
Glu Lys Met Tyr Glu Ile Ser Gly Val Tyr Met Leu Asp Glu Gly Leu
385                 390                 395                 400

gaa atg tca cta gaa cct agc cac tta gca cgt cat gaa cgc aat aaa     1248
Glu Met Ser Leu Glu Pro Ser His Leu Ala Arg His Glu Arg Asn Lys
                405                 410                 415

aag aga gca gaa gct gaa ggg aaa aaa taa                             1278
Lys Arg Ala Glu Ala Glu Gly Lys Lys
            420                 425


<210> SEQ ID NO 57
<211> LENGTH: 425
<212> TYPE: PRT
<213> ORGANISM: Artificial Sequence
<220> FEATURE:
<223> OTHER INFORMATION: Synthetic construct - variant 2,3-aminomutase

<400> SEQUENCE: 57

Met Asn Thr Val Asn Thr Arg Lys Lys Phe Phe Pro Asn Val Thr Asp
1               5                   10                  15

Glu Glu Trp Asn Asp Trp Thr Trp Gln Val Lys Asn Arg Leu Lys Ser
            20                  25                  30

Val Glu Asp Leu Glu Lys Tyr Val Asp Leu Ser Glu Glu Glu Thr Glu
        35                  40                  45

Gly Val Val Arg Thr Leu Glu Thr Leu Arg Met Ala Ile Thr Pro Phe
    50                  55                  60

Tyr Phe Ser Leu Ile Asp Leu Asn Ser Asp Arg Cys Pro Ile Arg Lys
65                  70                  75                  80

Gln Ala Ile Pro Thr Ile Arg Glu Ile His Gln Ser Asp Ala Asp Met
                85                  90                  95

Leu Asp Pro Leu His Glu Asp Glu Asp Ser Pro Val Pro Gly Leu Thr
            100                 105                 110

His Arg Tyr Pro Asp Arg Val Leu Leu Leu Ile Thr Asp Met Cys Ser
        115                 120                 125

Val Tyr Cys Arg His Cys Thr Arg Arg Arg Phe Ala Gly Ser Ser Asp
    130                 135                 140

Gly Ala Met Pro Met Asp Arg Ile Asp Lys Ala Ile Glu Tyr Ile Ala
145                 150                 155                 160
```

-continued

```
Lys Thr Pro Gln Val Arg Asp Val Leu Leu Ser Gly Gly Asp Ala Leu
                165                 170                 175

Leu Val Ser Asn Lys Lys Leu Glu Ser Ile Ile Gln Lys Leu Arg Ala
            180                 185                 190

Ile Pro His Val Glu Ile Ile Arg Ile Gly Ser Arg Thr Pro Val Val
        195                 200                 205

Leu Pro Gln Arg Ile Thr Pro Glu Leu Cys Asn Met Leu Lys Lys Tyr
    210                 215                 220

His Pro Ile Trp Met Asn Thr His Phe Asn His Pro Gln Glu Val Thr
225                 230                 235                 240

Pro Glu Ala Lys Lys Ala Cys Glu Met Leu Ala Asp Ala Gly Val Pro
                245                 250                 255

Leu Gly Asn Gln Thr Val Leu Leu Arg Gly Ile Asn Asp Ser Val Pro
            260                 265                 270

Val Met Lys Arg Leu Val His Asp Leu Val Met Met Arg Val Arg Pro
        275                 280                 285

Tyr Tyr Ile Tyr Gln Cys Asp Leu Ser Met Gly Leu Glu His Phe Arg
    290                 295                 300

Thr Pro Val Ser Lys Gly Ile Glu Ile Ile Glu Gly Leu Arg Gly His
305                 310                 315                 320

Thr Ser Gly Tyr Ala Val Pro Thr Phe Val Val His Ala Pro Gly Gly
                325                 330                 335

Gly Gly Lys Thr Pro Val Met Pro Gln Tyr Val Ile Ser Gln Ser Pro
            340                 345                 350

His Arg Val Val Leu Arg Asn Phe Glu Gly Val Ile Thr Thr Tyr Thr
        355                 360                 365

Glu Pro Glu Asn Tyr Thr His Glu Pro Cys Tyr Asp Glu Glu Lys Phe
    370                 375                 380

Glu Lys Met Tyr Glu Ile Ser Gly Val Tyr Met Leu Asp Glu Gly Leu
385                 390                 395                 400

Glu Met Ser Leu Glu Pro Ser His Leu Ala Arg His Glu Arg Asn Lys
                405                 410                 415

Lys Arg Ala Glu Ala Glu Gly Lys Lys
            420                 425
```

```
<210> SEQ ID NO 58
<211> LENGTH: 1416
<212> TYPE: DNA
<213> ORGANISM: Artificial Sequence
<220> FEATURE:
<223> OTHER INFORMATION: Synthetic construct - variant 2,3-aminomutase
<220> FEATURE:
<221> NAME/KEY: CDS
<222> LOCATION: (1)..(1416)

<400> SEQUENCE: 58

atg aaa aac aaa tgg tat aaa ccg aaa cgg cat tgg aag gag atc gag       48
Met Lys Asn Lys Trp Tyr Lys Pro Lys Arg His Trp Lys Glu Ile Glu
1               5                   10                  15

tta tgg aag gac gtt ccg gaa gag aaa tgg aac gat tgg ctt tgg cag       96
Leu Trp Lys Asp Val Pro Glu Glu Lys Trp Asn Asp Trp Leu Trp Gln
            20                  25                  30

ctg aca cac act gta aga acg tta gat gat tta aag aaa gtc att aat      144
Leu Thr His Thr Val Arg Thr Leu Asp Asp Leu Lys Lys Val Ile Asn
        35                  40                  45

ctg acc gag gat gaa gag gaa ggc gtc cgt att tct acc aaa acg atc      192
Leu Thr Glu Asp Glu Glu Glu Gly Val Arg Ile Ser Thr Lys Thr Ile
```

-continued

```
    50                  55                  60

ccc tta aat att aca cct tac tat gct tct tta atg gac ccc gac aat      240
Pro Leu Asn Ile Thr Pro Tyr Tyr Ala Ser Leu Met Asp Pro Asp Asn
65                  70                  75                  80

ccg aga tgc ccg gta cgc atg cag tct gtg ccg ctt tct gaa gaa atg      288
Pro Arg Cys Pro Val Arg Met Gln Ser Val Pro Leu Ser Glu Glu Met
                85                  90                  95

cac aaa aca aaa tac gat atg gaa gac ccg ctt cat gag gat gaa gat      336
His Lys Thr Lys Tyr Asp Met Glu Asp Pro Leu His Glu Asp Glu Asp
            100                 105                 110

tca ccg gta ccc ggt ctg aca cac cgc tat ccc gac cgt gtg ctg ttt      384
Ser Pro Val Pro Gly Leu Thr His Arg Tyr Pro Asp Arg Val Leu Phe
        115                 120                 125

ctt gtc acg aat caa tgt tcc gtg tac tgc cgc cac tgc aca cgc cgg      432
Leu Val Thr Asn Gln Cys Ser Val Tyr Cys Arg His Cys Thr Arg Arg
    130                 135                 140

cgc ttt tcc gga caa atc gga atg ggc gtc ccc aaa aaa cag ctt gat      480
Arg Phe Ser Gly Gln Ile Gly Met Gly Val Pro Lys Lys Gln Leu Asp
145                 150                 155                 160

gct gca att gct tat atc cgg gaa aca ccc gaa atc cgc gat tgt tta      528
Ala Ala Ile Ala Tyr Ile Arg Glu Thr Pro Glu Ile Arg Asp Cys Leu
                165                 170                 175

att tca ggc ggt gat ggg ctg ctc atc aac gac caa att tta gaa tat      576
Ile Ser Gly Gly Asp Gly Leu Leu Ile Asn Asp Gln Ile Leu Glu Tyr
            180                 185                 190

att tta aaa gag ctg cgc agc att ccg cat ctg gaa gtc atc cgc atc      624
Ile Leu Lys Glu Leu Arg Ser Ile Pro His Leu Glu Val Ile Arg Ile
        195                 200                 205

gga aca cgt gct ccc gtc gtc ttt ccg cag cgc att acc gat cat ctg      672
Gly Thr Arg Ala Pro Val Val Phe Pro Gln Arg Ile Thr Asp His Leu
    210                 215                 220

tgc gag ata ttg aaa aaa tat cat ccg gtc tgg ctg aac acc cat ttt      720
Cys Glu Ile Leu Lys Lys Tyr His Pro Val Trp Leu Asn Thr His Phe
225                 230                 235                 240

aac aca agc atc gaa atg aca gaa gaa tcc gtt gag gca tgt gaa aag      768
Asn Thr Ser Ile Glu Met Thr Glu Glu Ser Val Glu Ala Cys Glu Lys
                245                 250                 255

ctg gtg aac gcg gga gtg ccg gtc gga aat cag gct gtc gta tta gca      816
Leu Val Asn Ala Gly Val Pro Val Gly Asn Gln Ala Val Val Leu Ala
            260                 265                 270

ggt att aat gat tcg gtt cca att atg aaa aag ctc atg cat gac ttg      864
Gly Ile Asn Asp Ser Val Pro Ile Met Lys Lys Leu Met His Asp Leu
        275                 280                 285

gta aaa atc aga gtc cgt cct tat tat att tac caa tgt gat ctg tca      912
Val Lys Ile Arg Val Arg Pro Tyr Tyr Ile Tyr Gln Cys Asp Leu Ser
    290                 295                 300

gaa gga ata ggg cat ttc cgt gct cct gtt tcc aaa ggt ttg gag atc      960
Glu Gly Ile Gly His Phe Arg Ala Pro Val Ser Lys Gly Leu Glu Ile
305                 310                 315                 320

att gaa ggg ctg aga ggt cat acc tca ggc tat gcg gtt cct acc ttt     1008
Ile Glu Gly Leu Arg Gly His Thr Ser Gly Tyr Ala Val Pro Thr Phe
                325                 330                 335

gtc gtt cac gca cca ggc gga gga ggt aaa atc gcc ctg cag ccg aac     1056
Val Val His Ala Pro Gly Gly Gly Gly Lys Ile Ala Leu Gln Pro Asn
            340                 345                 350

tat gtc ctg tca caa agt cct gac aaa gtg atc tta aga aat ttt gaa     1104
Tyr Val Leu Ser Gln Ser Pro Asp Lys Val Ile Leu Arg Asn Phe Glu
        355                 360                 365

ggt gtg att acg tca tat ccg gaa cca gag aat tat atc ccc aat cag     1152
```

-continued

```
Gly Val Ile Thr Ser Tyr Pro Glu Pro Glu Asn Tyr Ile Pro Asn Gln
    370                 375                 380

gca gac gcc tat ttt gag tcc gtt ttc cct gaa acc gct gac aaa aag     1200
Ala Asp Ala Tyr Phe Glu Ser Val Phe Pro Glu Thr Ala Asp Lys Lys
385                 390                 395                 400

gag ccg atc ggg ctg agt gcc att ttt gct gac aaa gaa gtt tcg ttt     1248
Glu Pro Ile Gly Leu Ser Ala Ile Phe Ala Asp Lys Glu Val Ser Phe
                405                 410                 415

aca cct gaa aat gta gac aga atc aaa cgg cgt gag gca tac atc gca     1296
Thr Pro Glu Asn Val Asp Arg Ile Lys Arg Arg Glu Ala Tyr Ile Ala
            420                 425                 430

aat ccg gag cat gaa aca tta aaa gat cgg cgt gag aaa aga gat cag     1344
Asn Pro Glu His Glu Thr Leu Lys Asp Arg Arg Glu Lys Arg Asp Gln
        435                 440                 445

ctc aaa gaa aag aaa ttt ttg gcg cag cag aaa aaa cag aaa gag act     1392
Leu Lys Glu Lys Lys Phe Leu Ala Gln Gln Lys Lys Gln Lys Glu Thr
    450                 455                 460

gaa tgc gga ggg gat tct tca taa                                     1416
Glu Cys Gly Gly Asp Ser Ser
465                 470


<210> SEQ ID NO 59
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 59

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220
```

-continued

```
Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 60
<211> LENGTH: 471
<212> TYPE: PRT
<213> ORGANISM: Bacillus subtilis

<400> SEQUENCE: 60

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Leu Glu Asp Pro Leu His Glu Asp Glu Asp
            100                 105                 110

Ser Arg Val Pro Gly Leu Thr His Arg Tyr Pro Asp Arg Val Leu Phe
        115                 120                 125
```

-continued

```
Leu Val Thr Asn Gln Cys Ser Met Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val Asp Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Arg Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470


<210> SEQ ID NO 61
<211> LENGTH: 471
<212> TYPE: PRT
<213> ORGANISM: Bacillus subtilis

<400> SEQUENCE: 61

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
```

-continued

```
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Leu Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Met Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val Asp Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445
```

-continued

```
Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 62
<211> LENGTH: 471
<212> TYPE: PRT
<213> ORGANISM: Artificial Sequence
<220> FEATURE:
<223> OTHER INFORMATION: Synthetic construct - variant 2,3-aminomutase

<400> SEQUENCE: 62

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Arg His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335
```

-continued

```
Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Ser
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Gly Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 63
<211> LENGTH: 49
<212> TYPE: DNA
<213> ORGANISM: artificial sequence
<220> FEATURE:
<223> OTHER INFORMATION: Bacillus specific primer
<220> FEATURE:
<221> NAME/KEY: misc_feature
<223> OTHER INFORMATION: Forward primer

<400> SEQUENCE: 63
ccagcctggc cataaggaga tatacatatg aaaaacaaat ggtataaac 49

<210> SEQ ID NO 64
<211> LENGTH: 50
<212> TYPE: DNA
<213> ORGANISM: artificial sequence
<220> FEATURE:
<223> OTHER INFORMATION: Bacillus specific primer
<220> FEATURE:
<221> NAME/KEY: misc_feature
<223> OTHER INFORMATION: Reverse primer

<400> SEQUENCE: 64
atggtgatgg tgatggtggc cagtttggcc ttatgaagaa tcccctccgc 50

<210> SEQ ID NO 65
<211> LENGTH: 471
<212> TYPE: PRT
<213> ORGANISM: Artificial Sequence
<220> FEATURE:
<223> OTHER INFORMATION: Synthetic construct - variant 2,3-aminomutase
<220> FEATURE:
<221> NAME/KEY: MISC_FEATURE
<222> LOCATION: (2)..(2)
<223> OTHER INFORMATION: Xaa is Glu
<220> FEATURE:
<221> NAME/KEY: MISC_FEATURE
<222> LOCATION: (13)..(13)
<223> OTHER INFORMATION: Xaa is Glu
<220> FEATURE:
<221> NAME/KEY: MISC_FEATURE
<222> LOCATION: (17)..(17)
<223> OTHER INFORMATION: Xaa is Arg
<220> FEATURE:
<221> NAME/KEY: MISC_FEATURE -continued
<222> LOCATION: (19)..(19)
<223> OTHER INFORMATION: Xaa is Arg
<220> FEATURE:
<221> NAME/KEY: MISC_FEATURE
<222> LOCATION: (23)..(23)
<223> OTHER INFORMATION: Xaa is Asp or Gly
<220> FEATURE:
<221> NAME/KEY: MISC_FEATURE
<222> LOCATION: (24)..(24)
<223> OTHER INFORMATION: Xaa is Gly
<220> FEATURE:
<221> NAME/KEY: MISC_FEATURE
<222> LOCATION: (32)..(32)
<223> OTHER INFORMATION: Xaa is Arg
<220> FEATURE:
<221> NAME/KEY: MISC_FEATURE
<222> LOCATION: (35)..(35)
<223> OTHER INFORMATION: Xaa is Arg
<220> FEATURE:
<221> NAME/KEY: MISC_FEATURE
<222> LOCATION: (38)..(38)
<223> OTHER INFORMATION: Xaa is Gly
<220> FEATURE:
<221> NAME/KEY: MISC_FEATURE
<222> LOCATION: (43)..(43)
<223> OTHER INFORMATION: Xaa is Ser
<220> FEATURE:
<221> NAME/KEY: MISC_FEATURE
<222> LOCATION: (67)..(67)
<223> OTHER INFORMATION: Xaa is Ser
<220> FEATURE:
<221> NAME/KEY: MISC_FEATURE
<222> LOCATION: (71)..(71)
<223> OTHER INFORMATION: Xaa is Cys
<220> FEATURE:
<221> NAME/KEY: MISC_FEATURE
<222> LOCATION: (72)..(72)
<223> OTHER INFORMATION: Xaa is His or Trp
<220> FEATURE:
<221> NAME/KEY: MISC_FEATURE
<222> LOCATION: (73)..(73)
<223> OTHER INFORMATION: Xaa is Val
<220> FEATURE:
<221> NAME/KEY: MISC_FEATURE
<222> LOCATION: (74)..(74)
<223> OTHER INFORMATION: Xaa is Pro
<220> FEATURE:
<221> NAME/KEY: MISC_FEATURE
<222> LOCATION: (79)..(79)
<223> OTHER INFORMATION: Xaa is Glu
<220> FEATURE:
<221> NAME/KEY: MISC_FEATURE
<222> LOCATION: (80)..(80)
<223> OTHER INFORMATION: Xaa is K
<220> FEATURE:
<221> NAME/KEY: MISC_FEATURE
<222> LOCATION: (93)..(93)
<223> OTHER INFORMATION: Xaa is Pro
<220> FEATURE:
<221> NAME/KEY: MISC_FEATURE
<222> LOCATION: (96)..(96)
<223> OTHER INFORMATION: Xaa is Ile
<220> FEATURE:
<221> NAME/KEY: MISC_FEATURE
<222> LOCATION: (98)..(98)
<223> OTHER INFORMATION: Xaa is Thr
<220> FEATURE:
<221> NAME/KEY: MISC_FEATURE
<222> LOCATION: (99)..(99)
<223> OTHER INFORMATION: Xaa is Ser
<220> FEATURE:
<221> NAME/KEY: MISC_FEATURE
<222> LOCATION: (108)..(108)
<223> OTHER INFORMATION: Xaa is Arg
<220> FEATURE:
<221> NAME/KEY: MISC_FEATURE
<222> LOCATION: (109)..(109)
<223> OTHER INFORMATION: Xaa is Gly
<220> FEATURE:

-continued

<221> NAME/KEY: MISC_FEATURE
<222> LOCATION: (114)..(114)
<223> OTHER INFORMATION: Xaa is Pro
<220> FEATURE:
<221> NAME/KEY: MISC_FEATURE
<222> LOCATION: (118)..(118)
<223> OTHER INFORMATION: Xaa is Pro
<220> FEATURE:
<221> NAME/KEY: MISC_FEATURE
<222> LOCATION: (124)..(124)
<223> OTHER INFORMATION: Xaa is Asn
<220> FEATURE:
<221> NAME/KEY: MISC_FEATURE
<222> LOCATION: (132)..(132)
<223> OTHER INFORMATION: Xaa is Asp or Ser
<220> FEATURE:
<221> NAME/KEY: MISC_FEATURE
<222> LOCATION: (134)..(134)
<223> OTHER INFORMATION: Xaa is Gly
<220> FEATURE:
<221> NAME/KEY: MISC_FEATURE
<222> LOCATION: (135)..(135)
<223> OTHER INFORMATION: Xaa is Pro
<220> FEATURE:
<221> NAME/KEY: MISC_FEATURE
<222> LOCATION: (136)..(136)
<223> OTHER INFORMATION: Xaa is Val
<220> FEATURE:
<221> NAME/KEY: MISC_FEATURE
<222> LOCATION: (137)..(137)
<223> OTHER INFORMATION: Xaa is His
<220> FEATURE:
<221> NAME/KEY: MISC_FEATURE
<222> LOCATION: (140)..(140)
<223> OTHER INFORMATION: Xaa is His
<220> FEATURE:
<221> NAME/KEY: MISC_FEATURE
<222> LOCATION: (141)..(141)
<223> OTHER INFORMATION: Xaa is Arg
<220> FEATURE:
<221> NAME/KEY: MISC_FEATURE
<222> LOCATION: (145)..(145)
<223> OTHER INFORMATION: Xaa is Leu
<220> FEATURE:
<221> NAME/KEY: MISC_FEATURE
<222> LOCATION: (156)..(156)
<223> OTHER INFORMATION: Xaa is Glu
<220> FEATURE:
<221> NAME/KEY: MISC_FEATURE
<222> LOCATION: (187)..(187)
<223> OTHER INFORMATION: Xaa is Gly
<220> FEATURE:
<221> NAME/KEY: MISC_FEATURE
<222> LOCATION: (197)..(197)
<223> OTHER INFORMATION: Xaa is Pro
<220> FEATURE:
<221> NAME/KEY: MISC_FEATURE
<222> LOCATION: (200)..(200)
<223> OTHER INFORMATION: Xaa is Thr
<220> FEATURE:
<221> NAME/KEY: MISC_FEATURE
<222> LOCATION: (203)..(203)
<223> OTHER INFORMATION: Xaa is Pro
<220> FEATURE:
<221> NAME/KEY: MISC_FEATURE
<222> LOCATION: (204)..(204)
<223> OTHER INFORMATION: Xaa is Gly
<220> FEATURE:
<221> NAME/KEY: MISC_FEATURE
<222> LOCATION: (224)..(224)
<223> OTHER INFORMATION: Xaa is Pro
<220> FEATURE:
<221> NAME/KEY: MISC_FEATURE
<222> LOCATION: (230)..(230)
<223> OTHER INFORMATION: Xaa is Arg
<220> FEATURE:
<221> NAME/KEY: MISC_FEATURE
<222> LOCATION: (231)..(231)
<223> OTHER INFORMATION: Xaa is His

-continued

<220> FEATURE:
<221> NAME/KEY: MISC_FEATURE
<222> LOCATION: (235)..(235)
<223> OTHER INFORMATION: Xaa is Arg
<220> FEATURE:
<221> NAME/KEY: MISC_FEATURE
<222> LOCATION: (237)..(237)
<223> OTHER INFORMATION: Xaa is Asp
<220> FEATURE:
<221> NAME/KEY: MISC_FEATURE
<222> LOCATION: (240)..(240)
<223> OTHER INFORMATION: Xaa is Leu
<220> FEATURE:
<221> NAME/KEY: MISC_FEATURE
<222> LOCATION: (250)..(250)
<223> OTHER INFORMATION: Xaa is Pro
<220> FEATURE:
<221> NAME/KEY: MISC_FEATURE
<222> LOCATION: (254)..(254)
<223> OTHER INFORMATION: Xaa is Tyr or Arg
<220> FEATURE:
<221> NAME/KEY: MISC_FEATURE
<222> LOCATION: (276)..(276)
<223> OTHER INFORMATION: Xaa is G
<220> FEATURE:
<221> NAME/KEY: MISC_FEATURE
<222> LOCATION: (280)..(280)
<223> OTHER INFORMATION: Xaa is Thr
<220> FEATURE:
<221> NAME/KEY: MISC_FEATURE
<222> LOCATION: (281)..(281)
<223> OTHER INFORMATION: Xaa is Ile or Val
<220> FEATURE:
<221> NAME/KEY: MISC_FEATURE
<222> LOCATION: (307)..(307)
<223> OTHER INFORMATION: Xaa is Leu
<220> FEATURE:
<221> NAME/KEY: MISC_FEATURE
<222> LOCATION: (308)..(308)
<223> OTHER INFORMATION: Xaa is Arg
<220> FEATURE:
<221> NAME/KEY: MISC_FEATURE
<222> LOCATION: (310)..(310)
<223> OTHER INFORMATION: Xaa is Ser
<220> FEATURE:
<221> NAME/KEY: MISC_FEATURE
<222> LOCATION: (311)..(311)
<223> OTHER INFORMATION: Xaa is Cys
<220> FEATURE:
<221> NAME/KEY: MISC_FEATURE
<222> LOCATION: (319)..(319)
<223> OTHER INFORMATION: Xaa is Gly
<220> FEATURE:
<221> NAME/KEY: MISC_FEATURE
<222> LOCATION: (329)..(329)
<223> OTHER INFORMATION: Xaa is Pro
<220> FEATURE:
<221> NAME/KEY: MISC_FEATURE
<222> LOCATION: (331)..(331)
<223> OTHER INFORMATION: Xaa is Asn
<220> FEATURE:
<221> NAME/KEY: MISC_FEATURE
<222> LOCATION: (339)..(339)
<223> OTHER INFORMATION: Xaa is His
<220> FEATURE:
<221> NAME/KEY: MISC_FEATURE
<222> LOCATION: (350)..(350)
<223> OTHER INFORMATION: Xaa is Arg
<220> FEATURE:
<221> NAME/KEY: MISC_FEATURE
<222> LOCATION: (360)..(360)
<223> OTHER INFORMATION: Xaa is Gly
<220> FEATURE:
<221> NAME/KEY: MISC_FEATURE
<222> LOCATION: (380)..(380)
<223> OTHER INFORMATION: Xaa is Cys
<220> FEATURE:
<221> NAME/KEY: MISC_FEATURE
<222> LOCATION: (381)..(381)

```
<223> OTHER INFORMATION: Xaa is Thr
<220> FEATURE:
<221> NAME/KEY: MISC_FEATURE
<222> LOCATION: (393)..(393)
<223> OTHER INFORMATION: Xaa is Ser
<220> FEATURE:
<221> NAME/KEY: MISC_FEATURE
<222> LOCATION: (395)..(395)
<223> OTHER INFORMATION: Xaa is Gly
<220> FEATURE:
<221> NAME/KEY: MISC_FEATURE
<222> LOCATION: (408)..(408)
<223> OTHER INFORMATION: Xaa is Leu
<220> FEATURE:
<221> NAME/KEY: MISC_FEATURE
<222> LOCATION: (411)..(411)
<223> OTHER INFORMATION: Xaa is Gly
<220> FEATURE:
<221> NAME/KEY: MISC_FEATURE
<222> LOCATION: (416)..(416)
<223> OTHER INFORMATION: Xaa is Ser
<220> FEATURE:
<221> NAME/KEY: MISC_FEATURE
<222> LOCATION: (422)..(422)
<223> OTHER INFORMATION: Xaa is Val
<220> FEATURE:
<221> NAME/KEY: MISC_FEATURE
<222> LOCATION: (440)..(440)
<223> OTHER INFORMATION: Xaa is Glu
<220> FEATURE:
<221> NAME/KEY: MISC_FEATURE
<222> LOCATION: (445)..(445)
<223> OTHER INFORMATION: Xaa is Lys
<220> FEATURE:
<221> NAME/KEY: MISC_FEATURE
<222> LOCATION: (447)..(447)
<223> OTHER INFORMATION: Xaa is Gly
<220> FEATURE:
<221> NAME/KEY: MISC_FEATURE
<222> LOCATION: (454)..(454)
<223> OTHER INFORMATION: Xaa is Ser
<220> FEATURE:
<221> NAME/KEY: MISC_FEATURE
<222> LOCATION: (455)..(455)
<223> OTHER INFORMATION: Xaa is Ser

<400> SEQUENCE: 65

Met Xaa Asn Lys Trp Tyr Lys Pro Lys Arg His Trp Xaa Glu Ile Glu
1               5                   10                  15

Xaa Trp Xaa Asp Val Pro Xaa Xaa Lys Trp Asn Asp Trp Leu Trp Xaa
            20                  25                  30

Leu Thr Xaa Thr Val Xaa Thr Leu Asp Asp Xaa Lys Lys Val Ile Asn
        35                  40                  45

Leu Thr Glu Asp Glu Glu Glu Gly Val Arg Ile Ser Thr Lys Thr Ile
    50                  55                  60

Pro Leu Xaa Ile Thr Pro Xaa Xaa Xaa Xaa Leu Met Asp Pro Xaa Xaa
65                  70                  75                  80

Pro Arg Cys Pro Val Arg Met Gln Ser Val Pro Leu Xaa Glu Glu Xaa
            85                  90                  95

His Xaa Xaa Lys Tyr Asp Leu Glu Asp Pro Leu Xaa Xaa Asp Glu Asp
            100                 105                 110

Ser Xaa Val Pro Gly Xaa Thr His Arg Tyr Pro Xaa Arg Val Leu Phe
        115                 120                 125

Leu Val Thr Xaa Gln Xaa Xaa Xaa Xaa Cys Arg Xaa Xaa Thr Arg Arg
    130                 135                 140

Xaa Phe Ser Gly Gln Ile Gly Met Gly Val Pro Xaa Lys Gln Leu Asp
145                 150                 155                 160

Ala Ala Ile Ala Tyr Ile Arg Glu Thr Pro Glu Ile Arg Asp Cys Leu
```

-continued

```
                165                 170                 175

Ile Ser Gly Gly Asp Gly Leu Leu Ile Asn Xaa Gln Ile Leu Glu Tyr
            180                 185                 190

Ile Leu Lys Glu Xaa Arg Ser Xaa Pro His Xaa Xaa Val Ile Arg Ile
        195                 200                 205

Gly Thr Arg Ala Pro Val Val Phe Pro Gln Arg Ile Thr Asp His Xaa
    210                 215                 220

Cys Glu Ile Leu Lys Xaa Xaa His Pro Val Xaa Leu Xaa Thr His Xaa
225                 230                 235                 240

Asn Thr Ser Ile Glu Met Thr Glu Glu Xaa Val Glu Ala Xaa Glu Lys
                245                 250                 255

Leu Val Asn Ala Gly Val Pro Val Gly Asn Gln Ala Val Val Leu Ala
            260                 265                 270

Gly Ile Asn Xaa Ser Val Pro Xaa Xaa Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Xaa Xaa His Xaa Xaa Ala Pro Val Ser Lys Gly Leu Xaa Ile
305                 310                 315                 320

Ile Glu Gly Leu Arg Gly His Thr Xaa Gly Xaa Ala Val Pro Thr Phe
                325                 330                 335

Val Val Xaa Ala Pro Gly Gly Gly Gly Lys Ile Ala Leu Xaa Pro Asn
            340                 345                 350

Tyr Val Leu Ser Gln Ser Pro Xaa Lys Val Ile Leu Arg Asn Phe Glu
        355                 360                 365

Gly Val Ile Thr Ser Tyr Pro Glu Pro Glu Asn Xaa Xaa Pro Asn Gln
    370                 375                 380

Ala Asp Ala Tyr Phe Glu Ser Val Xaa Pro Xaa Thr Ala Asp Lys Lys
385                 390                 395                 400

Glu Pro Ile Gly Leu Ser Ala Xaa Phe Ala Xaa Lys Glu Val Ser Xaa
                405                 410                 415

Thr Pro Glu Asn Val Xaa Arg Ile Lys Arg Arg Glu Ala Tyr Ile Ala
            420                 425                 430

Asn Pro Glu His Glu Thr Leu Xaa Asp Arg Arg Glu Xaa Arg Xaa Gln
        435                 440                 445

Leu Lys Glu Lys Lys Xaa Xaa Ala Gln Gln Lys Lys Gln Lys Glu Thr
    450                 455                 460

Glu Cys Gly Gly Asp Ser Ser
465                 470
```